US012365909B2

(12) United States Patent
Devine et al.

(10) Patent No.: US 12,365,909 B2
(45) Date of Patent: *Jul. 22, 2025

(54) INBRED TRANSGENIC CANOLA LINE NS-B50027-4 AND SEEDS THEREOF

(71) Applicant: NUSEED NUTRITIONAL AUSTRALIA PTY LTD, Victoria (AU)

(72) Inventors: Malcolm Devine, Calgary (CA); Antonio Leonforte, Horsham (AU); Nelson Gororo, Horsham (AU); Greg Buzza, Horsham (AU); Shunxue Tang, West Sacramento, CA (US); Wenxiang Gao, West Sacramento, CA (US)

(73) Assignee: NUSEED NUTRITIONAL AUSTRALIA PTY LTD, Victoria (AU)

( * ) Notice: Subject to any disclaimer, the term of this patent is extended or adjusted under 35 U.S.C. 154(b) by 527 days.

This patent is subject to a terminal disclaimer.

(21) Appl. No.: 17/669,783

(22) Filed: Feb. 11, 2022

(65) Prior Publication Data

US 2022/0162630 A1 May 26, 2022

Related U.S. Application Data

(63) Continuation of application No. 16/792,046, filed on Feb. 14, 2020, now abandoned, which is a continuation of application No. 15/626,019, filed on Jun. 16, 2017, now Pat. No. 10,563,218.

(60) Provisional application No. 62/351,250, filed on Jun. 16, 2016.

(51) Int. Cl.
*A01H 5/10* (2018.01)
*A01H 6/20* (2018.01)
*C12N 15/82* (2006.01)

(52) U.S. Cl.
CPC ........... *C12N 15/8247* (2013.01); *A01H 5/10* (2013.01); *A01H 6/20* (2018.05); *A01H 6/202* (2018.05)

(58) Field of Classification Search
None
See application file for complete search history.

(56) References Cited

U.S. PATENT DOCUMENTS

| | | |
|---|---|---|
| 4,769,061 A | 9/1988 | Comai |
| 4,810,648 A | 3/1989 | Stalker |
| 4,940,835 A | 7/1990 | Shah et al. |
| 5,266,317 A | 11/1993 | Tomalski et al. |
| 5,478,369 A | 12/1995 | Albertsen et al. |
| 5,591,616 A | 1/1997 | Hiei et al. |
| 5,767,373 A | 6/1998 | Ward et al. |
| 5,824,524 A | 10/1998 | Albertsen et al. |
| 5,850,014 A | 12/1998 | Albertsen et al. |
| 5,859,341 A | 1/1999 | Albertsen et al. |
| 5,959,185 A | 9/1999 | Streit et al. |
| 5,969,212 A | 10/1999 | Getschman |
| 5,973,234 A | 10/1999 | Mueller et al. |
| 5,977,445 A | 11/1999 | Soper et al. |
| 6,225,529 B1 | 5/2001 | Lappegard et al. |
| 6,265,640 B1 | 7/2001 | Albertsen et al. |
| 6,282,837 B1 | 9/2001 | Ward et al. |
| 6,288,306 B1 | 9/2001 | Ward et al. |
| 6,297,426 B1 | 10/2001 | Albertsen et al. |
| 6,599,513 B2 | 7/2003 | Deckers et al. |
| 7,164,059 B2 | 1/2007 | Barham |
| 8,816,111 B2 | 8/2014 | Petrie et al. |
| 8,946,460 B2 | 2/2015 | Petrie et al. |
| 8,975,374 B2 | 3/2015 | Kimura |
| 9,932,541 B2 | 4/2018 | Petrie et al. |
| 9,969,954 B2 | 5/2018 | Petrie et al. |
| 10,125,084 B2 | 11/2018 | Petrie et al. |
| 10,563,218 B2 | 2/2020 | Devine et al. |
| 2003/0110532 A1 | 6/2003 | Arnostrong et al. |
| 2006/0225158 A1 | 10/2006 | Jonsson |
| 2006/0246556 A1 | 11/2006 | Napier et al. |
| 2008/0241082 A1 | 10/2008 | Guth et al. |
| 2010/0092640 A1 | 4/2010 | Ursin et al. |
| 2011/0321187 A1 | 12/2011 | Malcuit et al. |
| 2013/0338388 A1 | 12/2013 | Petrie et al. |
| 2015/0045569 A1 | 2/2015 | Petrie et al. |
| 2015/0166928 A1 | 6/2015 | Petrie et al. |
| 2015/0374654 A1 | 12/2015 | Petrie et al. |
| 2016/0002566 A1 | 1/2016 | Vanhercke et al. |
| 2016/0150747 A1 | 6/2016 | Aggarwal et al. |
| 2018/0016590 A1 | 1/2018 | Devine et al. |
| 2018/0016591 A1 | 1/2018 | Devine et al. |
| 2020/0092640 A1 | 3/2020 | Yang et al. |
| 2020/0172919 A1 | 6/2020 | Devine et al. |

FOREIGN PATENT DOCUMENTS

| | | |
|---|---|---|
| AU | 2013204254 B2 | 5/2013 |
| BR | 112018076323 A2 | 3/2019 |
| CL | 2014003402 A1 | 12/2015 |

(Continued)

OTHER PUBLICATIONS

Sanders, et al., "Comparison of Cauliflower Mosaic Virus 35S and Nopaline Synthase Promoters in Transgenic Plants", Nucleic Acids Research, vol. 15, No. 4, 1987, pp. 1543-1558.

Schena, et al., "A Steroid-Inducible Gene Expression System for Plant Cells", PNAS, vol. 88, Dec. 1991, pp. 10421-10425.

Seberry, et al., "Quality of Australian Canola", Department of Primary Industries, Australian Oilseeds Federation, vol. 18, 2011-12, 34 pages.

(Continued)

*Primary Examiner* — Phuong T Bui

(74) *Attorney, Agent, or Firm* — Wiley Rein LLP

(57) ABSTRACT

The present embodiments relate to inbred transgenic canola line NS-B50027-4; seeds and oils obtained from NS-B50027-4; and progeny derived from NS-B50027-4. In particular, NS-B50027-4 is a true-breeding canola line capable of producing at least 5% DHA in its seed oil.

2 Claims, 3 Drawing Sheets
Specification includes a Sequence Listing.

(56) References Cited

FOREIGN PATENT DOCUMENTS

| | | | |
|---|---|---|---|
| CL | 2018003628 A1 | 8/2019 | |
| CN | 104853596 A | 8/2015 | |
| CN | 109661458 A | 4/2019 | |
| EP | 0242246 A1 | 10/1987 | |
| EP | 0333033 A1 | 9/1989 | |
| EP | 3472280 A1 | 4/2019 | |
| JP | 2012-509059 A | 4/2012 | |
| JP | 2015-528027 A | 9/2015 | |
| JP | 2019-520088 A | 7/2019 | |
| KR | 10-2019-0029594 A | 3/2019 | |
| SG | 11201811219 U | 1/2019 | |
| WO | 92/13956 A1 | 8/1992 | |
| WO | 92/13957 A1 | 8/1992 | |
| WO | 93/02197 A1 | 2/1993 | |
| WO | 95/16776 A1 | 6/1995 | |
| WO | 95/18855 A2 | 7/1995 | |
| WO | 96/30530 A1 | 10/1996 | |
| WO | 00/11177 A1 | 3/2000 | |
| WO | 01/12825 A1 | 2/2001 | |
| WO | 01/16340 A1 | 3/2001 | |
| WO | 01/29237 A2 | 4/2001 | |
| WO | 2010/057246 A1 | 5/2010 | |
| WO | 2013/185184 A2 | 12/2013 | |
| WO | 2015/089587 A1 | 6/2015 | |
| WO | 2017/218969 A1 | 12/2017 | |
| WO | 2017/219006 A1 | 12/2017 | |

OTHER PUBLICATIONS

Shrestha, et al., "A MetaAnalysis of the Impact of Anaerobic Soil Disinfestation on Pest Suppression and Yield of Horticultural Crops", Frontiers in Plant Science, vol. 7, Article 1254, Aug. 2016, 20 pages.
Smith, et al., "Analyzing Variety by Environment Data Using Multiplicative Mixed Models and Adjustments for Spatial Field Trend", Biometrics, vol. 57, Dec. 2001, pp. 1138-1147.
Sosnowski, et al., "Infection of Australian Canola Cultivars (*Brassica napus*) by Leptosphaeria Maculans is Influenced by Cultivar and Environmental Conditions", Australasian Plant Pathology, vol. 33, 2004, pp. 401-411.
Stalberg, et al., "Deletion Analysis of a 2S Seed Storage Protein Promoter of Brassica Napus in Transgenic Tobacco", Plant Molecular Biology, vol. 23, 1993, pp. 671-683.
Steifel, et al., "Expression of a Maize Cell Wall Hydroxyproline—Rich Glycoprotein Gene in Early Leaf and Root Vascular Differentiation", The Plant Cell, vol. 2, Aug. 1990, pp. 785-793.
Strobel, et al., "Survey of n-3 and n-6 Polyunsaturated Fatty Acids in Fish and Fish Products", Lipids in Health and Disease, vol. 11, No. 144, 2012, 10 pages.
Thompson, et al., "Structural Elements Regulating Zein Gene Expression", BioEssays, vol. 10, Apr. 1989, pp. 108-113.
Tinoco, et al., "Analysis of Fatty Acid Mixtures: Comparison of Two "Absolute" Methods of Determination", Analytical Biochemistry, vol. 3, 1962, pp. 514-518.
Tocher, Douglas R., "Omega-3 Long-Chain Polyunsaturated Fatty Acids and Aquaculture in Perspective", Aquaculture, vol. 449, 2015, pp. 94-107.
Van Blokland, et al., "Transgene-Mediated Suppression of Chalcone Synthase Expression in Petunia Hybrida Results from an Increase in RNA Turnover", The Plant Journal, vol. 6, No. 6, 1994, pp. 861-877.
Van De Wouw, et al., "Blackleg Disease of Canola in Australia", Crop and Pasture Science, vol. 67, 2016, pp. 273283.
Velten, et al., "Isolation of a Dual Plant Promoter Fragment from the Ti Plasmid of Agrobacterium Tumefaciens", The EMBO Journal, vol. 3, No. 12, 1984, pp. 2723-2730.
Ward, et al., "Chemical Regulation of Transgene Expression in Plants", Plant Molecular Biology, vol. 22, 1993, pp. 361-366.
WHO Technical Report Series 916, "Diet, Nutrition and the Prevention of Chronic Diseases", Report of a Joint WHO/FAO Expert Consultation, Geneva, 2003, 160 pages.

Office Action received for Chinese Patent Application Serial No. 201780051974.4 dated Jan. 6, 2022, 24 pages (Including English Translation).
Petrie, James R. et al. "Metabolic Engineering Camelina sativa with Fish Oil-Like Levels of DHA", Plos One, vol. 9, No. 1 (Jan. 1, 2012), pp. 1-8.
Official Notification dated Apr. 26, 2022 relating to Israeli Patent Application No. 263725.
"Extended European Search Report received for European Patent Application No. 17814219.6, mailed on Oct. 25, 2019", 8 pages.
"International Preliminary Report on Patentability received for PCT Patent Application No. PCTUS2017037997, mailed on Dec. 27, 2018", 14 pages.
"International Search Report and Written Opinion received for PCT Patent Application No. PCTUS2017037997, mailed on Nov. 3, 2017", 17 pages.
"Non-Final Office Action received for U.S. Appl. No. 15/626,019, mailed on Nov. 15, 2018", 12 pages.
Adamczak, Marek, "The Application of Lipases in Modifying the Composition, Structure and Properties of Lipids—A Review", Polish Journal of Food and Nutrition Sciences, vol. 13/54, No. 1, 2004, pp. 3-10.
Armstrong, et al., "Establishment and Maintenance of Friable, Embryogenic Maize Callus and the Involvement of L-Proline", Planta, vol. 164, 1985, pp. 207-214.
Atanassova, et al., "A 126 bp Fragment of a Plant Histone Gene Promoter Confers Preferential Expression in Meristems of Transgenic Arabidopsis", The Plant Journal, vol. 2, No. 3, 1992, pp. 291-300.
Bernardo, et al., "North American Study on Essential Derivation in Maize: Inbreds Developed without and with Selection from F2 Populations", Theoretical and Applied Genetics, vol. 102, 2001, pp. 986-992.
Betancor, et al., "A Nutritionally-Enhanced Oil from Transgenic Camelina Sativa Effectively Replaces Fish Oil as a Source of Eicosapentaenoic Acid for Fish", Scientific Reports, vol. 5, No. 8104, 2014, pp. 1-10.
Bevan, Michael, "Binary Agrobacterium Vectors for Plant Transformation", Nucleic Acids Research, vol. 12, No. 22, 1984, pp. 8711-8721.
Christensen, et al., "Maize Polyubiquitin Genes: Structure, Thermal Perturbation of Expression and Transcript Splicing, and Promoter Activity Following Transfer to Protoplasts by Electroporation", Plant Molecular Biology, vol. 18, 1992, pp. 675-689.
Christensen, et al., "Sequence Analysis and Transcriptional Regulation by Heat Shock of Polyubiquitin Transcripts from Maize", Plant Molecular Biology, vol. 12, 1989, pp. 619-632.
Close, et al., "The Effect of Auxin-Like Plant Growth Regulators and Osmotic Regulation on Induction of Somatic Embryogenesis from Elite Maize Inbreds", Plant Science, vol. 52, 1987, pp. 81-89.
Coutu, et al., "pORE: A Modular Binary Vector Series Suited for Both Monocot and Dicot Plant Transformation", Transgenic Research, vol. 16, 2007, pp. 771-781.
Creissen, et al., "Molecular Characterization of Glutathione Reductase cDNAs from pea (*Pisum sativum* L.)", The Plant Journal, vol. 2, No. 1, 1991, pp. 128-131.
Cullis, et al., "Spatial Analysis of Field Experiments—An Extension to Two Dimensions", Biometrics, vol. 47, No. 4, 1991, pp. 1449-1460.
Diwan, et al., "Automated Sizing of Fluorescent-Labeled Simple Sequence Repeat (SSR) Markers to Assay Genetic Variation in Soybean", Theoretical and Applied Genetics, vol. 95, 1997, pp. 723-733.
Fehr, Walter R., "Principles of Cultivar Development: Theory and Technique", vol. 1, 1993, 551 pages.
Ferreiradias, et al., "The Potential Use of Lipases in the Production of Fatty Acid Derivatives for the Food and Nutraceutical Industries", Electronic Journal of Biotechnology, vol. 16, No. 3, 2013, 38 pages.
Fontes, et al., "Characterization of an Immunoglobulin Binding Protein Homolog in the Maize floury-2 Endosperm Mutant", The Plant Cell, vol. 3, May 1991, pp. 483-496.
Fraley, et al., "Expression of Bacterial Genes in Plant Cells", PNAS, vol. 80, Aug. 1983, pp. 4803-4807.

(56) References Cited

OTHER PUBLICATIONS

Gámez-Meza, et al., "Concentration of Eicosapentaenoic Acid and Docosahexaenoic Acid from Fish Oil by Hydrolysis and Urea Complexation", Food Research International, vol. 36, 2003, pp. 721-727.
Gatz, et al., "Regulation of a Modified CaMV 35S Promoter by the Tn10-Encoded Tet Repressor in Transgenic Tobacco", Molecular Genetics and Genomics, vol. 227, 1991, pp. 229-237.
Gilmour, et al., "ASReml User Guide—Release 3.0", NSW Department of Industry and Investment, 2009, 398 pages.
Kalderon, et al., "A Short Amino Acid Sequence Able to Specify Nuclear Location", Cell, vol. 39, Dec. 1984, pp. 499-509.
Kay, et al., "Duplication of CaMV 35S Promoter Sequences Creates a Strong Enhancer for Plant Genes", Science, vol. 236, No. 4806, Jun. 1987, pp. 1299-1302.
Knox, et al., "Structure and Organization of Two Divergent α-Amylase Genes from Barley", Plant Molecular Biology, vol. 9, 1987, pp. 3-17.
Kumar, et al., "Vegetable Oil: Nutritional and Industrial Perspective", Current Genomics, vol. 17, No. 3, Jun. 2016, pp. 230-240.
Last, et al., "pEmu: An Improved Promoter for Gene Expression in Cereal Cells", Theoretical and Applied Genetics, vol. 81, 1991, pp. 581-588.
Lepetit, et al., "A Plant Histone Gene Promoter Can Direct Both Replication-Dependent and -Independent Gene Expression in Transgenic Plants", Molecular Genetics and Genomics, vol. 231, 1992, pp. 276-285.
Lerner, et al., "Cloning and Characterization of Root-Specific Barley Lectin", Plant Physiology, vol. 91, 1989, pp. 124-129.
Mansour, et al., "Characterization of Oilseed Lipids from 'DHA-Producing Camelina saliva': A New Transformed Land Plant Containing Long-Chain Omega-3 Oils", Nutrients, vol. 6, 2014, pp. 776-789.
Marcroft, et al., "Blackleg of Canola", Agriculture Victoria, Note No. AG1352, May 2008, 2 pages.
Matsuoka, et al., "Propeptide of a Precursor to a Plant Vacuolar Protein Required for Vacuolar Targeting", PNAS, vol. 88, Feb. 1991, pp. 834-838.
Mcelroy, et al., "Isolation of an Efficient Actin Promoter for Use in Rice Transformation", The Plant Cell, vol. 2, Feb. 1990, pp. 163-171.
Mett, et al., "Copper-Controllable Gene Expression System for Whole Plants", PNAS, vol. 90, May 1993, pp. 4567-4571.
Moloney, et al., "High Efficiency Transformation of *Brassica napus* Using Agrobacterium Vectors", Plant Cell Reports, vol. 8, 1989, pp. 238-242.
Napoli, et al., "Introduction of a Chimeric Chalcone Synthase Gene into Petunia Results in Reversible Co-Suppression of Homologous Genes in trans", The Plant Cell, vol. 2, Apr. 1990, pp. 279-289.
Odell, et al., "Identification of DNA Sequences Required for Activity of the Cauliflower Mosaic Virus 35S Promoter", Nature, vol. 313, Feb. 1985, pp. 810-812.
Patterson, et al., "Health Implications of High Dietary Omega-6 Polyunsaturated Fatty Acids", Journal of Nutrition and Metabolism, vol. 2012, No. 539426, 2012, 16 pages.
Petrie, et al., "Isolation and Characterisation of a High-Efficiency Desaturase and Elongases from Microalgae for Transgenic LC-PUFA Production", Marine Biotechnology, vol. 12, No. 4, Oct. 10, 2009, pp. 430-438.
Petrie, et al., "Metabolic Engineering Camelina Sativa with Fish Oil-Like Levels of DHA", PLOS One, vol. 9, Issue 1, Jan. 2014, pp. 1-8.
Petrie, et al., "Metabolic Engineering of Omega-3 long-Chain Polyunsaturated Fatty Acids in Plants using an Acyl-CoA Δ6-Desaturase with ω3-Preference from the Marine Microalga Micromonas pusilla", Metabolic Engineering, vol. 12, 2010, pp. 233-240.
Petrie, et al., "Metabolic Engineering Plant Seeds with Fish Oil-Like Levels of DHA", PLOS One, vol. 7, No. 11. Nov. 2012, 7 pages.
Petrie, et al., "Rapid Expression of Transgenes Driven by Seed-Specific Constructs in Leaf Tissue: DHA Production", Plant Methods, vol. 6, No. 8, 2010, 6 pages.
Petrie, et al., "Transgenic Production of Arachidonic Acid in Oilseeds", Transgenic Research, vol. 21, 2012, pp. 139-147.
Poehlman, et al., "Bredding Field Crops", 1994, 495 pages.
Roder, et al., "Efficiency of the Tetracycline-Dependent Gene Expression System: Complete Suppression and Efficient Induction of the rolB Phenotype in Transgenic Plants", Molecular Genetics and Genomics, vol. 243, 1994, pp. 32-38.
Rogers, et al., "Investigation of Factors Involved in Foreign Protein Expression in Transformed Plants", Biotechnology in Plant Science, 1985, pp. 219-223.
Rossak, et al., "Expression of the FAE1 Gene and FAE1 Promoter Activity in Developing Seeds of *Arabidopsis thaliana*", Plant Molecular Biology, vol. 46, 2001, pp. 717-725.
Wang, et al., "Variance of Marker Estimates of Parental Contribution to F2 and BC1-Derived Inbreds", Crop Science, vol. 40, 2000, pp. 659-665.
International Search Report and Written Opinion mailed, on Apr. 27. 2020, in related Singapore Application No. 11201811219 U, filed on Jun. 16, 2017.
Office Action received for Brazilian Patent Application No. 1120180763144, mailed on Jun. 2, 2021, 4 pages (Official Copy only). (See Communication Attached).
Office Action received for Brazilian Patent Application No. 1120180763233, mailed on Jun. 2, 2021, 4 pages (Official Copy only). (See Communication Attached).
Office Action received for Chilean Patent Application No. 201803628, mailed on Apr. 12, 2021, 15 pages (Official Copy only). (See Communication Attached).
Office Action received for Chilean Patent Application No. 201803631, mailed on Aug. 10, 2020, 12 pages (Official Copy only). (See Communication Attached).
Office Action received for Japanese Patent Application No. 2019-518179, mailed on May 24, 2021, 8 pages (4 pages of English Translation and 4 pages of Official Copy).
Office Action received for Japanese Patent Application No. 2019-518180, mailed on Jul. 5, 2021, 10 pages (5 pages of English Translation and 5 pages of Official copy).

SEQUENCE LISTING

<160> NUMBER OF SEQ ID NOS: 90

<210> SEQ ID NO 1
<211> LENGTH: 44
<212> TYPE: DNA
<213> ORGANISM: Artificial Sequence
<220> FEATURE:
<223> OTHER INFORMATION: KASP primer

<400> SEQUENCE: 1
gaaggtgacc aagttcatgc tccaagcacc gtagtaagag agca                    44

<210> SEQ ID NO 2
<211> LENGTH: 26
<212> TYPE: DNA
<213> ORGANISM: Artificial Sequence
<220> FEATURE:
<223> OTHER INFORMATION: KASP primer

<400> SEQUENCE: 2
gctaagaagt ggggactcaa ctacaa                                        26

<210> SEQ ID NO 3
<211> LENGTH: 41
<212> TYPE: DNA
<213> ORGANISM: Artificial Sequence
<220> FEATURE:
<223> OTHER INFORMATION: KASP primer

<400> SEQUENCE: 3
gaaggtgacc aagttcatgc tgctcttgct ggaactcttg g                       41

<210> SEQ ID NO 4
<211> LENGTH: 26
<212> TYPE: DNA
<213> ORGANISM: Artificial Sequence
<220> FEATURE:
<223> OTHER INFORMATION: KASP primer

<400> SEQUENCE: 4
gggttagcca cattgtaggt aacgta                                        26

<210> SEQ ID NO 5
<211> LENGTH: 44
<212> TYPE: DNA
<213> ORGANISM: Artificial Sequence
<220> FEATURE:
<223> OTHER INFORMATION: KASP primer

<400> SEQUENCE: 5
gaaggtgacc aagttcatgc ttaagagaca ccctggtgga aaga                    44

<210> SEQ ID NO 6
<211> LENGTH: 28
<212> TYPE: DNA
<213> ORGANISM: Artificial Sequence
<220> FEATURE:
<223> OTHER INFORMATION: KASP primer

<400> SEQUENCE: 6
tagcatcagt tccaacttgg taagcaat                                      28

<210> SEQ ID NO 7
<211> LENGTH: 44
<212> TYPE: DNA
<213> ORGANISM: Artificial Sequence

```
<220> FEATURE:
<223> OTHER INFORMATION: KASP primer

<400> SEQUENCE: 7
gaaggtgacc aagttcatgc tgaacacgta agcagaccaa gcag            44

<210> SEQ ID NO 8
<211> LENGTH: 25
<212> TYPE: DNA
<213> ORGANISM: Artificial Sequence
<220> FEATURE:
<223> OTHER INFORMATION: KASP primer

<400> SEQUENCE: 8
ccctcttctc cctaacgaat tcctt                                 25

<210> SEQ ID NO 9
<211> LENGTH: 44
<212> TYPE: DNA
<213> ORGANISM: Artificial Sequence
<220> FEATURE:
<223> OTHER INFORMATION: KASP primer

<400> SEQUENCE: 9
gaaggtgacc aagttcatgc tgaggaacct gttgctgctg atga            44

<210> SEQ ID NO 10
<211> LENGTH: 26
<212> TYPE: DNA
<213> ORGANISM: Artificial Sequence
<220> FEATURE:
<223> OTHER INFORMATION: KASP primer

<400> SEQUENCE: 10
gcgatcctag cacaaagttg aaggta                                26

<210> SEQ ID NO 11
<211> LENGTH: 44
<212> TYPE: DNA
<213> ORGANISM: Artificial Sequence
<220> FEATURE:
<223> OTHER INFORMATION: KASP primer

<400> SEQUENCE: 11
gaaggtgacc aagttcatgc tggatggatc gcttacctct tcgt            44

<210> SEQ ID NO 12
<211> LENGTH: 25
<212> TYPE: DNA
<213> ORGANISM: Artificial Sequence
<220> FEATURE:
<223> OTHER INFORMATION: KASP primer

<400> SEQUENCE: 12
cagggtaagg ttgtcctgta acgtt                                 25

<210> SEQ ID NO 13
<211> LENGTH: 42
<212> TYPE: DNA
<213> ORGANISM: Artificial Sequence
<220> FEATURE:
<223> OTHER INFORMATION: KASP primer

<400> SEQUENCE: 13
gaaggtgacc aagttcatgc tctattggat ggggactcaa gc              42
```

```
<210> SEQ ID NO 14
<211> LENGTH: 26
<212> TYPE: DNA
<213> ORGANISM: Artificial Sequence
<220> FEATURE:
<223> OTHER INFORMATION: KASP primer

<400> SEQUENCE: 14
gggagatcct tagtagcaga agagat                                         26

<210> SEQ ID NO 15
<211> LENGTH: 44
<212> TYPE: DNA
<213> ORGANISM: Artificial Sequence
<220> FEATURE:
<223> OTHER INFORMATION: KASP primer

<400> SEQUENCE: 15
gaaggtgacc aagttcatgc tcctgagagg cgtcctgttg aaat                     44

<210> SEQ ID NO 16
<211> LENGTH: 25
<212> TYPE: DNA
<213> ORGANISM: Artificial Sequence
<220> FEATURE:
<223> OTHER INFORMATION: KASP primer

<400> SEQUENCE: 16
aacagcagcc atatcagcag cagta                                          25

<210> SEQ ID NO 17
<211> LENGTH: 49
<212> TYPE: DNA
<213> ORGANISM: Artificial Sequence
<220> FEATURE:
<223> OTHER INFORMATION: KASP primer N57 X

<400> SEQUENCE: 17
gaaggtgacc aagttcatgc tgccttcagt ttaaactatc agtgtttga                49

<210> SEQ ID NO 18
<211> LENGTH: 47
<212> TYPE: DNA
<213> ORGANISM: Artificial Sequence
<220> FEATURE:
<223> OTHER INFORMATION: KASP primer N57 Y

<400> SEQUENCE: 18
gaaggtcgga gtcaacggat tgttctgtat acaacttgtc gtgctac                  47

<210> SEQ ID NO 19
<211> LENGTH: 25
<212> TYPE: DNA
<213> ORGANISM: Artificial Sequence
<220> FEATURE:
<223> OTHER INFORMATION: KASP primer N57 Common

<400> SEQUENCE: 19
gggttgtgtg aaaacgtgtg agcaa                                          25

<210> SEQ ID NO 20
<211> LENGTH: 45
<212> TYPE: DNA
<213> ORGANISM: Artificial Sequence
<220> FEATURE:
<223> OTHER INFORMATION: KASP primer N68 X
```

```
<400> SEQUENCE: 20
gaaggtgacc aagttcatgc taaactatca gtgtttgaac acctc                45

<210> SEQ ID NO 21
<211> LENGTH: 44
<212> TYPE: DNA
<213> ORGANISM: Artificial Sequence
<220> FEATURE:
<223> OTHER INFORMATION: KASP primer N68 Y

<400> SEQUENCE: 21
gaaggtcgga gtcaacggat tacaacttgt cgtgctacac acct                 44

<210> SEQ ID NO 22
<211> LENGTH: 24
<212> TYPE: DNA
<213> ORGANISM: Artificial Sequence
<220> FEATURE:
<223> OTHER INFORMATION: KASP primer N68 Common

<400> SEQUENCE: 22
gacaagtgaa tctgtttggg gttg                                       24

<210> SEQ ID NO 23
<211> LENGTH: 49
<212> TYPE: DNA
<213> ORGANISM: Artificial Sequence
<220> FEATURE:
<223> OTHER INFORMATION: KASP primer N58 X

<400> SEQUENCE: 23
gaaggtgacc aagttcatgc tgccttcagt ttaaactatc agtgtttga            49

<210> SEQ ID NO 24
<211> LENGTH: 47
<212> TYPE: DNA
<213> ORGANISM: Artificial Sequence
<220> FEATURE:
<223> OTHER INFORMATION: KASP primer N58 Y

<400> SEQUENCE: 24
gaaggtcgga gtcaacggat tgttctgtat acaacttgtc gtgctac              47

<210> SEQ ID NO 25
<211> LENGTH: 27
<212> TYPE: DNA
<213> ORGANISM: Artificial Sequence
<220> FEATURE:
<223> OTHER INFORMATION: KASP primer N58 Common

<400> SEQUENCE: 25
gaaaacgtgt gagcaattgt tggaggt                                    27

<210> SEQ ID NO 26
<211> LENGTH: 49
<212> TYPE: DNA
<213> ORGANISM: Artificial Sequence
<220> FEATURE:
<223> OTHER INFORMATION: KASP primer N85 X

<400> SEQUENCE: 26
gaaggtgacc aagttcatgc tgccttcagt ttaaactatc agtgtttga            49

<210> SEQ ID NO 27
```

```
<211> LENGTH: 47
<212> TYPE: DNA
<213> ORGANISM: Artificial Sequence
<220> FEATURE:
<223> OTHER INFORMATION: KASP primer N85 Y

<400> SEQUENCE: 27
gaaggtcgga gtcaacggat tgttctgtat acaacttgtc gtgctac                47

<210> SEQ ID NO 28
<211> LENGTH: 24
<212> TYPE: DNA
<213> ORGANISM: Artificial Sequence
<220> FEATURE:
<223> OTHER INFORMATION: KASP primer N85 Common

<400> SEQUENCE: 28
gacaagtgaa tctgtttggg gttg                                         24

<210> SEQ ID NO 29
<211> LENGTH: 44
<212> TYPE: DNA
<213> ORGANISM: Artificial Sequence
<220> FEATURE:
<223> OTHER INFORMATION: KASP primer N14 X

<400> SEQUENCE: 29
gaaggtcgga gtcaacggat tacaacttgt cgtgctacac acct                   44

<210> SEQ ID NO 30
<211> LENGTH: 46
<212> TYPE: DNA
<213> ORGANISM: Artificial Sequence
<220> FEATURE:
<223> OTHER INFORMATION: KASP primer N14 Y

<400> SEQUENCE: 30
gaaggtgacc aagttcatgc taaactatca gtgtttgaac acctcc                 46

<210> SEQ ID NO 31
<211> LENGTH: 22
<212> TYPE: DNA
<213> ORGANISM: Artificial Sequence
<220> FEATURE:
<223> OTHER INFORMATION: KASP primer

<400> SEQUENCE: 31
ggttgtgtga aaacgtgtga gc                                           22

<210> SEQ ID NO 32
<211> LENGTH: 41
<212> TYPE: DNA
<213> ORGANISM: Artificial Sequence
<220> FEATURE:
<223> OTHER INFORMATION: KASP primer

<400> SEQUENCE: 32
gaaggtcgga gtcaacggat ttgtgagcaa ttgttggagg t                      41

<210> SEQ ID NO 33
<211> LENGTH: 40
<212> TYPE: DNA
<213> ORGANISM: Artificial Sequence
<220> FEATURE:
<223> OTHER INFORMATION: KASP primer

<400> SEQUENCE: 33
```

```
gaaggtgacc aagttcatgc tttgtgattc cgggcagtag                    40
```

<210> SEQ ID NO 34
<211> LENGTH: 31
<212> TYPE: DNA
<213> ORGANISM: Artificial Sequence
<220> FEATURE:
<223> OTHER INFORMATION: KASP primer

<400> SEQUENCE: 34

```
tcttatcaac attaagaaca taatctttta g                             31
```

<210> SEQ ID NO 35
<211> LENGTH: 49
<212> TYPE: DNA
<213> ORGANISM: Artificial Sequence
<220> FEATURE:
<223> OTHER INFORMATION: KASP primer N62 Downstream A02 X

<400> SEQUENCE: 35

```
gaaggtgacc aagttcatgc ttttagctaa ataagaggtt ctgtatact          49
```

<210> SEQ ID NO 36
<211> LENGTH: 51
<212> TYPE: DNA
<213> ORGANISM: Artificial Sequence
<220> FEATURE:
<223> OTHER INFORMATION: KASP primer N62 Y

<400> SEQUENCE: 36

```
gaaggtcgga gtcaacggat tcttttagct aaataagagg ttctgtatac a       51
```

<210> SEQ ID NO 37
<211> LENGTH: 24
<212> TYPE: DNA
<213> ORGANISM: Artificial Sequence
<220> FEATURE:
<223> OTHER INFORMATION: KASP primer N62 Common

<400> SEQUENCE: 37

```
cagggattgt gattccgggc agta                                     24
```

<210> SEQ ID NO 38
<211> LENGTH: 26
<212> TYPE: DNA
<213> ORGANISM: Artificial Sequence
<220> FEATURE:
<223> OTHER INFORMATION: KASP primer N62 Common2

<400> SEQUENCE: 38

```
gtgtgagcaa ttgttggagg tgtgta                                   26
```

<210> SEQ ID NO 39
<211> LENGTH: 52
<212> TYPE: DNA
<213> ORGANISM: Artificial Sequence
<220> FEATURE:
<223> OTHER INFORMATION: KASP primer N64 X

<400> SEQUENCE: 39

```
gaaggtgacc aagttcatgc tccgggcagt agtaattaat aatatagtat ta     52
```

<210> SEQ ID NO 40
<211> LENGTH: 44
<212> TYPE: DNA

```
<213> ORGANISM: Artificial Sequence
<220> FEATURE:
<223> OTHER INFORMATION: KASP primer N64 Y

<400> SEQUENCE: 40
gaaggtcgga gtcaacggat tggaggtgtg tagcacgaca agtt                44

<210> SEQ ID NO 41
<211> LENGTH: 30
<212> TYPE: DNA
<213> ORGANISM: Artificial Sequence
<220> FEATURE:
<223> OTHER INFORMATION: KASP primer N64 Common

<400> SEQUENCE: 41
ctcaaacttc ttatcaacat taagaacata                                30

<210> SEQ ID NO 42
<211> LENGTH: 48
<212> TYPE: DNA
<213> ORGANISM: Artificial Sequence
<220> FEATURE:
<223> OTHER INFORMATION: KASP primer N52 X

<400> SEQUENCE: 42
gaaggtgacc aagttcatgc tgccttcagt ttaaactatc agtgtttg            48

<210> SEQ ID NO 43
<211> LENGTH: 41
<212> TYPE: DNA
<213> ORGANISM: Artificial Sequence
<220> FEATURE:
<223> OTHER INFORMATION: KASP primer N52 Y

<400> SEQUENCE: 43
gaaggtcgga gtcaacggat tcacggtgga ggtcaccatg t                   41

<210> SEQ ID NO 44
<211> LENGTH: 24
<212> TYPE: DNA
<213> ORGANISM: Artificial Sequence
<220> FEATURE:
<223> OTHER INFORMATION: KASP primer N52 Common

<400> SEQUENCE: 44
cacggagata ggctgcatct gaat                                      24

<210> SEQ ID NO 45
<211> LENGTH: 48
<212> TYPE: DNA
<213> ORGANISM: Artificial Sequence
<220> FEATURE:
<223> OTHER INFORMATION: KASP primer N51 X

<400> SEQUENCE: 45
gaaggtgacc aagttcatgc tgccttcagt ttaaactatc agtgtttg            48

<210> SEQ ID NO 46
<211> LENGTH: 41
<212> TYPE: DNA
<213> ORGANISM: Artificial Sequence
<220> FEATURE:
<223> OTHER INFORMATION: KASP primer N51 Y

<400> SEQUENCE: 46
gaaggtcgga gtcaacggat tcacggtgga ggtcaccatg t                   41
```

<210> SEQ ID NO 47
<211> LENGTH: 25
<212> TYPE: DNA
<213> ORGANISM: Artificial Sequence
<220> FEATURE:
<223> OTHER INFORMATION: KASP primer N51 Common

<400> SEQUENCE: 47
gctgcatctg aatgactggt gtgtt                                    25

<210> SEQ ID NO 48
<211> LENGTH: 45
<212> TYPE: DNA
<213> ORGANISM: Artificial Sequence
<220> FEATURE:
<223> OTHER INFORMATION: KASP primer N09 X

<400> SEQUENCE: 48
gaaggtcgga gtcaacggat tgtgttcttg ggtgggtctg tcctt              45

<210> SEQ ID NO 49
<211> LENGTH: 45
<212> TYPE: DNA
<213> ORGANISM: Artificial Sequence
<220> FEATURE:
<223> OTHER INFORMATION: KASP primer N09 Y

<400> SEQUENCE: 49
gaaggtgacc aagttcatgc ttgttcttgg gtgggtctgt ccttc              45

<210> SEQ ID NO 50
<211> LENGTH: 25
<212> TYPE: DNA
<213> ORGANISM: Artificial Sequence
<220> FEATURE:
<223> OTHER INFORMATION: KASP primer

<400> SEQUENCE: 50
atccactagc agattgtcgt ttccc                                    25

<210> SEQ ID NO 51
<211> LENGTH: 22
<212> TYPE: DNA
<213> ORGANISM: Artificial Sequence
<220> FEATURE:
<223> OTHER INFORMATION: KASP primer

<400> SEQUENCE: 51
gttggctaag gtcacggtgg ag                                       22

<210> SEQ ID NO 52
<211> LENGTH: 42
<212> TYPE: DNA
<213> ORGANISM: Artificial Sequence
<220> FEATURE:
<223> OTHER INFORMATION: KASP primer N50 X

<400> SEQUENCE: 52
gaaggtgacc aagttcatgc ttcttgggtg ggtctgtcct tc                 42

<210> SEQ ID NO 53
<211> LENGTH: 44
<212> TYPE: DNA
<213> ORGANISM: Artificial Sequence
<220> FEATURE:

<223> OTHER INFORMATION: KASP primer N50 Y

<400> SEQUENCE: 53
gaaggtcgga gtcaacggat tgttcttggg tgggtctgtc ctta     44

<210> SEQ ID NO 54
<211> LENGTH: 25
<212> TYPE: DNA
<213> ORGANISM: Artificial Sequence
<220> FEATURE:
<223> OTHER INFORMATION: KASP primer N50 A05 Common

<400> SEQUENCE: 54
gattgtcgtt tcccgccttc agttt     25

<210> SEQ ID NO 55
<211> LENGTH: 22
<212> TYPE: DNA
<213> ORGANISM: Artificial Sequence
<220> FEATURE:
<223> OTHER INFORMATION: KASP primer N50 Common2

<400> SEQUENCE: 55
cgttggctaa ggtcacggtg ga     22

<210> SEQ ID NO 56
<211> LENGTH: 42
<212> TYPE: DNA
<213> ORGANISM: Artificial Sequence
<220> FEATURE:
<223> OTHER INFORMATION: KASP primer N48 X

<400> SEQUENCE: 56
gaaggtgacc aagttcatgc ttcttgggtg ggtctgtcct tc     42

<210> SEQ ID NO 57
<211> LENGTH: 44
<212> TYPE: DNA
<213> ORGANISM: Artificial Sequence
<220> FEATURE:
<223> OTHER INFORMATION: KASP primer N48 Y

<400> SEQUENCE: 57
gaaggtcgga gtcaacggat tgttcttggg tgggtctgtc ctta     44

<210> SEQ ID NO 58
<211> LENGTH: 28
<212> TYPE: DNA
<213> ORGANISM: Artificial Sequence
<220> FEATURE:
<223> OTHER INFORMATION: KASP primer N48 Common

<400> SEQUENCE: 58
ccgccttcag tttaaactat cagtgttt     28

<210> SEQ ID NO 59
<211> LENGTH: 22
<212> TYPE: DNA
<213> ORGANISM: Artificial Sequence
<220> FEATURE:
<223> OTHER INFORMATION: KASP primer N48 Common 2

<400> SEQUENCE: 59
cgttggctaa ggtcacggtg ga     22

-continued

```
<210> SEQ ID NO 60
<211> LENGTH: 41
<212> TYPE: DNA
<213> ORGANISM: Artificial Sequence
<220> FEATURE:
<223> OTHER INFORMATION: KASP primer N10 X

<400> SEQUENCE: 60
gaaggtcgga gtcaacggat tggtcacggt ggaggtcacc a                 41

<210> SEQ ID NO 61
<211> LENGTH: 48
<212> TYPE: DNA
<213> ORGANISM: Artificial Sequence
<220> FEATURE:
<223> OTHER INFORMATION: KASP primer N10 Y

<400> SEQUENCE: 61
gaaggtgacc aagttcatgc tccgccttca gtttaaacta tcagtgtt         48

<210> SEQ ID NO 62
<211> LENGTH: 22
<212> TYPE: DNA
<213> ORGANISM: Artificial Sequence
<220> FEATURE:
<223> OTHER INFORMATION: KASP primer

<400> SEQUENCE: 62
ggtgtgttct tgggtgggtc tg                                     22

<210> SEQ ID NO 63
<211> LENGTH: 46
<212> TYPE: DNA
<213> ORGANISM: Artificial Sequence
<220> FEATURE:
<223> OTHER INFORMATION: KASP primer N83 X

<400> SEQUENCE: 63
gaaggtgacc aagttcatgc ttcagtttaa actatcagtg ttacct           46

<210> SEQ ID NO 64
<211> LENGTH: 41
<212> TYPE: DNA
<213> ORGANISM: Artificial Sequence
<220> FEATURE:
<223> OTHER INFORMATION: KASP primer N83 Y

<400> SEQUENCE: 64
gaaggtcgga gtcaacggat tacatggtga cctccaccgt g                41

<210> SEQ ID NO 65
<211> LENGTH: 26
<212> TYPE: DNA
<213> ORGANISM: Artificial Sequence
<220> FEATURE:
<223> OTHER INFORMATION: KASP primer N83 Common

<400> SEQUENCE: 65
gtactttaag cttataaccc tttgtc                                 26

<210> SEQ ID NO 66
<211> LENGTH: 46
<212> TYPE: DNA
<213> ORGANISM: Artificial Sequence
<220> FEATURE:
<223> OTHER INFORMATION: KASP primer N82 X
```

```
<400> SEQUENCE: 66
gaaggtgacc aagttcatgc tggagatcca ctagcagatt gtcgtt        46

<210> SEQ ID NO 67
<211> LENGTH: 42
<212> TYPE: DNA
<213> ORGANISM: Artificial Sequence
<220> FEATURE:
<223> OTHER INFORMATION: KASP primer N82 Y

<400> SEQUENCE: 67
gaaggtcgga gtcaacggat tcttgggtgg gtctgtcctt ac            42

<210> SEQ ID NO 68
<211> LENGTH: 23
<212> TYPE: DNA
<213> ORGANISM: Artificial Sequence
<220> FEATURE:
<223> OTHER INFORMATION: KASP primer N62 Common

<400> SEQUENCE: 68
gcaggaggta ctttaagctt ata                                 23

<210> SEQ ID NO 69
<211> LENGTH: 46
<212> TYPE: DNA
<213> ORGANISM: Artificial Sequence
<220> FEATURE:
<223> OTHER INFORMATION: KASP primer N84 X

<400> SEQUENCE: 69
gaaggtgacc aagttcatgc tgattgtcgt ttcccgcctt cagttt        46

<210> SEQ ID NO 70
<211> LENGTH: 43
<212> TYPE: DNA
<213> ORGANISM: Artificial Sequence
<220> FEATURE:
<223> OTHER INFORMATION: KASP primer N84 Y

<400> SEQUENCE: 70
gaaggtcgga gtcaacggat tgtccttaca tggtgacctc cac           43

<210> SEQ ID NO 71
<211> LENGTH: 26
<212> TYPE: DNA
<213> ORGANISM: Artificial Sequence
<220> FEATURE:
<223> OTHER INFORMATION: KASP primer N84 Common

<400> SEQUENCE: 71
gtactttaag cttataaccc tttgtc                              26

<210> SEQ ID NO 72
<211> LENGTH: 46
<212> TYPE: DNA
<213> ORGANISM: Artificial Sequence
<220> FEATURE:
<223> OTHER INFORMATION: KASP primer N66 X

<400> SEQUENCE: 72
gaaggtgacc aagttcatgc tgattgtcgt ttcccgcctt cagttt        46

<210> SEQ ID NO 73
<211> LENGTH: 43
```

<210> SEQ ID NO 73
<211> LENGTH: 43
<212> TYPE: DNA
<213> ORGANISM: Artificial Sequence
<220> FEATURE:
<223> OTHER INFORMATION: KASP primer N66 Y

<400> SEQUENCE: 73
gaaggtcgga gtcaacggat tgtccttaca tggtgacctc cac    43

<210> SEQ ID NO 74
<211> LENGTH: 23
<212> TYPE: DNA
<213> ORGANISM: Artificial Sequence
<220> FEATURE:
<223> OTHER INFORMATION: KASP primer N66 Common

<400> SEQUENCE: 74
gcaggaggta ctttaagctt ata    23

<210> SEQ ID NO 75
<211> LENGTH: 47
<212> TYPE: DNA
<213> ORGANISM: Artificial Sequence
<220> FEATURE:
<223> OTHER INFORMATION: KASP primer N41 X

<400> SEQUENCE: 75
gaaggtgacc aagttcatgc tttttattc aaccgttggc taaggta    47

<210> SEQ ID NO 76
<211> LENGTH: 46
<212> TYPE: DNA
<213> ORGANISM: Artificial Sequence
<220> FEATURE:
<223> OTHER INFORMATION: KASP primer N41 Y

<400> SEQUENCE: 76
gaaggtcgga gtcaacggat tttttattca accgttggct aaggtc    46

<210> SEQ ID NO 77
<211> LENGTH: 25
<212> TYPE: DNA
<213> ORGANISM: Artificial Sequence
<220> FEATURE:
<223> OTHER INFORMATION: KASP primer N41 Common

<400> SEQUENCE: 77
gattgtcgtt tcccgccttc agttt    25

<210> SEQ ID NO 78
<211> LENGTH: 25
<212> TYPE: DNA
<213> ORGANISM: Artificial Sequence
<220> FEATURE:
<223> OTHER INFORMATION: KASP primer N41 Common2

<400> SEQUENCE: 78
ttcttgggtg ggtctgtcct tacat    25

<210> SEQ ID NO 79
<211> LENGTH: 47
<212> TYPE: DNA
<213> ORGANISM: Artificial Sequence
<220> FEATURE:
<223> OTHER INFORMATION: KASP primer N43 X

<400> SEQUENCE: 79

```
gaaggtgacc aagttcatgc tttttattc aaccgttggc taaggta                47
```

<210> SEQ ID NO 80
<211> LENGTH: 46
<212> TYPE: DNA
<213> ORGANISM: Artificial Sequence
<220> FEATURE:
<223> OTHER INFORMATION: KASP primer N43 Y

<400> SEQUENCE: 80

```
gaaggtcgga gtcaacggat tttttattca accgttggct aaggtc                46
```

<210> SEQ ID NO 81
<211> LENGTH: 25
<212> TYPE: DNA
<213> ORGANISM: Artificial Sequence
<220> FEATURE:
<223> OTHER INFORMATION: KASP primer N43 Common

<400> SEQUENCE: 81

```
ggagatccac tagcagattg tcgtt                                       25
```

<210> SEQ ID NO 82
<211> LENGTH: 25
<212> TYPE: DNA
<213> ORGANISM: Artificial Sequence
<220> FEATURE:
<223> OTHER INFORMATION: KASP primer N43 Common2

<400> SEQUENCE: 82

```
ttcttgggtg ggtctgtcct tacat                                       25
```

<210> SEQ ID NO 83
<211> LENGTH: 51
<212> TYPE: DNA
<213> ORGANISM: Artificial Sequence
<220> FEATURE:
<223> OTHER INFORMATION: KASP primer

<400> SEQUENCE: 83

```
gaaggtgacc aagttcatgc tcttttagct aaataagagg ttctgtatac t          51
```

<210> SEQ ID NO 84
<211> LENGTH: 51
<212> TYPE: DNA
<213> ORGANISM: Artificial Sequence
<220> FEATURE:
<223> OTHER INFORMATION: KASP primer

<400> SEQUENCE: 84

```
gaaggtcgga gtcaacggat tcttttagct aaataagagg ttctgtatac a          51
```

<210> SEQ ID NO 85
<211> LENGTH: 19
<212> TYPE: DNA
<213> ORGANISM: Artificial Sequence
<220> FEATURE:
<223> OTHER INFORMATION: KASP primer

<400> SEQUENCE: 85

```
gattgtgatt ccgggcagt                                              19
```

<210> SEQ ID NO 86
<211> LENGTH: 21
<212> TYPE: DNA
<213> ORGANISM: Artificial Sequence

```
<220> FEATURE:
<223> OTHER INFORMATION: KASP primer

<400> SEQUENCE: 86
gtgtgaaaac gtgtgagcaa t                                              21

<210> SEQ ID NO 87
<211> LENGTH: 49
<212> TYPE: DNA
<213> ORGANISM: Artificial Sequence
<220> FEATURE:
<223> OTHER INFORMATION: KASP primer

<400> SEQUENCE: 87
gaaggtgacc aagttcatgc tacttttttt tcaactgttg gctaaggta                49

<210> SEQ ID NO 88
<211> LENGTH: 49
<212> TYPE: DNA
<213> ORGANISM: Artificial Sequence
<220> FEATURE:
<223> OTHER INFORMATION: KASP primer

<400> SEQUENCE: 88
gaaggtcgga gtcaacggat tacttttttt tcaactgttg gctaaggtc                49

<210> SEQ ID NO 89
<211> LENGTH: 21
<212> TYPE: DNA
<213> ORGANISM: Artificial Sequence
<220> FEATURE:
<223> OTHER INFORMATION: KASP primer

<400> SEQUENCE: 89
gtgtgttctt gggtgggtct g                                              21

<210> SEQ ID NO 90
<211> LENGTH: 21
<212> TYPE: DNA
<213> ORGANISM: Artificial Sequence
<220> FEATURE:
<223> OTHER INFORMATION: KASP primer

<400> SEQUENCE: 90
gtcgtttccc gccttcagtt t                                              21
```

INBRED TRANSGENIC CANOLA LINE NS-B50027-4 AND SEEDS THEREOF

RELATED APPLICATIONS

This Application is a continuation of U.S. application Ser. No. 16/792,046, filed Feb. 14, 2020, now abandoned, which is a continuation of U.S. application Ser. No. 15/626,019, filed Jun. 16, 2017, now U.S. Pat. No. 10,563,218, and which claims priority benefit of U.S. Provisional Application No. 62/351,250, filed Jun. 16, 2016, the contents of which are incorporated fully herein by reference in their entireties for all purposes.

SEQUENCE LISTING

The instant application contains a Sequence Listing entitled "87376.0003US2 ST25.txt," 17,000 bytes and created Feb. 8, 2022, which has been submitted in ASCII format via EFS-Web and is incorporated herein by reference in its entirety.

FIELD

The present embodiments relate to the field of canola breeding and agricultural products, specifically to the inbred seed and plant of inbred transgenic canola line designated NS-B50027-4, and derivatives of such inbred plant; and methods of detecting inbred transgenic canola line NS-B50027-4.

BACKGROUND

Canola is an important oil crop in many areas of the world. The fatty acid composition of canola oil is rich in both mono-unsaturated and polyunsaturated fatty acids including short chain omega-3, but lacks in long-chain omega-3 fatty acids. Long chain omega-3 (LC-ω3) fatty acids have established health benefits, but currently LC-ω3 fatty acids are obtained primarily from algae directly or from algae-eating ocean fish. Recognition of the dietary importance of LC-ω3 fatty acids, especially docosahexaenoic acid (22:6 n-3; DHA), docosapentaenoic acid (22:5 n-3; DPA) and eicosapentaenoic acid (20:5 n-3; EPA), has contributed to a dramatic increase in the demand for consumable fish oil. Thus, there is a need for alternative, direct sources of LC-ω3 fatty acids for human consumption. Additionally, because farmed fish, such as Atlantic salmon, accumulate fatty acids in proportion to dietary fatty acids, there is a need to sustain the amount of LC-polyunsaturated fatty acids (LC-PUFA) in fish feed, and in turn ensure the presence of these fatty acids in farmed fish. Accordingly, there is a need for LC-PUFA-rich sources that can be used in aquaculture. For example, there is a need for canola that can produce LC-PUFA, particularly LC-ω3 fatty acid such as DHA, for use in aquaculture as well as for direct human consumption. Despite achievements in plant breeding and manipulation by molecular genetics, however, there are no commercial sources of canola oil that approach the content of LC-PUFA produced in wild fishes. Further, a canola cultivar (not an F1 hybrid) should be homogenous, homozygous, and reproducible to be useful for the reliable production of a commercial crop. Therefore, there remains a need for a canola line that can be grown as a sustainable crop, the seeds of which provide commercially viable amounts of ω3 fatty acids, LC-PUFA, and LC-ω3 fatty acids such as DHA.

SUMMARY

The embodiments described herein provide an inbred recombinant canola line, designated NS-B50027-4, the seeds of which comprise advantageous levels of ω3 and LC-ω3 fatty acid, thus providing a renewable, land-based system to produce these valuable oils. A representative sample of seeds of inbred canola line NS-B50027-4 was deposited according to the Budapest Treaty at the American Type Culture Collection (ATCC®) (Manassas, VA) on Jun. 9, 2016, and assigned Accession Number PTA-123186 (see Appendix A). Also described herein are cells, tissues, seeds, and oil of inbred canola line NS-B50027-4. The combination of selection and breeding with transgenic manipulation enables variation in a species where that variation does not exist. For example, the fatty acid profile of canola line NS-B50027-4 described herein does not exist in native plants such as B. napus; and the traits described herein, particularly the advantageous trait of producing DHA, were developed with significant technical intervention by man.

An aspect of the present embodiments provides seed of canola (*Brassica napus* L.) line NS-B50027-4, a genetically modified canola of cultivar AV Jade that was selected and bred to a stable, uniform breeding line that accumulates in its seeds a high proportion (weight percent) of ω3 and LC-ω3 fatty acids, particularly LC-ω3 PUFA such as DHA, relative to the total fatty acid content. Inbred line NS-B50027-4 was developed to provide canola plants that produce seeds comprising LC-ω3 PUFA, particularly DHA, at levels approaching those found in some wild fish oil. Edible oil derived from NS-B50027-4 has significantly higher DHA content than other *B. napus* plants. The novel, uniform breeding line NS-B50027-4 was developed by initial genetic transformation followed by rigorous selection and breeding for the high DHA trait in a stable, high-yielding, morphologically fit canola line.

Accordingly, at least one embodiment described herein relates to the seeds of inbred canola line NS-B50027-4; to the plants cultivated from the seeds of inbred canola line NS-B50027-4, and parts thereof, such as pollen, ovule, or seed; and to methods for producing seed from a canola plant by cultivating inbred canola line NS-B50027-4, or by crossing inbred canola line NS-B50027-4 with itself or with another canola or *Brassica* line (such as *B. juncea*), and obtaining seed from the cultivated progeny. A related embodiment provides seed from a canola or *Brassica* line derived from NS-B50027-4 by introgression of at least one transgenic locus of NS-B50027-4.

At least one embodiment provides seed from a population of canola plants produced by the method described herein, said population deriving, on average, 10% to 100% of its alleles from canola line NS-B50027-4. Similarly, the present embodiments provide use of canola line NS-B50027-4, a sub-line of NS-B50027-4, progeny of NS-B50027-4 or the sub-line, or a plant produced by crossing NS-B50027-4 with a second canola or *Brassica* plant, for breeding or for cultivating a plant for seed, oil, meal, or protein production.

At least one embodiment provides a seed of an oilseed rape plant, such as a *Brassica napus* plant, comprising in its genome at least a portion of the genome of inbred line NS-B50027-4. At least one embodiment provides a plant, such as a *B. napus* or *B. juncea* plant, comprising in its genome at least a portion of the genome of inbred line NS-B50027-4. At least one embodiment provides a cell of an oilseed rape plant, such as a *B. napus* or *B. juncea* plant, comprising in its genome at least a portion of the genome of inbred line NS-B50027-4. Another embodiment provides genomic DNA of an oilseed rape plant, such as a *B. napus* or *B. juncea* plant, comprising at least a portion of the genome, e.g., at least one transgenic locus, of line NS-B50027-4. At least one embodiment further relates to seeds, cells, tissues, tissue cultures, progeny, and descendants from a plant comprising at least a portion of the genome of NS-B50027-4 grown from seed deposited at the ATCC® having Accession No. PTA-123186. Another embodiment further provides plants obtainable from (such as by propagation of or breeding with) a canola plant comprising at least a portion of the genome of NS-B50027-4 (such as a plant grown from the seed deposited at the ATCC® having Accession No. PTA-123186).

Reference seed of inbred line NS-B50027-4 of the present embodiments has been deposited with ATCC® under Accession No. PTA-123186. At least one embodiment provides the seed of NS-B50027-4 deposited as accession number PTA-123186, which grows into a canola plant the seed of which, at conventional harvest, comprises at least about 5% DHA, about 6% DHA, about 7% DHA, about 8% DHA, about 9% DHA, about 10% DHA, about 11% DHA, about 12% DHA, about 13% DHA, about 14% DHA, about 15% DHA, 16% DHA, inclusive of amounts in-between and at recited values, or more DHA, as weight percent (wt. %) of the total fatty acids of the seed.

In at least one embodiment, the seed of ATCC® deposit Accession No. PTA-123186 is a seed lot consisting of at least about 95% inbred transgenic seeds having the transgenes of elite event of NS-B50027-4, that grow into a canola plant the seed of that comprises at least 5% DHA, about 6% DHA, about 7% DHA, about 8% DHA, about 9% DHA, about 10% DHA, about 11% DHA, about 12% DHA, about 13% DHA, about 14% DHA, about 15% DHA, about 16% DHA, inclusive, or more DHA, as wt. % of the total fatty acids of the seed.

The seed of ATCC® Accession No. PTA-123186 is a seed lot consisting of about 95% or more than 95% transgenic seed that is homozygous for transgene DNA comprising the elite event of NS-B50027-4, and that grow into canola plants the seed of which includes at least about 5% LC-PUFA, about 6% LC-PUFA, about 7% LC-PUFA, about 8% LC-PUFA, about 9% LC-PUFA, about 10% LC-PUFA, about 11% LC-PUFA, about 12% LC-PUFA, about 13% LC-PUFA, about 14% LC-PUFA, about 15% LC-PUFA, about 16% LC-PUFA, about 17% LC-PUFA, about 18% LC-PUFA, about 19% LC-PUFA, about 20% LC-PUFA, inclusive, or more LC-PUFA, as the sum of EPA, DPA, and DHA wt. % of the total fatty acids of the seed. The seed or seed oil of this line may contain about 20 wt. % to about 35 wt. % LC-PUFA, inclusive.

In at least one embodiment provides a seed lot of hybrid seed obtained by crossing a male sterile canola or *Brassica* line with a second canola or *Brassica* line, both of which are homozygous for the elite event of NS-B50027-4, wherein the hybrid seed comprises at least about 5% DHA, about 6% DHA, about 7% DHA, about 8% DHA, about 9% DHA, about 10% DHA, about 11% DHA, about 12% DHA, about 13% DHA, about 14% DHA, about 15% DHA, about 16% DHA, about 17% DHA, about 18% DHA, about 19% DHA, about 20% DHA, inclusive, or more DHA as wt. % of the total fatty acids of the seed.

An aspect of the present embodiments provides seed or progeny seed obtainable or obtained from the deposited seed cultivated and crossed at least once with another canola or *Brassica* (e.g., introgression with another canola or *Brassica* plant with the same or a different genetic background), which seed can be sown and cultivated, and wherein the seed obtained from such progeny may have substantially the same seed oil phenotype (trait) as that of NS-B50027-4. In some embodiments, the relative proportions of fatty acid content in seed or seed oil of such progeny seed are similar to that of NS-B50027-4, but at higher yield than NS-B50027-4. In some embodiments, such progeny seed or seed oil may contain a higher proportion of LC-PUFA, such as EPA, DPA, or DHA, than in NS-B50027-4 seed. In some embodiments, such progeny seed may contain different proportions of non-LC-PUFA such as oleic, linoleic, palmitoleic, vaccenic, or linolenic acids, than contained in NS-B50027-4 seed or seed oil. In some embodiments, at conventional harvest the fatty acid content of NS-B50027-4-derived progeny seed comprises at least 5% DHA, about 6% DHA, about 7% DHA, about 8% DHA, about 9% DHA, about 10% DHA, about 11% DHA, about 12% DHA, about 13% DHA, about 14% DHA, about 15% DHA, about 16% DHA, about 17% DHA, about 18% DHA, about 19% DHA, about 20% DHA, about 21% DHA, about 22% DHA, about 23% DHA, about 24% DHA, about 25% DHA, about 26%, about 27% DHA, about 28% DHA, about 29% DHA, about 30% DHA, inclusive, or more DHA, as wt. % of the total fatty acids of the seed. For example, seed of such progeny may comprise between 20% to 35% DHA, inclusive, as wt. % of total fatty acids of the seed. In some embodiments, at conventional harvest the fatty acid content of such NS-B50027-4-derived progeny seed comprises at least about 5% LC-PUFA, about 6% LC-PUFA, about 7% LC-PUFA, about 8% LC-PUFA, about 9% LC-PUFA, about 10% LC-PUFA, at about 11% LC-PUFA, about 12% LC-PUFA, about 13% LC-PUFA, about 14% LC-PUFA, about 15% LC-UFA, about 16% LC-PUFA, about 17% LC-PUFA, about 18% LC-PUFA, about 19% LC-PUFA, about 20% LC-PUFA, about 21% LC-PUFA, about 22% LC-PUFA, about 23% LC-PUFA, about 24% LC-PUFA, about 25% LC-PUFA, inclusive, or more LC-PUFA, as the sum of EPA, DPA, and DHA wt. % of the total fatty acids of the seed. For example, seed of such progeny may comprise about 20% to about 40% LC-PUFA (wt. % total fatty acids), inclusive.

In at least one embodiment, the seed of NS-B50027-4 comprises substantially more ω3 ALA than conventional canola varieties. For example, at conventional harvest the fatty acid content of NS-B50027-4, or its progeny, seed comprises at least about 15% ALA, about 15% ALA, about 17% ALA, about 18% ALA, about 19% ALA, about 20% ALA, about 21% ALA, about 22% ALA, about 23% ALA, about 24% ALA, about 25% ALA, about 26% ALA, inclusive, or more ALA as wt. % of the total fatty acids of the seed.

Another aspect of the present embodiments provides oil with advantageous ω3 fatty acid and LC-ω3 fatty acid levels, in which the fatty acid content contains a higher ratio of ω3:ω6 fatty acid than that of regular commercial canola oil. For example, in one embodiment a seed oil from NS-B50027-4 has an EPA/DPA/DHA(ω3):LA(ω6) ratio of about 1.25. By comparison, seed oil from AV Jade (which contains no EPA/DPA/DHA) has a ratio of ω3:ω6 of about 0.5. Further, oil from the parent line AV Jade has no DHA, therefore no DHA:LA ratio; while an example oil from NS-B50027-4 has a DHA:LA ratio of about 1.05; compared with oil from farm-raised salmon which has a DHA:LA ratio of about 0.908. The ratios of ω3 fatty acids from NS-B50027-4 are particularly advantageous regarding palmitic acid. More specifically, oil from the parent line AV Jade has no DHA, and thus no DHA:palmitate ratio; in contrast, an example oil from NS-B50027-4 has a DHA:palmitate ratio of about 2.12; comparatively, oil from farm-raised salmon has a DHA:palmitate ratio of about 0.59, and oil from wild salmon has a DHA:palmitate ratio of about 1.02. In at least one embodiment, the ratio of ω3:ω6 fatty acid in seed oil of NS-B50027-4 is about 3 to about 7, inclusive, such as a ω3:ω6 fatty acid ratio of about 3, about 3.5, about 4, about 4.5, about 5, about 5.5, about 6, about 6.5, or about 7. Progeny, hybrid, plants derived by introgression hybridization, and other such plants derived from NS-B50027-4 have similar or advantageous ω3:ω6 ratios.

In another aspect of the present embodiments, oil, lipid, ω3-FA, LC-PUFA, or DHA from seed of inbred line NS-B50027-4, or progeny derived therefrom, is used as or in a foodstuff (food or edible material including beverages) or as nutritional supplements (food additives) for humans or animals. In at least one embodiment, oil, lipid, ω3-FA, LC-PUFA, or DHA from event NS-B50027-4 seed is used to supplement feed or feed additives for use in aquaculture. In at least one embodiment, oil, lipid, ω3-FA, LC-PUFA, or DHA from inbred line NS-B50027-4 seed is used as or in a pharmaceutical composition. In other embodiments, such oil, lipid, ω3-FA, LC-PUFA, ω3 LC-PUFA, or DHA are obtained from lines bred from NS-B50027-4.

In another aspect of the present embodiments, meal or protein derived from seed meal obtained from seed of inbred line NS-B50027-4, or progeny derived therefrom, is used as or in a foodstuff (food or edible material) or as nutritional supplements (food additives) for humans or animals. In at least one embodiment, meal processed from the seed of NS-B50027-4, or progeny derived therefrom, is used to supplement feed or feed additives for use in aquaculture. In at least one embodiment, protein processed from the seed of NS-B50027-4, or progeny derived therefrom, is used to supplement feed or feed additives for use in aquaculture.

An aspect of the present embodiments provides a method of increasing the LC-PUFA in a plant by providing (e.g., by genetic transformation or breeding) the plant with multiple copies of genetic constructs expressing some "front end" enzymes of the LC-PUFA biosynthetic pathway. For example, although not all of the enzymes Δ6-desaturases, Δ5-desaturases, Δ5-elongases, and ω3/Δ15-desaturases may be considered exclusively as the front end desaturases or elongases, in particular embodiments these genes are assembled into an artificial locus that enhances the production of LC-PUFA, such as EPA, DPA, or DHA, in a transgenic plant that expresses other genes required for synthesis of LC-PUFA. In particular embodiments, the artificial locus comprising some front end genes includes at least one of *Micromonas pusilla*-derived Δ6-desaturase, *Pyramimonas cordata*-derived Δ5-elongase, *Pavlova salina*-derived Δ5-desaturase, or *Pichia pastoris*-derived Δ15/ω3-desaturase. In particular embodiments, the artificial locus comprising some front end genes of a LC-PUFA biosynthetic pathway comprises *Micromonas pusilla*-derived Δ6-desaturase, *Pyramimonas cordata*-derived Δ5-elongase, *Pavlova salina*-derived Δ5-desaturase, and *Pichia pastoris*-derived 15/ω3-desaturase. In a particular embodiment, this four-gene transgenic insert is segregated from NS-B50027-4 (e.g., by outcrossing the A02 chromosome) and introduced into a recipient plant line using standard plant breeding techniques.

An aspect of the described embodiments provides a new canola breeding line, designated NS-B50027-4, and an oilseed rape plant, such as *Brassica napus* L., or *B. juncea*, comprising in its nuclear genome the elite event of NS-B50027-4. Canola plants comprising the genetic event of line NS-B50027-4 are capable of seed-specific production of fatty acids that contain more LC-PUFA than the fatty acids produced in conventional canola plants. Inbred canola line NS-B50027-4 plants exhibit other agronomic performance traits that are substantially equivalent to non-transgenic isogenic canola plant lines; but such traits are distinct from other lines as to provide an independent line or cultivar designated NS-B50027-4. A representative sample of inbred canola line NS-B50027-4 seeds has been deposited at the ATCC® and assigned Accession No. PTA-123186.

At least one embodiment relates to a transgenic canola seeds, plants or plant parts, tissues or cells thereof, having stably integrated into the genome at least one transgenic insert comprising an expression cassette comprising sixteen heterologous genes, the transgenes being codon-optimized for plant expression and encoding *Pavlova salina*-derived Δ4-desaturase, *Pavlova salina*-derived Δ5-desaturase, *Pyramimonas cordata*-derived Δ5-elongase, *Micromonas pusilla*-derived Δ6-desaturase, *Pyramimonas cordata*-derived Δ6-elongase, *Lachancea kluyveri*-derived Δ12-desaturase, *Pichia pastoris*-derived Δ15/ω3-desaturase, and at least one *Nicotiana tabacum*-derived matrix attachment region (MAR), and a selectable marker gene; and at least one transgenic insert comprising an expression cassette four heterologous genes, the transgenes being codon-optimized for plant expression and encoding *Micromonas pusilla*-derived Δ6-desaturase, *Pyramimonas cordata*-derived Δ5-elongase, *Pavlova salina*-derived Δ5-desaturase, *Pichia pastoris*-derived Δ15/ω3-desaturase transgenes, and a least one *Nicotiana tabacum*-derived MAR. Inbred transgenic line NS-B50027-4 exemplifies this embodiment, and a representative sample of seeds with these heterologous genes has been deposited at the ATCC®, accession number PTA-123186.

Additionally, an aspect of the present embodiments provides methods for identifying a transgenic plant, or cells or tissues thereof, comprising the transgenic feature (elite event) of inbred canola line NS-B50027-4, which method is based on identifying the presence of characterizing DNA molecules as having particular nucleotide sequences or encoding particular amino acids. For example, such characterizing DNA molecules comprise sequences of at least 15 bp, at least 20 bp, at least 30 bp, inclusive, that comprise the insertion site or junction of the event, i.e., both a part of the inserted foreign DNA comprising LC-ω3 fatty acid synthesis genes and a part of the canola genome (either the 5' or 3' flanking regions for each insertion) contiguous therewith, allowing specific identification of NS-B50027-4. As another example of this aspect, a set of primers for identification of a number of transgenes and flanking regions can be used in a method of identifying NS-B50027-4. The embodiments also relate to plants identified by the methods described herein.

Some embodiments provide compositions useful in kompetitive allele specific PCR (KASP) assays (in which two allele-specific forward primers recognize SNP), droplet digital PCR (ddPCR) assays, quantitative PCR (qPCR) assays, paralog-specific assays, and assays for adventitious presence (AP) testing. Specific embodiments of primers useful for conducting KASP assays to detect NS-B50027-4 genetic traits, particularly useful in introgression studies and hybrid development, include primers depicted in SEQ ID NO:1 to SEQ ID NO:90, or complements thereof. At least some of these primers or their complements can be included in a kit for the identification of NS-B50027-4, progeny of NS-B50027-4, or other plants or plant materials comprising at least a partial genome of NS-B50027-4.

A related aspect provides genomic DNA obtained or derived from plants, comprising at least part of the genomic DNA of line NS-B50027-4, particularly regions of the genome incorporating transgenes or junctions thereof. Such genomic DNA may be used, for example, as reference control material in the identification assays herein described.

DETAILED DESCRIPTION

Figure 1:
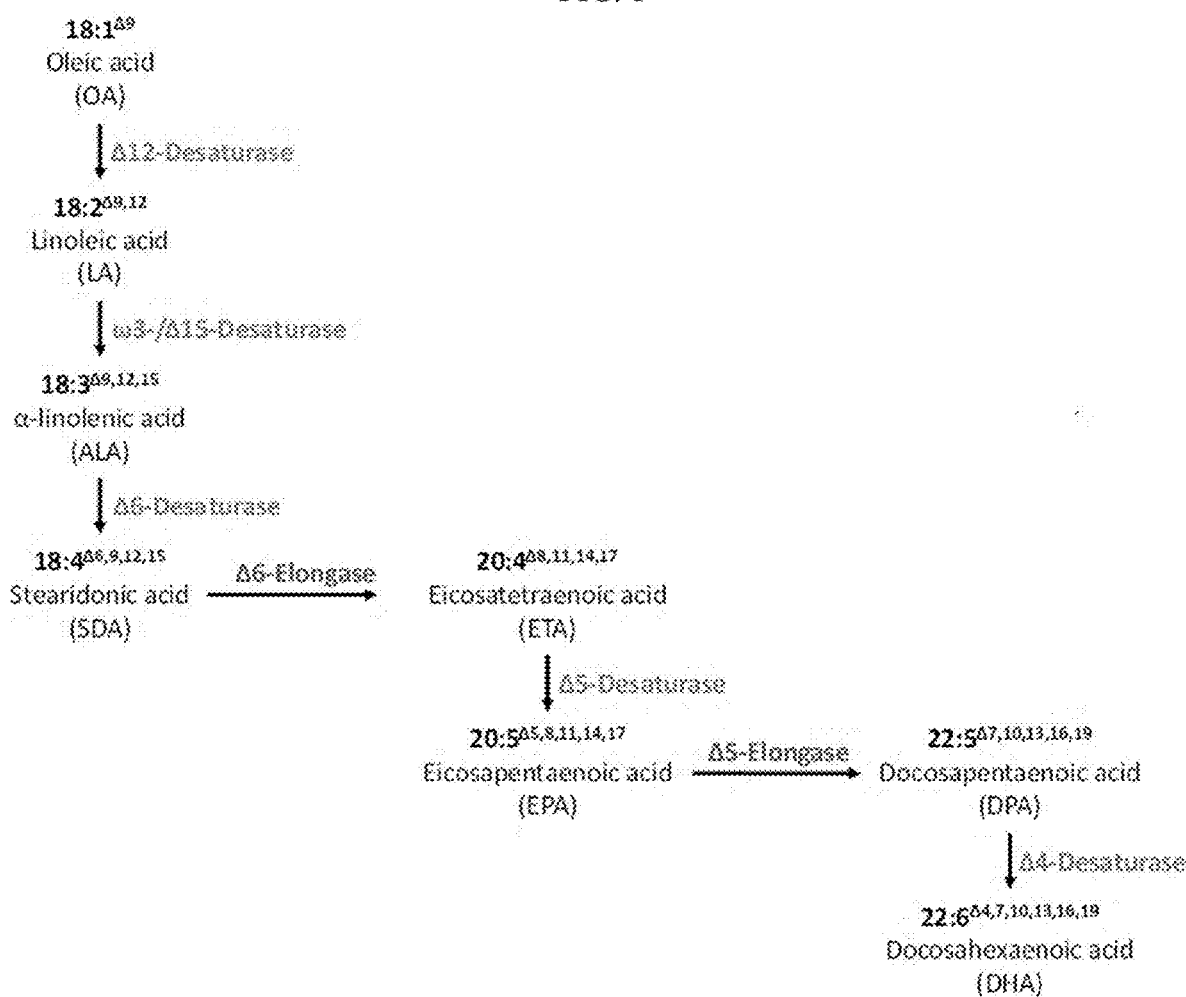
FIG. 1 is a scheme showing the enzymes that have been introduced into transgenic plants to provide the biosynthetic pathway for synthesis of DHA.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Thus, unless context indicates otherwise, the word "or" means any one member of a particular list and also includes any combination of members of that list.

All values are approximate as there is some fluctuation in fatty acid composition due to environmental conditions. Values are typically expressed as percent by weight of total fatty acid, or percent weight of the total seed. Accordingly, other than in the operating examples, or where otherwise indicated, all numbers expressing quantities or reaction conditions used herein should be understood as modified in all instances by the term "about" unless stated to the contrary; "about" refers generally to ±1% of the designated value, but may allow for ±5% or ±10% of the designated value as accepted in the relevant context by one of skill in the art.

Recombinant DNA techniques can be carried out according to standard protocols as known in the art. See, e.g., Sambrook et al., MOLECULAR CLONING: LAB. MANUAL (2nd Ed., Cold Spring Harbor Lab. Press, N Y (1989); Ausubel et al., CURRENT PROTOCOLS MOLEC. BIOL. (1994 and updates); DNA CLONING: PRACTICAL APPROACH, Vols. 1-4 (Glover & Hames, Eds., IRL Press 1995, 1996), Croy, PLANT MOLEC. BIOL. LABFAX (BIOS Sci. Pub. Ltd. & Blackwell Sci. Pub., UK, 1993); WO 2015089587.

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only, and is not intended to limit the scope of the present invention, which is defined solely by the claims. In order that the present disclosure can be more readily understood, certain terms are first defined. Additional definitions are set forth throughout the detailed description.

Definitions

A "line" is a group of plants that displays very little overall variation among individuals sharing that designation. "Line" also refers to a homogeneous assemblage of plants carrying substantially the same genetic material that display little or no genetic variation between individuals for at least one trait. "Variety" or "cultivar" may be used interchangeably with "line," but in general the former two terms refer to a line that is suitable for commercial production. "Genetically derived" as used for example in the phrase "genetically derived from the parent lines" means that the characteristic in question is dictated wholly or in part by an aspect of the genetic makeup of the plant in question.

"*Brassica*" plant as used herein refers to plants of the family of the Brassicaceae. The *Brassica* plant may belong to one of the species *Brassica napus, B. rapa* (or *campestris*), or *B. juncea*. Alternatively, the plant can belong to a species originating from intercrossing of these *Brassica* species, such as *B. napocampestris*, or of an artificial crossing of one of these *Brassica* species with another species of the Cruciferacea. Ploidy refers to whether the number of chromosomes exhibited by a cultivar is diploid or tetraploid. Because *Brassica napus* is an allotetraploid (amphidiploid) arising from the cross and retention of both genomes of *Brassica rapa* (previously *B. campestris*) and *B. oleracea*, a *Brassica napus* plant comprising transgenic event NS-B50027-4 may be used with various or conventional breeding methods to introduce the NS-B50027-4 event, and thus the "trait" of producing LC-ω3 fatty acids or increasing expression of LC-ω3 fatty acids, as described herein, into other members of the *Brassica* genus. Accordingly, examples of members of the *Brassica* genus useful in practicing the present embodiments include but are not limited to *B. juncea, B. napobrassica, B. oleracea, B. carinata, B. napus, B. rapa*, and *B. campestris*, as well as any other plants belonging to the genus *Brassica* that permit breeding between *Brassica* species. Generally, "oilseed plant" refers to any one of the species *B. napus, B. rapa* (or *campestris*), or *B. juncea*.

*Brassica napus* is commonly known as rapeseed or oilseed rape and specific cultivars may be referred to as canola. As used herein, the term "canola" or "canola plant" refers to a *Brassica* plant capable of being used to produce canola oil (i.e., an oil meeting a specific quality designation of containing less than 2% erucic acid) and includes varieties of *B. napus, B. napobrassica, B. rapa, B. juncea*, and *B. campestris*. Canola plants are amphidiploid (also called an allotetraploid), which refers to an interspecific hybrid having a complete diploid chromosome set from each parent form, typically denoted with genome AACC.

"Canola" and "canola plant" typically refers to *Brassica napus*, but includes all plant varieties that can be bred with canola. "Canola" and "canola plant" also includes plant parts. "Canola oil" must contain less than 2% erucic acid (Δ13-22:1), and less than 30 μmoles of glucosinolates/g air-dry, oil-free solid canola seed (i.e., meal). See, e.g., CODEX ALIMENTARIUS: FATS, OILS & RELATED PRODUCTS, VOL. 8 (2nd ed., Food & Agriculture Org. United Nations, Rome, Italy, 2001).

"Plant part" includes plant cells, plant organs, plant protoplasts, plant cell tissue cultures from which plants can be regenerated, plant calli, plant clumps, and plant cells that are intact in plants or parts of plants such as embryos, pollen, ovules, seeds, pods, leaves, flowers, branches, fruit, stalks, roots, root tips, anthers, cotyledons, hypocotyls, radicles, single cells, gametes, cell cultures, tissue cultures, and the like. A cotyledon is a type of seed leaf; a small leaf contained on a plant embryo. A cotyledon contains the food storage tissues of the seed. The embryo is a small plant contained within a mature seed. "Plant cells" also encompasses non-regenerable plant cells. Progeny, derivatives, variants, and mutants of regenerated plants are also included within the scope of the present embodiments, provided that these parts comprise at least some event NS-B50027-4 nucleic acid molecules, typically one or two of two loci of the elite event of NS-B50027-4. The present embodiments are also directed to the use of elite event NS-B50027-4 transgenes in plant cell culture and tissue culture. The embodiments include plants and plant parts from the elite event NS-B50027-4 line, as well as other plants produced by the described methods that add to the genetic make-up of NS-B50027-4 or progeny that comprise at least one of two transgenic loci of NS-B50027-4.

An "allele" is an alternative form of a gene that relates to one trait or characteristic. In a diploid cell or organism, the two alleles of a given gene occupy corresponding loci on a pair of homologous chromosomes.

A "locus" confers one or more traits such as, for example, modified fatty acid metabolism, modified phytic acid metabolism, modified carbohydrate metabolism, male sterility, herbicide tolerance, insect resistance, disease resistance, or modified protein metabolism. The trait may be, for example, conferred by a naturally occurring gene introduced into the genome of the line by backcrossing, a natural or induced mutation, or a transgene introduced through genetic transformation techniques. A locus may comprise one or more alleles integrated at a single chromosomal location. "Quantitative trait loci" (QTL) refers to a section of DNA (the locus) that correlates with variation in a phenotype (the quantitative trait). QTL are often linked to, or contain, the genes that control that phenotype. QTL are mapped by identifying which molecular markers (such as SNP or AFLP) correlate with an observed trait.

"Percent identity" refers to the comparison of the homozygous alleles of two canola or *Brassica* varieties. Percent identity is determined by comparing a statistically significant number of the homozygous alleles of two developed varieties. For example, a percent identity of 90% between NS-B50027-4 and a second *Brassica* means that the two *Brassica* have the same alleles at 90% of their loci. With regard to a defined DNA molecule or protein, the % identity the minimum % identity of an identified sequence (SEQ ID NO) comprises a nucleotide sequence that is at least 60%, at least 65%, at least 70%, at least 75%, at least 76%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical, inclusive, to the relevant nominated sequence designated by SEQ ID NO.

Degeneracy of the genetic code allows for a greater range of % identity for polynucleotide sequences than may be typically acceptable for proteins because of the myriad of nucleotide combinations that can encode a given protein. Moreover, amino acid substitution allows for many immaterial changes in protein's primary amino acid structure, e.g., amino acid substitutions that do not disrupt enzymatic function. Additionally, polynucleotides may possess, when compared to naturally occurring molecules, one or more mutations that are deletions, insertions, or substitutions of nucleotide residues. Polynucleotides that have mutations relative to a reference sequence can be either naturally occurring (that is to say, isolated from a natural source) or synthetic (e.g., by performing site-directed mutagenesis or DNA shuffling).

Generally, an "event" is an artificial genetic locus that, as a result of genetic manipulation, carries a foreign DNA comprising a gene or genes of interest (transgene(s)). The typical allelic states of an event are the presence or absence of the foreign DNA. An event may be characterized phenotypically by the expression of one or more transgenes. At the genetic level, an event is part of the genetic makeup of a plant. At the molecular level, an event may be characterized by restriction map, by the upstream or downstream flanking sequences of the transgene(s), or the molecular configuration of the transgene(s). Usually, transformation of plant cells or plant parts with a transforming DNA leads to a multitude of events, each of which is unique.

The term "gene" refers to a DNA molecule typically comprising several operably linked DNA regions, such as a promoter and a 5' untranslated region (5'UTR or 5' noncoding sequences) which together form the promoter region; a coding region (which may or may not encode a protein); and an untranslated 3' region (3'UTR or 3' noncoding sequences) comprising a polyadenylation site. Typically, in plant cells the 5'UTR, coding, and 3'UTR regions are transcribed into an RNA molecule which, in the case of a protein-encoding gene, is translated into protein. "Coding sequence" thus refers to the sequence of nucleotides in a DNA molecule providing codons that translate (via messenger RNA, ribosomal, and associated translation apparatus) a specific sequence of amino acids. A gene may include additional DNA regions such as, for example, introns. "Genotype" refers to the genetic constitution of a cell or organism. A "genetic locus" is generally the position of a given gene or set of genes in the genome of a plant.

The term "transgene" refers to a gene of interest as incorporated in the genome of a plant. Accordingly, a "transgenic plant" comprises at least one transgene in the genome of all of its cells. The transgenes of the present embodiments comprise at least one copy of the following enzymes expressed in the biosynthesis of LC-PUFA in line NS-B50027-4: Δ4-desaturase derived from the marine microalga *Pavlova salina,* Δ5-desaturase derived from *P. salina,* Δ5-elongase derived from the micro alga *Pyramimonas cordata,* Δ6-desaturase derived from the micro alga *Micromonas* pusilla, Δ6-elongase derived from *P. cordata,* Δ12-desaturase from the yeast *Lachancea kluyveri,* and Δ15/ω3-desaturase derived from the yeast *Pichia pastoris.* Alternatively or additionally, the transgenes of the present embodiments comprise Δ5-desaturase derived from *P. salina,* Δ5-elongase derived from *P. cordata,* Δ6-desaturase derived from M *pusilla,* and Δ15/ω3-desaturase derived from *P. pastoris.* The transgenes of NS-B50027-4 are arranged in a binary fashion in expression cassettes that include the appropriate regulatory regions. The transgenes of NS-B50027-4 described above are artificial in that they were designed using codon optimization strategy, and thus the transgenes do not otherwise exist in nature. The transgenic expression cassette included at least one matrix attachment region (MAR) from *Nicotiana tabacum.* The transgenic cassette also included a selectable marker gene. See, e.g., WO 2013185184; US 2015/0166928; PCT/US2017/38047, filed Jun. 16, 2017, which claims priority benefit of U.S. Provisional Application No. 62/351,246.

"Foreign" or "heterologous" when referring to a gene or a DNA molecule with respect to a plant species, indicates that the gene or DNA molecule, or a portion thereof (e.g., a particular region), is not naturally found in that plant species, or is not naturally found in that genetic locus in that plant species. The term "foreign DNA" also refers to a DNA molecule that will or has been incorporated into the genome of a plant as a result of transformation. In the context of this disclosure, a transgene, transgenic cassette, or transgenic expression cassette comprises at least one foreign or heterologous DNA.

The term "chimeric" when referring to a gene or DNA molecule is used to indicate that the gene or DNA molecule comprises at least two functionally relevant DNA regions (such as promoter, 5'UTR, coding region, 3'UTR, intron) that are not naturally associated with each other, and originate from different sources such that at least one DNA region is foreign to another DNA region in the chimeric DNA molecule.

The terms "plasmid" or "vector" refer to an extra chromosomal element often carrying genes that are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotides have been joined or recombined into a unique construct that is capable of introducing, for example, an expression cassette into a cell. In relation to transgenic plants, such plasmids or vectors may contain regions of T-DNA that facilitate insertion of transgene(s) into the plant genome.

"Expression cassette" refers to a genetic construct containing a transgene and having elements in addition to the foreign gene that allow for expression of that gene in a foreign host (e.g., a 5' promoter (optionally with an enhancer) untranslated ("UTR") DNA, DNA encoding a selected gene product, and appropriate 3' UTR DNA); and may refer to the cassette before and after insertion into the genome of the plant. In other words, a transgenic insert comprises an expression cassette. Accordingly, "insert DNA" refers to a heterologous DNA introduced to plant material via the transformation process, and includes DNA (that differs from the original/wild-type/native) DNA used for such transformation as explained herein. Insert DNA is typically a transgenic expression cassette.

The "transforming DNA" refers to a recombinant DNA molecule used for transformation, e.g., an expression vector. The transforming DNA usually comprises at least one "gene of interest" (e.g., a chimeric gene) that is capable of conferring one or more specific characteristics to the transformed plant.

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" organisms.

The term "recombinant DNA molecule" is used to exemplify and thus can include an isolated nucleic acid molecule that can be DNA and that can be obtained through recombinant or other procedures such as synthetic DNA synthesis or PCR. PCR (polymerase chain reaction) is a reaction in which replicate copies of a target polynucleotide are made using primers consisting of "upstream" and a "downstream" primer, and a catalyst of polymerization, such as a DNA polymerase, and typically a thermally-stable polymerase enzyme. Methods for PCR are known in the art. See, e.g., PCR (McPherson & Moller, eds., BIOS Sci. Publ. Ltd., Oxford, 2000). PCR can be performed on genomic DNA or cDNA.

"Suitable regulatory elements" or "suitable regulatory sequences" refer to polynucleotides located upstream (e.g., 5'UTR), within, or downstream (3'UTR) of a coding region, that influence the transcription, RNA processing or stability, or translation of the associated coding region. Regulatory elements may include promoters, enhancer elements, translation leader sequences, introns, polyadenylation recognition sequences, RNA processing sites, effector binding sites, and stem-loop structures.

"Promoter" refers to a DNA element capable of controlling the expression of a coding region or functional RNA. In general, a coding region is located 3' to a promoter element. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." It is further recognized that because, in most cases, the exact boundaries of regulatory elements have not been completely defined, DNA fragments of different lengths may have identical promoter activity.

The terms "3' non-coding sequences" and "transcription terminator" or 3'UTR refer to DNA elements located downstream of the coding region of the DNA molecule. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding region.

"Operably linked" refers to the association of nucleic acid elements on a single nucleic acid molecule or portion thereof so that the function of one element is affected by the other. For example, a promoter is operably linked with a coding region when it is capable of affecting the expression of that coding region (i.e., the coding region is under the transcriptional control of the promoter). Coding regions can be operably linked to regulatory elements in sense or antisense orientation.

"Mutagenesis" is a process in which an agent, such as ethyl methylsulfonate, known to cause mutations in genetic material is applied to plant material for the purpose of causing new genetic variability in a species, and is usually done with a specific trait in mind. See Swanson et al., 7 Plant Cell Rep. 83 (1988). Other techniques include generation of mutants directed at specific nucleotide or amino acid changes (substitutions, deletions, or additions). Such methods of introducing nucleic acid sequence changes are included by the term "mutagenesis." Mutagenesis can be useful in "knockout" experiments to disrupt genetic expression.

"Primers" are relatively short polynucleotides or oligonucleotides that are complementary to a portion of a polynucleotide to be amplified, for example, by polymerase chain reaction. Typically, a primer is no more than 50 nucleotides long, such as less than about 30 nucleotides long, or less than about 24 nucleotides long.

"Expression," as used herein, refers to the transcription and stable accumulation of sense (mRNA) derived from the nucleic acids of the invention. Expression may also refer to translation of mRNA into a polypeptide.

Reference to a cell includes a plant cell, whether isolated, in tissue culture, or incorporated in a plant or plant part, unless otherwise stated or clear from context.

"Regeneration" involves the selection of cells capable of regeneration (e.g., seeds, microspores, ovules, pollen, vegetative parts) from a selected plant or variety. These cells may optionally be subjected to genetic transformation or mutagenesis, following which a plant is developed from the cells using regeneration, fertilization, or growing techniques based on the type of genetically modified cells. Applicable regeneration techniques are known to those skilled in the art; see, e.g., Armstrong & Green, 165 Planta 322 (1985); Close & Ludeman, 52 Planta Sci. 81 (1987).

"Progeny" means all descendants including offspring and derivatives of a plant or plants and includes the first, second, third, and subsequent generations; and may be produced by self-pollination or crossing with plants with the same or different genotypes, and may be modified by a range of suitable genetic engineering techniques. Cultigen generally relates to plants that have been deliberately altered and selected by human. "T0" refers to the first generation of transformed plant material, "T1" refers to the seed produced on T0 plants, T1 seed gives rise to plants that produce T2 seed, etc., to subsequent Tx progeny.

"Breeding" includes all methods of developing or propagating plants and includes both intra- and inter-species and intra- and inter-line crosses as well as all suitable conventional breeding and artificial breeding techniques. Desired traits (e.g., NS-B50027-4 DHA trait) may be transferred to other canola or *B. napus* lines, cultivars, or cultigens; or through conventional breeding methods and can also be transferred to other *Brassica* species, such as *B. juncea* and *B. rapa* through inter-specific crossing. Both conventional breeding methods and inter-specific crossing methods, as well as other methods of transferring genetic material between plants, are well-known in the art.

"Backcrossing" is a process in which a breeder repeatedly crosses hybrid progeny back to a parental line. For example, crossing a first generation hybrid F1 with one of the parental genotypes of the F1 hybrid is backcrossing. Backcrossing can be used to introduce a trait of interest from a donor parent (a transgenic parent) into a recurrent parent (an elite line to be modified): the donor parent is crossed to the recurrent parent; the progeny of this cross is then backcrossed to the recurrent parent; the progeny of these crosses are selected for the trait of interest and then crossed back to the recurrent parent; this process is repeated for as many backcrosses as are needed to create a line in which the recurrent parent is homozygous for the trait from the donor parent. Backcrossing can also be combined with selfing, which can be advantageous when introducing recessive genes.

"Introgression" is the stable incorporation of genes from one gene pool into another. "Introgressive hybridization" refers to the incorporation (usually via hybridization and backcrossing) of alleles from one entity into the gene pool of a second, different entity. Introgression lines allow the study of quantitative trait loci, and also provide a means of introducing new traits, i.e., NS-B50027-4 traits, into other canola or *Brassica*, such as *B. napus* or *B. juncea*. Recipient lines of interest include open-pollinated (OP) herbicide tolerant lines, such as triazine tolerant (TT); Roundup Ready® (RR); stacked TT and RR; imidazolinone (IMI) tolerant OP lines; or IMI restorer (Rf) lines; high percent seed oil lines; optimal background for DHA lines; or lines selected for regional adaptation. Such lines can be developed as hybrids or elite events. Because existing isogenic canola lines exhibit seed oil potential of 45%, introgression of NS-B50027-4 loci may generate seed oil containing 20% DHA in bulk yield in such stacked events. Further breeding event stacks may be selected for production of EPA or DPA. Indeed, NS-B50027-4 genes (either one or both loci) can be stacked with other transgenic *Brassica* that contain at least one seven- or eight-gene insert (i.e., seven enzymes and, optionally, a marker), via transformation with the same vector or a similar vector used to generate NS-B50027-4, resulting in, for example, a plant with three loci that provides for production of LC-PUFA. Alternatively, as described further herein, the A02 and A05 loci can be segregated from NS-B50027-4, and the A02 locus stacked in other LC-PUFA producing lines (e.g., a line with a single insert for production of EPA, DPA, or DHA) to increase LC-PUFA production.

"Disease resistance" is generally the ability of a plant to restrict the activities of a specified pest, such as an insect, fungus, virus, or bacterium. "Disease tolerance" is the ability of plants to endure a disorder caused by a specified pest (such as an insect, fungus, virus, or bacterium), or an adverse environmental condition, yet still perform and produce in spite of this disorder.

"Fatty acid composition" or "fatty acid content" generally refer to percentages by weight of various fatty acids present in the endogenously formed oil of the mature, whole, partially dried seeds. The common industry practice is to report fatty acid composition as area percentage (area normalized), rather than absolute weight percentage, but the former approximates the latter. Absolute results can be calculated using individual reference standards of known concentration and an internal standard to calculate results on a mg/kg basis. It is also possible to use correction factors to calculate masses of fatty acids without the use of individual fatty acid standards, although an internal standard may still be needed. Commonly, fatty acid content is determined by crushing seed and extracting fatty acids as fatty acid methyl esters (FAME), which can be analyzed for fatty acid content by a variety of techniques that generate data as area percent or from which area percent can be derived. Example analytical approaches include gas chromatography (GC), GC-mass spectrometry (GC-MS), liquid chromatography-mass spectrometry (LC-MS), nuclear magnetic resonance (NMR), or near infrared reflectance spectroscopy. Total lipid may be separated by techniques known in the art to purify fractions, for example, such as the TAG fraction. Other methods of characterizing fatty acid compositions are known to those skilled in the art. See, e.g., CANOLA: CHEM., PRODUCTION, PROCESSING & UTILIZATION (Daun et al., eds., AOCS Press, Urbana, IL, 2011) (Daun et al., 2011); US 2015/0166928; US 20160002566.

Similarly, "oil content" is the typical percentage by weight oil present in the mature, whole, partially dried seeds (typically containing about 6% or 7% moisture). Percent oil, also be referred to as oil content, is calculated as the weight of the oil divided by the weight of the seed at a standardized moisture content. Oil content can be characteristic of different plant varieties. It can be determined using various analytical techniques such as nuclear magnetic resonance (NMR), near infrared reflectance (NIR), and Soxhlet extraction. For example, canola oil content can be measured by NMR techniques (Rossell & Pritchar, ANALYSIS OF OILSEEDS, FATS & FATTY FOODS 48-53 (Elsevier Sci. Pub. Ltd, London, 1991), by a pulsed wave NMS 100 Minispec, which simultaneously measures moisture content. Seed oil content can also be measured by NIR spectroscopy. Li et al. 67 Phytochem. 904 (2006).

The phrases "extracted plant lipid," "isolated plant lipid," "extracted lipid," and the like, refer to compositions comprising lipids that have been extracted from, for example, crushed plant or plant parts, such as seed. The extracted lipid can be a relatively crude composition obtained by, for example, crushing a plant material, such as seed; or a more purified composition in which most, if not all, of the water, nucleic acids, proteins, or carbohydrates derived from the plant material have been removed from the oil. Examples of purification methods are known in the art. In some embodiments, the extracted or isolated plant lipid comprises at least about 60%, at least about 70%, at least about 80%, at least about 90%, or at least about 95% (wt./wt.) lipid by weight of the composition. The extracted lipid may be solid or liquid at room temperature, the latter being considered herein "oil." In some embodiments, extracted lipid has not been blended with another lipid, such as DHA, produced by another source (e.g., DHA from fish oil). In some embodiments, following extraction the ratio of oleic acid to DHA, palmitic acid to DHA, linoleic acid to DHA, or total ω6 fatty acids to total ω3 fatty acids has not been altered significantly (for example, no greater than a 10% or 5% alteration) compared with the ratio in the intact seed or cell. In other words, the extracted oil has not been enriched for a particular fatty acid, e.g., DHA. In other embodiments, the extracted plant lipid has not been exposed to a procedure, such as hydrogenation or fractionation, that alters the ratio of oleic acid to DHA, palmitic acid to DHA, linoleic acid to DHA, or total ω6 fatty acids to total ω3 fatty acids, when compared with the ratio in the intact seed or cell. In other words, the extracted oil has not been enriched for a particular fatty acid, e.g., DHA. When the extracted plant lipid of the present embodiments is oil, the oil may further comprise non-fatty acid molecules such as sterols.

As noted above, the phrases "extracted plant oil" and "isolated plant oil" refer to compositions comprising extracted plant lipid or isolated plant lipid that is a liquid at room temperature. The oil is obtained from a plant or part thereof, such as seed. The extracted or isolated oil can be a relatively crude composition obtained by, for example, crushing a plant seed; or a more purified composition where most, if not all, of the water, nucleic acids, proteins, or carbohydrates derived from the plant material has been removed from the oil. The composition may comprise other components which may be lipid or non-lipid. In an embodiment, the oil composition comprises at least about 60%, at least about 70%, at least about 80%, at least about 90%, or at least about 95% (w/w) extracted plant lipid. In an embodiment, extracted oil of the invention has not been blended with another oil such as DHA not produced by another source (for example, DHA from fish oil). In one embodiment, following extraction, the ratio of oleic acid to DHA, palmitic acid to DHA, linoleic acid to DHA, or total ω6 fatty acids to total ω3 fatty acids, has not been altered significantly (for example, no greater than a 10% or 5% alteration) when compared with the ratio in the intact seed or cell. In an another embodiment, the extracted plant oil has not been exposed to a procedure, such as hydrogenation or fractionation, that alters the ratio of oleic acid to DHA, palmitic acid to DHA, linoleic acid to DHA, or total ω6 fatty acids to total ω3 fatty acids, when compared with the ratio in the intact seed or cell. Extracted plant oil of these embodiments may comprise non-fatty acid molecules such as sterols.

As used herein, "oil" is a composition comprising predominantly lipid and which is a liquid at room temperature. For instance, oil of the invention preferably comprises at least 75%, at least 80%, at least 85% or at least 90% lipid by weight. Typically, purified plant oil comprises at least 90% triacylglycerols (TAG) by weight of the lipid in the oil. Minor components of oil, such as diacylglycerols (DAG), free fatty acids (FFA), phospholipid, or sterols, may be present in oil. Edible oil derived from NS-B50027-4 may be characterized by one or more of the following characteristics: a DHA content of at least about 7% by weight, a DPA content of at least about 1% by weight, an EPA content of at least about 0.4% by weight, an oleic/cis-vaccenic acids content of about 46% by weight, a linoleic acid content of about 8.2% by weight, an ALA content of at least about 19%, a combined ALA/Arachidic/SDA content of about 21% by weight, a combined EPA/DPA/DHA content of at least about 9% (% wt. total fatty acids). In some embodiments, the combined EPA/DPA/DHA content is about 16%.

As used herein, the term "fatty acid" refers to a carboxylic acid often with a long aliphatic tail, either saturated or unsaturated. Typically, fatty acids have a carbon-carbon bonded chain of at least eight carbon atoms in length, for example at least 12 carbons, 16 carbons, 18 carbons, 20 carbons, 22 carbons, or 24 carbons in length. Most naturally occurring fatty acids have an even number of carbon atoms because their biosynthesis involves acetate which has two carbon atoms. The fatty acids may be in a free state (non-esterified); in an esterified form such as part of a triglyceride (TAG), diacylglyceride (DAG), monoacylglyceride; be acyl-CoA (thioester)-bound or in another bound form. The fatty acid may be esterified as a phospholipid, such as a phosphatidylcholine, phosphatidylethanolamine, phosphatidylserine, phosphatidylglycerol, phosphatidylinositol, or diphosphatidylglycerol.

"Saturated fatty acids" contain no carbon-carbon double bonds (alkenes) or other functional groups along the chain. "Saturated" thus refers to the presence of hydrogen at all possible carbons (apart from the carboxylic acid [—COOH] group). In other words, in a saturated fatty acid the omega (w) end (also called the n-end) of the fatty acid contains three hydrogens (—CH$_3$), and each carbon within the chain contains two hydrogens (—CH$_2$—). "Total saturates" typically refers to the combined percentages of palmitic (C16:0), stearic (C18:0), arachidic (C20:0), behenic (C22:0), and tetracosanoic (C24:0) fatty acids.

"Unsaturated fatty acids" share a similar backbone with saturated fatty acids, except they include at least one alkene group (—CH═CH—) in the carbon chain. The two flanking carbon atoms (bound to either side of the alkene group) can occur in a cis or trans configuration. "Monounsaturated fatty acids" refers to fatty acids that have at least twelve carbon atoms but only one alkene group in the carbon chain. "Polyunsaturated fatty acids" or "PUFAs" refer to fatty acids that have at least twelve carbon atoms and at least two alkene groups in the carbon chain. "Long-chain polyunsaturated fatty acids" and "LC-PUFAs" refer to fatty acids that have at least twenty carbon atoms in the carbon chain and have at least two alkene groups. "Very long-chain polyunsaturated fatty acids" and "VLC-PUFAs" refer to fatty acids that have at least twenty-two carbon atoms and at least three alkene groups in the carbon chain. A reference to LC-PUFA includes VLC-PUFA. Ordinarily, the number of carbon atoms in the carbon chain of fatty acids refers to an unbranched carbon chain. If the carbon chain is branched, the number of carbon atoms excludes those in side-groups.

In one embodiment, the LC-PUFA is an "ω3 fatty acid" or "Omega-3 fatty acid": it has a desaturation (alkene group, double bond, or C═C) at the third carbon-carbon bond from the methyl end of the fatty acid. In another embodiment, the LC-PUFA is an ω6 fatty acid: it has a desaturation (alkene group) in the sixth carbon-carbon bond from the methyl end of the fatty acid. The position of the alkene in the fatty acid chain is also annotated using Δ (or delta), in which the position of the alkene is numbered with reference to the carboxylic end of the fatty acid. For example, linoleic acid can also be designated "cis-49, cis-412 octadecadienoic acid" or $\Delta^{9,12}$ octadecadienoic acid." Fatty acids can also be identified with reference to a "C:D" lipid number, in which C is the number of carbons and D is the number of double bonds in the carbon backbone. For example, arachidonic acid can be annotated 20:4$\Delta^{5,8,11,14}$ meaning a twenty-carbon chain with four alkene groups, located at carbons 5, 8, 11 and 14 from the carboxylic end of the fatty acid. This name also indicates that arachidonic acid is an ω6 fatty acid because if there are twenty carbons and an alkene at C14 from the carboxylic end, the first alkene from the methyl end must be at C6.

In a further embodiment, the LC-PUFA is selected from the group consisting of: arachidonic acid (ARA, 20:4$\Delta^{5,8,11,14}$; ω6), eicosatetraenoic acid (ETA, 20:4$\Delta^{8,11,14,17}$; ω3); eicosapentaenoic acid (EPA, 20:5$\Delta^{5,8,11,14,17}$; ω3), docosapentaenoic acid (DPA, 22:5$\Delta^{7,10,13,16,19}$; ω3), or docosahexaenoic acid (DHA, 22:6$\Delta^{4,7,10,13,16,19}$; ω3). The LC-PUFA may also be dihomo-γ-linoleic acid (DGLA) or eicosatrienoic acid (ETrA, 20:3$\Delta^{11,14,17}$; ω3). The LC-PUFA produced according to the present embodiments may be a mixture of any or all of the above, and may include other LC-PUFAs or derivatives of any of these LC-PUFAs. In at least one embodiment, the ω3 fatty acids are at least one of DHA; DPA and DHA; or EPA, DPA, and DHA.

Furthermore, as noted above a LC-PUFA and VLC-PUFA can be a free fatty acid (non-esterified), esterified, or in another bound form. Thus, the LC-PUFA of the present embodiments may be present as a mixture of forms in the lipid of a cell, extracted lipid, or purified oil. In at least one embodiment, the oil comprising at least 75% or at least 85% triacylglycerols ("TAG"), with the remainder present as other forms of lipid such as those mentioned, with the TAG comprising at least one LC-PUFA. The oil may subsequently be further purified or treated, for example by hydrolysis with a strong base to release the free fatty acids, or by distillation or the like.

Accordingly, "total ω3 fatty acids," "total ω3 fatty acid content," and the like, refers to the sum of all ω3 fatty acids, esterified and non-esterified, in extracted lipid, oil, recombinant cell, plant part or seed, as the context determines, typically expressed as a percentage of the total fatty acid content. These ω3 fatty acids include ALA, SDA, ETrA, ETA, EPA, DPA, or DHA, and exclude any ω6 fatty acids or monounsaturated fatty acids. "New ω3 fatty acids," "new ω3 fatty acid content," and the like, refers to the sum of all ω3 fatty acids excluding ALA, esterified and non-esterified, in the extracted lipid, oil, recombinant cell, plant part or seed, as the context determines, expressed as a percentage of the total fatty acid content. These new ω3 fatty acids are the fatty acids that are produced in the cells, plants, plant parts and seeds of the present embodiments by the expression of elite event transgenic constructs, and if present include SDA, ETrA, ETA, EPA, DPA, or DHA, but exclude ALA, any ω6 fatty acids, or monounsaturated fatty acids. Exemplary total ω3 fatty acid contents and new ω3 fatty acid contents can be determined by conversion of fatty acids in a sample to FAME and analysis by GC using methods known in the art. See, e.g., American Oilseed Chemists' Society (AOCS) method Celd-91.

Similarly, "total ω6 fatty acids," "total ω6 fatty acid content," and the like, refer to the sum of all the ω6 fatty acids, esterified and non-esterified, in the extracted lipid, oil, recombinant cell, plant part or seed, as the context determines, expressed as a percentage of the total fatty acid content. "Total ω6 fatty acids," if present, may include LA, GLA, DGLA, ARA, EDA, or ω6-DPA, and excludes any ω3 fatty acids or monounsaturated fatty acids. "New ω6 fatty acids," "new ω6 fatty acid content," and the like, refers to the sum of all ω6 fatty acids excluding LA, esterified and non-esterified, in the extracted lipid, oil, recombinant cell, plant part or seed, as the context determines, expressed as a percentage of the total fatty acid content. These new ω6 fatty acids are the fatty acids that are produced in the cells, plants, plant parts, or seeds as described herein, through expression of the elite event transgenes, and may include GLA, DGLA, ARA, EDA, or ω6-DPA, but exclude LA, any ω3 fatty acids, or monounsaturated fatty acids.

"Half-seed analysis" is a procedure whereby fatty acid analysis is carried out on one of the two cotyledons (half-seed) and the remaining seedling carrying the second cotyledon is used to form a plant if the results of the analysis are positive.

"Protein content" is the typical percentage by weight of protein in the oil-free meal, or substantially oil-free meal, e.g., with 95% or 99% of the oil removed, from the mature whole dried seeds, as determined by methods known in the art. See, e.g., Daun et al., 2011; AOCS Official Meth. Ba 4e-93 Combustion Meth. Determination Crude Protein.

Mature seed produced by commercial growers for purposes other than growing or reproducing the species is sometimes referred to as "grain."

As the skilled person would appreciate, for example, the term "obtaining a plant part" as a step in the process of the present embodiments can include obtaining one or more plant parts, such as seed, for use in the process. Obtaining the plant part includes harvesting the plant part from a plant such as with a mechanical harvester, or purchasing the plant part, or receiving the plant part from a supplier, or otherwise obtaining a plant part by acquiring the plant part from someone else who has harvested the plant part. Accordingly, for example, obtaining seed from NS-B50027-4 or progeny of NS-B50027-4 may include cultivating plants, harvesting seed from plants, purchasing seed, receiving seed, acquiring seed, placing seed in a container or storing seed, or transporting seed to a different location.

"Essentially all of the physiological and morphological characteristics of a parent" refers to a plant that has essentially all of the physiological and morphological characteristics of the recurrent parent, except for the characteristics derived from the converted trait.

Inbred Canola Line NS-B50027-4

Canola line NS-B50027-4 is a stable and uniform breeding line, as described herein. NS-B50027-4 has been bred with careful attention to uniformity of plant type, and the line has been increased with continued observation for uniformity. NS-B50027-4 has been field tested, under regulatory authorization, at ten sites in major canola growing regions of Australia and Canada. Agronomic performance assessments were conducted in multi-site field studies to measure characteristics such as emergence, seedling vigor, plant height, lodging, and yield. All field trials were also observed for opportunistic disease or insect stressors as well as normal phenotypic characteristics.

The line NS-B50027-4 is similar to the Australian cultivar AV Jade (the parent isogenic line) in terms of leaf, flower and silique, and produces plants of a similar plant height and habit at maturity. The line NS-B50027-4 has acceptable resistance to blackleg disease (*Leptosphaeria*), and has similar seed yield potential in typical Australian canola cropping environments and shows no increased propensity for seed shattering or plant lodging at maturity compared with AV Jade. There were no meaningful differences observed between DHA canola and AV Jade for plant pest characteristics, and no indication of a selective advantage that could result in increased weediness potential of NS-B50027-4 canola.

In addition to the LC-PUFA trait, the line NS-B50027-4 is distinguishable from AV Jade by a slightly longer time to reach flowering stage and is similar to the Australian cultivar ATR Wahoo in this respect. NS-B50027-4 is distinguished particularly for the production in its seeds of LC-PUFA, particularly LC-ω3 fatty acids, and more particularly DHA. Canola line NS-B50027-4 is not a parent of any other canola cultivar commercialized at the time of the patent filing for this line NS-B50027-4.

Inbred transgenic canola line NS-B50027-4 has the following morphology and physiological characteristics (based primarily on data collected and averaged from eight different locations in Australia during 2015):

TABLE 1

Description Information: NS-B50027-4 and AV Jade

| | NS-B50027-4 | Comparator: AV Jade |
|---|---|---|
| Species | *Brassica napus* | *Brassica napus* |
| Leaf: Green color | medium | medium |
| Leaf: Lobes | present | present |
| Leaf: Number of lobes | medium | medium |
| Leaf: Dentation of margin | medium | medium |
| Leaf: Length | medium | medium |
| Time of Flowering | medium to late | medium |
| Flower: Color of petals | yellow | yellow |
| Flower: Width of petals | medium | medium |
| Flower: Production of pollen | present | present |

TABLE 1-continued

Description Information: NS-B50027-4 and AV Jade

| | NS-B50027-4 | Comparator: AV Jade |
|---|---|---|
| Plant: Seedling vigor | medium to high | medium |
| Plant: Height at full flowering | medium | medium |
| Plant: Lodging at maturity | low | low |
| Blackleg Disease Resistance | present | present |
| Silique: Length | medium to long | medium to long |
| Silique: Length of beak | medium | medium |
| Silique: Length of peduncle | medium to long | medium to long |
| Seed Shattering | low | low |
| Seed: Yield | high | high |
| Seed % Oil | moderate | moderate |
| Seed: % Erucic Acid | nil | nil |
| Seed: % EPA C20:5n3 | present | absent |
| Seed: % DPA C22:5n3 | present | absent |
| Seed: % DHA C22:6n3 | present | absent |

Another aspect of the present embodiments provides a method for producing a NS-B50027-4-derived *Brassica* or canola plant, or parts thereof such as seed, comprising obtaining the seed of NS-B50027-4 or the seed of the novel *Brassica napus* line described above, and growing the seed to a plant under *Brassica* or canola growing conditions. Another embodiment provides for obtaining a hybrid seed by obtaining seed of NS-B50027-4 or the seed of the *Brassica napus* line as described above, growing the plant, cross-pollinating the plant, and obtaining seed that matures from the cross-pollination. The seed can then be cultivated under *Brassica* plant or canola growing conditions to obtain a hybrid *Brassica* or canola plant, or parts thereof, including seed. Accordingly, another aspect provides a method of growing *Brassica napus* line NS-B50027-4 (representative seed of said line having been deposited under ATCC® Accession No. PTA-123186), a sub-line of NS-B50027-4, progeny of NS-B50027-4 or the sub-line, or a plant produced by crossing NS-B50027-4 with a second *Brassica* plant comprising: obtaining *Brassica* NS-B50027-4 seed or the seed of a *Brassica napus* line as described above, and growing the seed under *Brassica* plant growing conditions. Further aspects regarding progeny, hybrids, and introgression hybridization to yield NS-N50027-4 are described herein.

Elite Event

The phenotypic expression of transgenes in canola is determined both by the structure of the transgene cassette itself and by its insert location in the plant genome: the presence of transgenes at particular locations in the plant genome may influence the expression of the transgene and the overall phenotype of the plant. The incorporation of a recombinant DNA molecule in the plant genome typically results from transformation of a cell or tissue (or from another genetic manipulation). The particular site(s) of incorporation may be a matter of chance or predetermined (if a process of targeted integration is used). The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, breeding, and evaluation in a glasshouse or field trials, eventually leading to the selection of an elite event.

NS-B50027-4 was selected as an elite event in the development of canola that produces LC-PUFA, particularly LC-ω3 fatty acids, and more particularly DHA. An "elite event" is an event selected from a group of events, obtained by transformation with the same transforming DNA or by backcrossing with plants obtained by such transformation, based on the expression and stability of the transgene constructs, compatibility with optimal agronomic characteristics of the plant comprising such constructs, and realization of the desired phenotypic trait. Thus, the criteria for elite event selection are at least one, and advantageously all, of the following:

(a) the presence of the transgenes does not unduly compromise other desired characteristics of the plant, such as those relating to agronomic performance or commercial value;
  (b) the event is characterized by defined molecular configuration that is stably inherited and for which appropriate diagnostic tools for identity control can be developed;
  (c) the genes of interest in the transgene cassette show a correct, appropriate, and stable spatial and temporal phenotypic expression, at a commercially acceptable level in a range of environmental conditions in which the plants carrying the event are likely to be exposed in normal agronomic use. The transgenes may also be associated with positions in the plant genome that allow introgression into further desired commercial genetic backgrounds.

The status of an event as an elite event may be confirmed by introgression of the elite event in different relevant genetic backgrounds and observing compliance with at least one of the criteria, e.g., (a), (b) and (c) above. Additionally, selection of the elite events may also be determined on the compatibility, more specifically that the progeny resulting from a cross between NS-B50027-4 and a plant carrying at least one other event, such that progeny carry both events. Accordingly, an "elite event" refers to a genetic locus comprising a transgenic cassette(s) that answers to the above-described criteria. A plant, seeds, plant material or progeny can comprise one or more elite events in its genome.

Expression of the transgenes confers on the plant one or more phenotypic traits (e.g., production of LC-ω3 fatty acids) that were intended to be conferred by the introduction of the transforming DNA (on the basis of the structure and function of some or all of the genes of interest). In the present embodiments, several transgenes provide the biosynthetic pathway for the production of LC-ω3 fatty acids in the transformed plant.

An aspect of the present embodiments relates to the surprising number of copies of expressible transgenes in the NS-B50027-4 genome. "Expressible" means that the primary structure of the DNA molecule, i.e., the coding sequence of the transgene, indicates that the gene encodes an active protein. Expressible coding sequences may not be expressed, however, because "gene silencing" occurs via various mechanisms of homologous transgene inactivation in vivo. Homologous transgene inactivation has been described in plants in which a transgene has been inserted in the sense orientation, with the unexpected result that both the gene and the transgene were down-regulated. Napoli et al., 2 Plant Cell 279 (1990). Possible mechanisms for inactivation of homologous genetic sequences include transcriptional inactivation via methylation, in which duplicated DNA regions signal endogenous mechanisms for gene silencing, and post-transcriptional silencing, in which the combined levels of mRNA from both the endogenous gene and transgene trigger threshold-induced degradation of both messages. See van Bokland et al., 6 Plant J. 861 (1994). Surprisingly, however, although there are at least three copies of several transgenes in NS-B50027-4, some of which are disposed in the same orientation, NS-B50027-4 exhibits synergistic DHA expression.

Initial transformants cultivated from Brassica napus L. (var. AV Jade) exhibited a wide variation in levels of fatty acid production, particularly in EPA and DHA levels. For the second and third generations, selection was based primarily on DHA and EPA content of transgenic seeds. In some cases, particularly T2 or T3 generations, segregation patterns (determined by growing twenty to forty individual seeds from one plant to twenty to forty offspring, and then measuring the DHA and EPA content of the individual seeds of those offspring) also exhibited scattered results, indicating complex or multi-copy insertions had occurred. Many of the initial T2 or T3 generations of plants were thus discarded. Initially, it was concluded that multiple copies of the transgenic insert would yield unstable transformants, and also exhibit classic gene silencing seen in homozygous genotypes as discussed above. Therefore, if PCR analysis of transformed plants indicated copy number >1, those transformants were often discarded.

Surprisingly, elite event NS-B50027-4 was found to contain a stable (and functional) multi-copy event: a sixteen-gene insertion including two eight-gene-T-DNA-bordered cassettes (each eight-gene insert encoding seven enzymes and a marker) arranged in binary (inverted) left-border-to-left-border fashion (analogous to a massive palindrome); and a separate, smaller four-gene cassette; and this combination of transgene inserts act synergistically in the production of DHA in inbred line NS-B50027-4. More specifically, a combination of crossing, backcrossing, and self-crossing segregated the sixteen-gene insert to chromosome A05 (also called N05), and the four-gene insert to chromosome A02 (also called N02). The contribution of each transgenic chromosome was determined by breeding each segregant to obtain pure homozygous lines of each event. For example, in one experiment the segregant comprising the sixteen-gene insert produced about 4% DHA; and segregant comprising the four-gene insert produced no DHA; but when the segregants were bred to combine the transgenic chromosome A02 locus and transgenic chromosome A05 locus, the combination of the two transgenic inserts provided a plant that produced at least about 7% DHA to at least about 14% DHA, inclusive, in its seed. This result was unexpected. As noted, despite the unusual genetic makeup of elite event NS-B50027-4, the line has proved stable and consistent in fatty acid production.

As noted herein, the biosynthetic pathway for LC-PUFA included seed-specific promoters to limit expression and production of LC-PUFA to developing seed. No expression of any of the seven transgenes was detected in NS-B50027-4 whole plants, roots, flowers, or other plant tissues (e.g., flower bud, young silique) aside from seed. In developing seed, the transgenic proteins were present from highest to lowest content (ng/mg total protein): Paysa-Δ4D>Lackl-Δ12D>Picpa-ω3D>Micpu-Δ6D>Paysa-Δ5D>Pyrco-Δ6E, and Pyrco-Δ5E was undetectable. In mature seed, the transgenic protein was present from highest to lowest content (ng/mg total protein): Paysa-Δ4D>Lackl-Δ12D=Picpa-ω3D>Paysa-Δ5D>Micpu-Δ6D>Pyrco-Δ5E, while Pyrco-Δ6E was undetectable.

An aspect of the present embodiments provides a method of increasing the LC-PUFA in a plant by providing (e.g., by genetic transformation or breeding) the plant with multiple copies of genetic constructs expressing some enzymes of the "front end" of the LC-PUFA biosynthetic pathway. See Napier et al., 330 Biochem. J. 611 (1998) (characterizing structure as N-terminal cytochrome b5 domain and typical fatty acid-desaturase domain having three highly conserved histidine boxes). For example, although not all of the enzymes Δ6-desaturases, Δ5-desaturases, Δ5-elongases, and ω3/Δ15-desaturases (considered no. 2, no. 3, no. 5, and no. 6 in the biosynthetic pathway) may be considered exclusively as the front end desaturases, in particular embodiments these genes are assembled into an artificial locus that enhances the production of LC-PUFA such as DHA. In particular embodiments, the artificial locus comprising some front end genes includes *Micromonas pusilla*-derived Δ6-desaturase, *Pyramimonas cordata*-derived Δ5-elongase, *Pavlova salina*-derived Δ5-desaturase, and *Pichia pastoris*-derived Δ15/ω3-desaturase. The location of this artificial locus on chromosome A02 of NS-B50027-4 provides a means of segregating this locus into a plant line (segregant), and enables its introgression into another plant by conventional plant breeding techniques.

Oil and ω3 Fatty Acid

With canola line NS-B50027-4 plants, according to the present embodiments, ω3 and LC-ω3 fatty acid can be produced in commercial quantities from NS-B50027-4 canola seed. Thus, techniques for the selection and propagation of transformed plants yield a plurality of plants with advantageous traits of NS-B50027-4, that are harvested in a conventional manner and the fatty acid extracted from a tissue of interest, e.g., seeds.

In a further embodiment, extracted plant lipid can be treated to increase the level of DHA as a percentage of the total fatty acid content. For example, the treatment comprises hydrolysis of the esterified fatty acids to produce free fatty acids, or transesterification to modify TAG components. For example, oil from seed of NS-B50027-4 or its progeny may be enriched for DHA content, or treated to convert the fatty acids in the oil to alkyl esters such as methyl or ethyl esters, which may then be purified or fractionated to enrich the lipid or oil for DHA. In some embodiments, the fatty acid composition of the lipid after such treatment comprises at least 40%, at least 50%, at least 60%, at least 70%, at least 80%, at least 90%, or at least 95% DHA, inclusive.

The present embodiments also include progeny and descendants of these new *B. napus* lines from line NS-B50027-4. The progeny or descendants can be developed by methods of breeding or tissue culture as are known to those skilled in the art. For example, the progeny or descendants can contain the canola fatty acid profile developed in these lines. Accordingly, the descendants or progeny can have any number of genes from the developed lines. The descendants or progeny can include only those genes that provide the canola fatty acid phenotype provided herein, or additional genes. This can be determined by molecular analysis as is known to those skilled in the art.

An aspect provides a method for developing a *Brassica* seed, such as *B. napus* or *B. juncea*, having a phenotype of NS-B50027-4, for example, a DHA seed content of comprising at least 5%, about 6%, about 7%, about 8%, about 9%, about 10%, about 11%, about 12% DHA, about 13% DHA, about 14% DHA, about 15%, about 16% DHA, about 17% DHA, about 18% DHA, about 19% DHA, about 20% DHA, about 21% DHA, about 22% DHA, about 23% DHA, about 24% DHA, about 25% DHA, inclusive, or more DHA (as wt. % of total fatty acids); or for example, the LC-PUFA fatty acid content is at least 5% LC-PUFA, about 6% LC-PUFA, about 7% LC-PUFA, about 8% LC-PUFA, about 9% LC-PUFA, about 10% LC-PUFA, about 11% LC-PUFA, about 12% LC-PUFA, about 13%, about 14% LC-PUFA, about 15% LC-PUFA, about 16% LC-PUFA, about 17% LC-PUFA, about 18% LC-PUFA, about 19% LC-PUFA, about 20% LC-PUFA, about 21% LC-PUFA, about 22% LC-PUFA, about 23% LC-PUFA, about 24% LC-PUFA, about 25% LC-PUFA, inclusive, or more LC-PUFA (sum of EPA, DPA, and DHA as wt. % of total fatty acids).

Another aspect provides a homogeneous assemblage of crushed *Brassica napus* seed produced from the plants described herein (i.e., seed from NS-B50027-4 or seed from progeny comprising at least one locus of NS-B50027-4), wherein the crushed *B. napus* seed have at least about 30%, about 35%, or from about 36% to about 40%, inclusive, by weight, of total fatty acids (% wt. seed). In particular embodiments, for example, the fatty acid content of NS-B50027-4 seed or seed obtained from progeny comprising at least one locus from NS-B50027-4 comprises at least 5% DHA, about 6% DHA, about 7% DHA, about 8% DHA, about 9% DHA, about 10% DHA, about 11% DHA, about 12% DHA, about 13% DHA, about 14% DHA, about 15%, about 16% DHA, about 17% DHA, about 18% DHA, about 19% DHA, about 20% DHA, about 21% DHA, about 22% DHA, about 23% DHA, about 24% DHA, about 25% DHA, inclusive (as wt. % of total fatty acids), or more DHA. In particular embodiments, for example, the fatty acid content of NS-B50027-4 seed or seed of progeny containing at least one locus from NS-B50027-4 comprises at least 5% LC-PUFA, about 6% LC-PUFA, about 7% LC-PUFA, about 8% LC-PUFA, about 9% LC-PUFA, about 10% LC-PUFA, about 11% LC-PUFA, about 12% LC-PUFA, about 13%, about 14% LC-PUFA, about 15% LC-PUFA, about 16% LC-PUFA, about 17% LC-PUFA, about 18% LC-PUFA, about 19% LC-PUFA, about 20% LC-PUFA, about 21% LC-PUFA, about 22% LC-PUFA, about 23% LC-PUFA, about 24% LC-PUFA, about 25% LC-PUFA, about 26% LC-PUFA, about 27% LC-PUFA, about 28% LC-PUFA, about 29% LC-PUFA, about 30% LC-PUFA, about 31% LC-PUFA, about 32% LC-PUFA, about 33% inclusive, or more LC-PUFA (LC-PUFA is sum of EPA, DPA, and DHA as wt. % of total fatty acids). In other embodiments, for example, the fatty acid content of NS-B50027-4 seed comprises at least about 18% ALA, about 19% ALA, about 20% ALA, about 21% ALA, about 22% ALA, about 23% ALA, about 24% ALA, about 25% ALA, about 26% ALA, inclusive, or more ALA as wt. % of the total fatty acids of the seed.

Also provided is a homogeneous assemblage of crushed *Brassica napus* NS-B50027-4 seed disclosed herein, or a homogeneous assemblage of crushed *B. napus* seed from a progeny or descendent of NS-B50027-4, wherein the crushed *B. napus* seeds have a DHA content of at least 5% DHA, about 6% DHA, about 7% DHA, about 8% DHA, about 9% DHA, about 10% DHA, about 11% DHA, about 12% DHA, about 13% DHA, about 14% DHA, about 15%, about 16% DHA, about 17% DHA, about 18% DHA, about 19% DHA, about 20% DHA, about 21% DHA, about 22% DHA, about 23% DHA, about 24% DHA, about 25% DHA, inclusive, or more DHA (as wt. % of total fatty acids). Also provided is the oil, meal, and protein from such crushed seed.

In a further embodiment, extracted plant lipid (e.g., oil) can be treated to increase the level of DHA as a percentage of the total fatty acid content. For example, the treatment comprises hydrolysis of the esterified fatty acids to produce free fatty acids, or transesterification. For example, canola oil may be treated to convert the fatty acids in the oil to alkyl esters such as methyl or ethyl esters, which may then be fractionated to enrich the lipid or oil for DHA. In embodiments, the fatty acid composition of the lipid after such enrichment comprises at least 40%, at least 50%, at least 60%, at least 70%, at least 80%, at least 90% DHA, or at least 95% DHA, inclusive.

Another embodiment provides a method of producing oil or meal from *Brassica napus* line NS-B50027-4, representative seed of said line having been deposited under ATCC® Accession No. PTA-123186, a sub-line of NS-B50027-4, progeny of NS-B50027-4 or the sub-line, or a plant produced by crossing NS-B50027-4 with a second *Brassica* plant comprising: growing the *Brassica napus* plant of described above under *Brassica* plant growing conditions; harvesting the seed; and extracting oil, meal, or protein from the seed.

Another embodiment described herein provides a method of producing oil from *Brassica napus* line NS-B50027-4, representative seed of said line having been deposited under ATCC® Accession No. PTA-123186, a sub-line of NS-B50027-4, progeny of NS-B50027-4 or the sub-line, or a plant produced by crossing NS-B50027-4 with a second *Brassica* plant, comprising: crushing seeds of *Brassica napus* line NS-B50027-4, representative seed of said line having been deposited under ATCC® Accession No. PTA-123186, a sub-line of NS-B50027-4, progeny of NS-B50027-4 or the sub-line, or a plant produced by crossing NS-B50027-4 with a second *Brassica* plant; and extracting oil from said seeds.

Another aspect provides seed meal and protein, as well as oil, from NS-B50027-4 seed or NS-B50027-4-derived progeny seed. Protein extraction from plant biomass can be accomplished by known methods. See, e.g., Heney & Orr, 114 Anal. Biochem. 92 (1981). Meal from NS-B50027-4 seed may prove particularly advantageous because it contains at least some DHA and other ω3 fatty acids. Similarly, the protein fraction obtained from NS-B50027-4 seed comprises at least some beneficial DHA and other ω3 fatty acids. Accordingly, another embodiment provides seed meal obtained from seed of NS-B50027-4 seed or NS-B50027-4-derived progeny seed. In an embodiment, the seed meal comprises the NS-B50027-4 elite event. Advantageously, the seed meal retains some of the lipid or oil produced in the seed from which the seed meal is obtained, albeit at a lower level, after extraction of most of the lipid or oil from the seed. The seed meal may be used as a foodstuff, e.g., a component of animal feed or an ingredient in food production. Given the higher ratio of ω3:ω6 fatty acid in this seed meal, the meal of NS-B50027-4 seed may provide superior nutrition compared with other commercially available seed meal.

As noted above, "fatty acid content" or "fatty acid composition" generally refers to percentages by weight of various fatty acids present in the endogenously formed oil of the mature, whole, partially dried seeds (typically containing about 6% or 7% moisture), calculated as percent particular fatty acid as area normalized; or against a known standard; or as a weight ratio of fatty acid per gram of seeds (e.g., mg DHA/g seeds).

A common industry practice reports fatty acid composition as area percentage (area normalized), rather than as absolute quantities. For example, chromatography often generates data as peaks, and the area under each peak is integrated and presented as a percentage of the total area under all the peaks for fatty acids in the chromatogram. Area percentage is easy to calculate and compare with results reported by others in the industry who also report area percentage. Area percentage is not absolute, but provides an acceptable approximation. Absolute yield as mg/kg results can be calculated, for example, by including reference standards of known concentration and an internal standard. Correction factors can also be used to calculate mass amounts of fatty acids.

For example, in determining the fatty acid content the seeds may be crushed, the oil triacylglycerides (TAG) extracted, followed by saponification and methylation with methanol and sodium methoxide, or by reaction with 1.25% 3-(trifluoromethyl)phenyl-trimethyl-ammonium hydroxide in methanol (Meth Prep II™, Fischer Scientific Cat #AT18007), to form fatty acid methyl esters. The resulting fatty acid methyl esters (FAME) can be analyzed by gas-liquid chromatography (GLC), using a capillary column that separates the FAME based on the degree of unsaturation and fatty acid chain length. FAME can also be analyzed by, for example, GC, LC-MS, GC-MS, NMR or near infrared reflectance spectroscopy. Fatty acid composition may also be determined from whole seeds, e.g., by breaking the seed coats and subjecting the broken seeds to direct methylation. Total lipid may be separated by techniques known in the art to purify fractions such as the TAG fraction. For example, thin-layer chromatography (TLC) may be performed at an analytical scale to separate TAG from other lipid fractions such as DAG, acyl-CoAs or phospholipid in order to determine the fatty acid composition specifically of TAG. A number of other analytical techniques may be used as known to those skilled in the art. See, e.g., Tinoco et al., 3 Anal. Biochem. 514 (1962); CANOLA: CHEMISTRY, PRODUCTION, PROCESSING & UTILIZATION (Daun et al., eds., AOCS Press, Urbana, IL, 2011) (Daun et al., 2011); US 2015/0166928; US 20160002566.

The lipid or oil of NS-B50027-4 seed may also be purified or enriched to increase the proportion of TAG, for example by removal of free fatty acids or phospholipids. In at least one embodiment, lipid of NS-B50027-4 seed is in the form of an oil, in which at least 75%, at least 80%, at least 85%, at least 90%, at least 95%, at least 98%, inclusive, or between about 95% and 98%, inclusive by weight of the lipid in is in the form of TAG.

In a further embodiment, the lipid from NS-B50027-4 seed (or progeny thereof) is processed to increase the amount of DHA as a percentage of the total fatty acid content. For example, the treatment may comprise transesterification. For example, the lipid may be treated to convert the fatty acids in the oil to alkyl esters such as methyl or ethyl esters, which may then be fractionated to enrich the lipid or oil tor the DHA. In embodiments, the fatty acid composition of the lipid after such enrichment comprises at least 40%, at least 50%, at least 60%, at least 70%, at least 80%, or at least 90% DHA. Similarly, because lipid from NS-B50027-4 seed comprises a larger proportion of ALA than typical canola, lipid from NS-B50027-4 seed may be processed to enrich the lipid for ALA content. Additionally, the fatty acid may be in a mixture of fatty acids having a fatty acid composition as described herein, or may be enriched so that the fatty acid comprises at least 40% or at least, 90% of the fatty acid content of the mixture. In an embodiment, the fatty acid is non-esterified. Alternatively, the fatty acid is esterified such as, for example, to a methyl, ethyl, propyl or butyl group.

Despite having lower oleic acid content than oils alleged to lend stability to DHA and other LC-PUFAs via high oleic acid content, LC-PUFA ω3 fatty acid oil from the seed of NS-B50027-4 exhibit surprising stability. More specifically, LC-PUFA ω3 fatty acids are notoriously unstable and particularly susceptible to oxidation. It is understood in the art that encapsulation, blending with other oils, particularly high oleic acid oils, or adding antioxidants are required to extend the shelf life of LC-PUFAs and foods containing LC-PUFAs. Despite a lack of such treatments, however, evidence suggests that oil extracted from crushed NS-B50027-4 seed retains freshness for months at room temperature. Additionally, the levels of nutrients such as phytosterols, vitamin E, vitamin K1, β-carotene, and minerals of NS-B50027-4 oil fall within the natural range of other commercial canola oils. There have been no detectable levels of undesirable substances, such as pesticides, mycotoxins, or polyaromatic hydrocarbons found in oil obtained from NS-B50027-4. Further, no plant DNA has been detected in oil obtained from NS-B50027-4.

Another aspect of the present embodiments provides a source of DHA and LC-PUFA for use in nutritional supplements and food for humans and non-human animals. In particular, oil from NS-B50027-4 seed provides a sustainable source of DHA and LC-PUFA for use in aquaculture. Due to the high global demands for fish and the resulting overfishing of the seas, marine and freshwater aquaculture has taken on increasing importance. See, e.g., Betancor et al., 4 Sci. Rep. 8104 (2014). For example, farming and consumption of salmonids has dramatically increased during the past 20 years. The diet of wild fish is very different from that of their fellow species in aquaculture, however. In fact, aquaculture is still highly dependent upon marine-capture fisheries to provide key dietary nutrients, such as fish meal and fish oil. Indeed, fish oil is the primary source of ω3-LC PUFA in aquaculture. Because marine fish oils comprise a limiting factor for the strongly growing fish farming industry (5% to 10% per annum), aquaculture diets contain a wide variety of alternative plant-based ingredients such as legume seeds, oilseed cake, leaf meal, and an increasing portion of vegetable oil in addition to animal-derived oil. Replacing fish oils with vegetable oils which are traditionally low in LC-PUFA means that less LC-PUFA are available in the fish diet, even though some oils such as flaxseed oil contain a quantity of ALA that can be converted, albeit only to a limited extent, into LC metabolites in fishes. In general, current vegetable oils in fish feed can have a detrimental effect on the FA distribution in fish, and they can alter the ω3/ω6 ratio and reduce the total LC-PUFA in the fish flesh.

For example, typical vegetable oils contain high amounts of ω6 PUFA, mainly as linoleic acid (C18:2 ω6; LA). Oil from the parent line AV Jade has a DHA:LA ratio of 0.016; oil from NS-B50027-4 has a DHA:LA ratio of 1.048; compared with oil from farm-raised salmon having a DHA:LA ratio of 0.908. Strobel et al., 11 Lipids Health Dis. 144 (2012). Interestingly, the ratios of ω3 FAs from NS-B50027-4 are particularly advantageous regarding palmitic acid, a saturated fatty acid associated with cardiovascular disease and dyslipidemia. *Diet, Nutrition & Prevention of Chronic Dis.*, WHO Tech. Rep. Series 916, Report of a Joint WHO/FAO Expert Consultation, 88 (World Health Organization, Geneva, 2003). Oil from the parent line AV Jade has a no DHA; an example oil from NS-B50027-4 has a DHA:palmitate ratio of about 2.12; compared with oil from farm-raised salmon having a DHA:palmitate ratio of about 0.59; and oil from wild salmon has a DHA:palmitate ratio of about 1.028. Strobel et al., 2012. The preparation of foodstuffs for use in aquaculture including LC-PUFAs is otherwise known in the art. See Betancor et al., 2014; Petrie et al., 9 PLOS ONE 1, 2014; Tocher, 449 Aquaculture 94 (2015).

Therefore, the scope of the present embodiments encompasses the use of oil from NS-B50027-4 as a source of ω3 fatty acids for aquaculture feed, and an aquaculture feed comprising oil obtained from NS-B50027-4 and its progeny. Studies with oil obtained from NS-B50027-4 have shown this oil is safe for inclusion in feed provided to freshwater salmon (2 gram to 25 gram fingerlings), and that EPA and DHA from NS-B50027-4 oil-containing feed was incorporated into salmon flesh.

Figure 4:
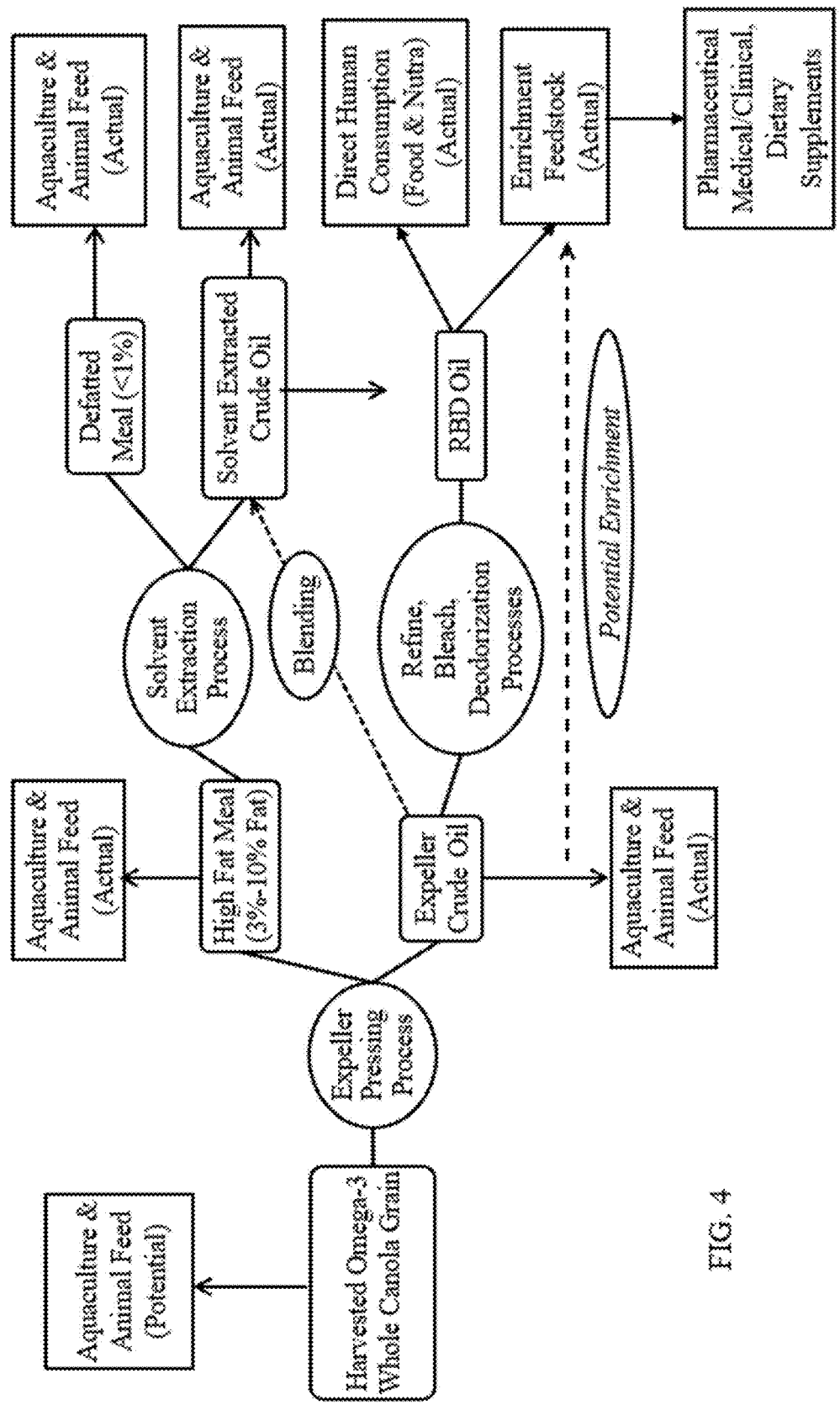
FIG. 4 is a flow diagram depicting possible processing and product streams from harvested transgenic canola seed that contains ω3 fatty acids. Rounded-edged rectangles indicate products or process fractions; ovals indicate processing steps; sharp-cornered rectangles indicate possible product usage.

In another aspect, the present embodiments provide compositions comprising one or more of the lipid, oil, fatty acid, seed, seed meal, protein, cell, oilseed plant, or plant part of NS-B50027-4. In some embodiments, the composition further comprises a carrier suitable for pharmaceutical, food, or agricultural use, a seed treatment compound, a fertilizer, another food or feed ingredient, or added protein or vitamins. FIG. 4 provides a diagram of possible processing steps, products or fractions from various process steps, and proposed uses for such fractions or products.

Also provided are foodstuffs, cosmetics, or chemicals comprising one or more of the lipid or oil obtained from NS-B50027-4, the fatty acid obtained from NS-B50027-4, the cell obtained from NS-B50027-4, the oilseed plant, seed meal, or other composition obtained or derived from NS-B50027-4. Another aspect provides a method of producing a foodstuff, the method comprising mixing one or more of lipid or oil of NS-B50027-4 or progeny thereof, fatty acid of NS-B50027-4 or progeny thereof, a cell, plant part, seed, seed meal, oilseed plant of NS-B50027-4 or progeny thereof, or another composition comprising any of these compositions as obtained or derived from NS-B50027-4 or progeny thereof, with at least one other food ingredient. The method may comprise steps of blending, cooking, baking, extruding, emulsifying, or otherwise formulating the foodstuff, or packaging the foodstuff, or of analyzing the amount of lipid or oil in the foodstuff.

The foodstuff envisioned herein comprises oil, lipid, fatty acid ester, or fatty acid produced directly or indirectly by use of the methods, cells, plants, or seed disclosed herein, i.e., the oil from NS-B50027-4 seed or from seed obtained from progeny derived from NS-B50027-4 comprising at least one locus from NS-B50027-4. Foodstuffs include food or preparations for human or animal consumption which when taken into the body nourish or build up tissues, or supply energy; or maintain, restore or support adequate nutritional status for metabolic function. Foodstuffs include nutritional compositions for babies or young children such as, for example, infant formula, and seed meal. Foodstuffs also include food additives such as nutritional supplements. Additionally, the foodstuff may include edible macronutrients, protein, carbohydrate, vitamins, or minerals in amounts suitable for a particular use. The amounts of these ingredients varies depending on whether the composition is intended for use with normal individuals or for use with individuals having specialized needs, such as individuals suffering from metabolic disorders and the like. The foodstuff may either be in a solid, liquid, gel, or emulsion form. The foodstuff can be added to food of any type for any suitable purpose, i.e., it is not required to be added for strictly nutritional purposes.

The foodstuff envisioned herein also comprises crushed canola, canola seed meal, or the protein processed therefrom (i.e., meal, cake, or meal protein) from seed of NS-B50027-4 or progeny derived from NS-B50027-4, comprising at least one locus from NS-B50027-4. Current use of canola meal in specific high-value manufactured feeds is often restricted due to a range of issues including anti-nutritional factors, high fibre content, limited digestibility, and absence of ω3-FA or LC-PUFA, or low density source of protein. Processing the meal cake fraction of canola seed to concentrate canola protein may eliminate such issues, such that canola protein obtained from seed of NS-B50027-4 or its progeny offers a suitable replacement for fishmeal, canola meal, soy meal, or soy protein concentrate, as well as a range of other widely used feed ingredients. For example, shrimp require ten essential amino acids. Canola has a suitable balance of amino acids for shrimp. Four fatty acids are essential for shrimp: LA, ALA, and more importantly, EPA and DHA. The ratio of ω3 to ω6 fatty acids is also important in shrimp feed, with the optimum ω3:ω6 ratio about 2.5. Total lipid feed inclusion of 4.5% to 7.5% is considered optimal. The inclusion of some oil in meal-derived protein from the canola lines described herein would prove advantageous. Moreover, apparent crude protein digestibility for shrimp is high at over 80%; and historically, studies have indicated that protein from plants is less digestible than the protein derived from fish meal. Through protein fractionation and concentration of protein processed from cake meal from canola described herein, the digestibility is expected to closely match fishmeal and may be superior to current canola meal. Such protein products may also provide important alternatives to fishmeal in feed for aquaculture and terrestrial animals.

In another aspect, the present NS-B50027-4 provides a method of treating or preventing a condition that would benefit from a PUFA such as ω3-fatty acid or DHA, the method comprising administering to a subject one or more of the lipid or oil obtained from NS-B50027-4, the fatty acid obtained from NS-B50027-4, the cell obtained from NS-B50027-4, the oilseed plant, seed meal, or other composition obtained or derived from NS-B50027-4. Another aspect provides a method of producing a medicament, the method comprising mixing one or more of lipid or oil of NS-B50027-4, fatty acid of NS-B50027-4, cell according NS-B50027-4, oilseed plant of NS-B50027-4, plant part of NS-B50027-4, seed of NS-B50027-4, seed meal of NS-B50027-4, or another composition comprising any of these compositions as obtained or derived from NS-B50027-4 or progeny thereof; which medicament can be administered in the form of a pharmaceutical composition comprising an ethyl ester of the PUFA. The subject may be a human or non-human animal.

Examples of conditions that may benefit from ω3 fatty acid include elevated serum triglyceride levels, elevated serum cholesterol levels such as elevated LDL cholesterol, cardiac arrhythmias, high blood pressure, coronary heart disease, restenosis after angioplasty, inflammation, asthma, rheumatoid arthritis, ulcerative colitis, Crohn's disease, psoriasis, eczema platelet aggregation, gastrointestinal bleeding, endometriosis, premenstrual syndrome, kidney stones, fetal alcohol syndrome, attention deficit hyperactivity disorder, unipolar depression, bipolar depression, aggressive hostility, schizophrenia, adrenoleukodystophy, hypertension, diabetes, obesity, osteoporosis, Alzheimer's disease, chronic obstructive pulmonary disease multiple sclerosis, cystic fibrosis, phenylketonuria, myalgic encephalomyelitis, acquired immunodeficiency disorder, chronic fatigue after viral infection, cancer, or ocular disease.

The production of the medicament may comprise mixing the oil obtained from NS-B50027-4 with a pharmaceutically acceptable carrier, for treatment of a condition as exemplified herein. The method may comprise purifying the oil, or transesterification or fractionation of the oil to increase the level of DHA. In a particular embodiment, the method comprises treating the lipid or oil to convert the fatty acids in the oil to alkyl esters such as methyl or ethyl esters. Further treatment such as fractionation or distillation may be applied to enrich the lipid or oil for DHA. In an example embodiment, the medicament comprises ethyl esters of DHA. The level of ethyl esters of DHA in the medicament may be between about 30% and about 50%, inclusive, or at least 80%, at least 85%, at least 90% or at least 95%, inclusive, of the medicament, or of the fatty acid component of the medicament. The medicament may further comprise ethyl esters of EPA or DPA, such as between 30% and 50%, inclusive, or at least 90% of the total fatty acid content in the medicament. The medicament may further comprise ethyl esters of ALA, EPA or DPA, such that ω3 fatty acid content is between about 30% and about 50%, inclusive, or at least 90% of the total fatty acid content in the medicament. Such medicaments are suitable for administration to human or animal subjects as determined by a health care professional. The formulation of pharmaceutical compositions comprising fatty acid is known in the art. Additionally, as is known in the art, a minimum of about 300 mg per day of ω3 fatty acid, especially ω3 LC-PUFA, such as EPA, DPA or DHA, is desirable; but dosages from 0.1 mg to 20 g per day, or more, of a particular fatty acid may be appropriate as advised by a health care professional.

Additionally, the oil obtained from NS-B50027-4 can be used for cosmetic purposes: it may be added to pre-existing cosmetic compositions such that a mixture is formed, or a fatty acid produced as described herein may be used as an "active" ingredient in a cosmetic composition. See, e.g., US 2008/0241082.

Additionally, techniques that are routinely practiced in the art can be used to extract, process, and analyze the oils produced primarily in the seed of NS-B50027-4. Oil can be obtained by cold-pressing, aqueous treatment, or by more typical processing. See, e.g., Mansour et al., 6 Nutrients 776 (2014); U.S. Pat. No. 6,599,513. For example, NS-B50027-4 seed can be cold-pressed (e.g., via screw press) and the oil filtered; and the remaining meal cake can be extracted with hexane to obtain additional oil from the crushed/pressed canola seed.

In processed food production, for example, canola seed is cooked, pressed, and extracted to produce crude oil that is then degummed, refined, bleached, and deodorized. Various steps can be conducted under nitrogen atmosphere. Generally, techniques for crushing seed are known in the art. For example, oilseed may be tempered (if needed) by spraying with or soaking in water to raise the seed moisture content to, for example, 7% to 8.5%. The tempered seed is flaked, for example, using a smooth roller with a gap setting of 0.23 to 0.27 mm. Heating may be applied to deactivate enzymes, rupture cells, coalesce oil droplets, and agglomerate protein particles. The majority of seed oil is released by pressing, via passage through a screw press, which yields processed seed meal ("cake") and pressed crude oil. Crude oil produced by the pressing operation can be clarified by passage through a settling tank with a slotted wire drainage top to remove the solids that are expressed with the oil during the pressing operation. This clarified oil can be streamed through a plate and frame filter to remove any remaining fine solid particles. Cake expelled from the screw press often contains significant oil, which can be solvent-extracted, for example, with hexane, using, for example, a heat traced column, to obtain additional oil from the seed meal. Once the solvent is stripped from the crude oil obtained from the cake, then pressed and extracted oils can be combined and subjected to further oil processing procedures. For example, the extracted lipid or oil may be subjected to one or more processing steps to increase the purity of the lipid/oil component. For example, purification steps may comprise treating the extracted crude oil with at least one of degumming, deodorizing, decolorizing, drying, fractionating, or fortifying with antioxidants (e.g., mixed tocopherols).

Degumming is an early step in refining oils and primarily serves to remove most of the phospholipids from the oil, which may be present as about 1% to 2% of the total extracted lipid. Addition of water, typically 2% containing phosphoric acid to the crude oil at 70° C. to 80° C. results in the separation of most of the phospholipids, trace metals, pigments, and insoluble lecithin. Degumming can also be performed by adding concentrated phosphoric acid to the crude seedoil to convert non-hydratable phosphatides to a hydratable form, and to chelate minor metals that are present. Gum is separated from the seedoil by centrifugation.

Alkali refining, sometimes also referred to as neutralization, usually follows degumming and precedes deodorizing and bleaching. More specifically, following degumming the seedoil is titrated with a sufficient amount of an alkali solution to neutralize free fatty acid and phosphoric acids, and separate the triglyceride fraction. Suitable alkaline materials include sodium hydroxide, potassium hydroxide, sodium carbonate, lithium hydroxide, calcium hydroxide, calcium carbonate and ammonium hydroxide. Soap is removed by centrifugation or by extraction, into a solvent for the soap, and the neutralized oil is washed with water. If required, any excess alkali in the oil may be neutralized with a suitable acid such as hydrochloric acid or sulfuric acid.

Some plant oil, such as soybean oil, is processed by a combination of degumming and neutralization. For the conditioning of the nonhydratable phosphatides, a small quantity of phosphoric or citric acid is added to the crude non-degummed oil. After intensive mixing, diluted caustic soda (7% and 12%) is added to neutralize the free fatty acids. Adequate water hydrates the phosphatides in the presence of the caustic. Following the reaction time in a retention mixer, the oil is heated and sent directly to a separator to separate the soapstock. The neutral oil is washed in about 3% to 10% water to reduce the residual soap content, and the mixture is separated into wash water and oil. Residual humidity of the oil is reduced in a vacuum drier.

Deodorization is treatment of oils and fats at a high temperature (200° C.-260° C.) and low pressure (0.1-1 mm Hg), typically achieved by introducing steam into the seedoil at a rate of about 0.1 mL/minute/100 mL of seedoil. After about 30 minutes of such sparging, the seedoil is cooled under vacuum. The seedoil is typically transferred to a glass container and flushed with argon before being stored under refrigeration. This treatment also improves the color of the seedoil, and removes a majority of the volatile or odorous compounds, including any remaining free fatty acids, monoacylglycerols, or oxidation products.

Bleaching is a refining process in which oils are heated at 90° C. to 120° C. for 10 to 30 minutes in the presence of (e.g., 0.2% to 2.0%) of a bleaching earth (e.g., TRISYL® Silicas, W.R. Grace & Co., Columbia, Md., US), and in the absence of oxygen (by operating under nitrogen or in a vacuum). This step removes unwanted pigments (carotenoids, chlorophyll, gossypol, etc.), as well as oxidation products, trace metals, sulphur compounds, and traces of soap. "RDB oil" refers to oil that has been refined, deodorized, and bleached.

Winterization is a process sometimes used in commercial production of oils for the separation of oils and fats into solid (stearin) and liquid (olein) fractions by crystallization at sub-ambient temperatures. Some vegetable oils, such as sunflower or corn oil, contain waxes (esters of long-chained fatty alcohols and fatty acid esters) that crystallize at low temperatures and result in turbidity in the oil. Wet winterization in combination with neutralization is suitable for removing these waxes. It was applied originally to cottonseed oil to produce a solid-free product, and can also be used to decrease the saturated fatty acid content of oils.

Transesterification in a process that exchanges the fatty acids within and between TAG or transfers the fatty acid to another alcohol to form an ester. This may initially involve releasing fatty acids from TAG as free fatty acids or it may directly produce fatty acid esters, such as fatty acid methyl esters or ethyl esters. In a transesterification reaction of TAG with an alcohol, such as methanol or ethanol, the alkyl group of the alcohol forms an ester linkage with the acyl groups (including DHA) of the TAG. When combined with a fractionation process, transesterification can be used to modify the fatty acid composition of lipids. Marangom et al., 6 Trends Food Sci. Technol. 329 (1995). Transesterification can use chemical means (e.g., strong acid- or base-catalyzed) or enzymatic means, the latter using lipases that may be position-specific (sn-1/3- or sn-2-specific) for the fatty acid of the TAG, or having a preference for some fatty acids over others. Adamczak, 13 Pol. J. Food Nutr. Sci. 3 (2004); Ferreira-Dias Elec. 16 J. Biotechnol. (2013).

Alternatively, purification steps can avoid transesterification processes or other processes that alter the fatty acid content of the lipid or oil so as to increase the DHA content as a percentage of the total fatty acid content. In other words, the fatty acid content/profile of a purified lipid or oil obtained from the seed of NS-B50027-4 or its progeny may be essentially the same as that of the unpurified lipid or oil.

Optionally, fatty acid fractionation to increase the concentration of LC-PUFA in oil can be achieved by any of the methods known in the art, such as, for example, freezing crystallization, complex formation using urea, molecular distillation, supercritical fluid extraction, counter current chromatography and silver ion complexing. Complex formation with urea is a preferred method for its simplicity and efficiency in reducing the level of saturated and monounsaturated fatty acids in the oil. Gamez et al., 36 Food Res. Int'l 721 (2003). Initially, TAGs of the oil are split into their constituent fatty acids, often in the form of fatty acid esters, by lipases, or by hydrolysis under either acid or base catalyzed reaction conditions, whereby one mol of TAG is reacted with at least 3 mol of alcohol (e.g., ethanol for ethyl esters or methanol for methyl esters) with excess alcohol enabling separation of the formed alkyl esters and the formed glycerol. The free fatty acids or fatty acid esters are usually unaltered in fatty acid composition by the treatment, and may then be mixed with an ethanolic solution of urea for complex formation. The saturated and monounsaturated fatty acids complex easily with urea and crystallize out on cooling and may subsequently be removed by filtration. The completed non-urea fraction is thereby enriched with LC-PUFA.

As noted, various or multiple steps can be practiced under nitrogen, other inert atmosphere, or vacuum, and the desired oil or lipid obtained from the seed of NS-B50027-4 or its progeny can be packaged under nitrogen, inert gas, or vacuum to avoid oxidation.

Also as noted herein, crushed canola, seed meal, or protein processed therefrom (i.e., meal, cake, or meal protein) from seed obtained from NS-B50027-4 its progeny can be used for food or feed. The high DHA pressed cake can be used as high-oil cake, or be defatted with hexane to prepare meal. Hexane-treated meal is typically desolventized and toasted (DT-meal).

Identification of NS-B50027-4 and Progeny Thereof

An elite genetic event can be characterized by the location(s) and the configuration at the site(s) of incorporation of the recombinant DNA molecule(s) in the plant genome. The site in the plant genome where a recombinant DNA cassette has been inserted is also referred to as the "insertion site" or "target site." A "flanking region" or "flanking sequence" is a region of DNA, for example, at least 20 base pairs, at least 50 base pairs, or up to 5,000 base pairs of the plant genome located either immediately upstream of and contiguous with, or immediately downstream of and contiguous with, the transgenic cassette. Transformation that leads to random integration of the foreign DNA results in transformants with different flanking regions, which are characteristic and unique for each transformant (elite event).

Another aspect provides a method for producing a NS-B50027-4-derived *Brassica napus* plant, or parts thereof comprising crossing the *B. napus* plant, or parts thereof, described above, with a second plant to produce a first generation progeny seed; growing said first generation progeny seed to produce an F2 generation plant; optionally, repeating the steps of crossing and growing to obtain successive filial generations of said seed to obtain a breeding line NS-B50027-4-derived *B. napus* seed, plant, or parts thereof. The plant or plant parts (including any hybrid) produced by this method are also provided. In an embodiment, a genetic trait that has been engineered into the genome of a particular canola plant may be moved into the genome of another cultivar using traditional breeding techniques that are well known in the plant breeding arts. For example, a backcrossing approach may be used to move a transgene from a transformed canola cultivar into an already developed canola cultivar, and the resulting backcross conversion plant would then comprise the transgene(s).

Accordingly, another aspect of the present embodiments provides compositions, methods, and kits for detection of NS-B50027-4. It would be advantageous to be able to detect the presence of a particular event in order to determine whether progeny of a sexual cross contain a transgene of interest. In addition, a method for detecting a particular event would be helpful for complying with regulations requiring the premarket approval and labeling of foods derived from recombinant crop plants, for example. It is possible to detect the presence of a transgene by any well-known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different events, particularly those produced using the same DNA construct unless the sequence of chromosomal DNA adjacent to the inserted DNA ("flanking DNA") is known. Event-specific PCR assays have been described. See, e.g., Windels et al., Med. Fac. Landbouw, Univ. Gent 64/5b: 459 (1999) (identifying glyphosate-tolerant soybean event by PCR using primer set spanning junction: first primer included sequence from insert and second primer included sequence from flanking DNA). Additionally, the sixteen-gene insert of NS-B50027-4 disrupted the expression of the *Brassica* gene encoding the Pto-interacting protein (PTI), a serine-threonine kinase involved in the hypersensitive response-mediated signaling located on chromosome A05. Although no phenotypic change was observed, this provides another marker for identification of NS-B50027-4 or NS-B50027-4-derived progeny.

Methods and kits herein are useful for identifying in biological samples the presence of plant material comprising specifically the transgenes in NS-B50027-4, as well as transgenic canola plants, plant materials, and seeds containing such event. The elite event NS-B50027-4 described herein can be identified by genotype, which can be characterized through a genetic marker profile that can identify plants of the same cultivar or a related cultivar or be used to determine or validate a pedigree. Genetic marker profiles can be obtained by techniques such as Restriction Fragment Length Polymorphisms (RFLP), Randomly Amplified Polymorphic DNAs (RAPD), Arbitrarily Primed Polymerase Chain Reaction (AP-PCR), DNA Amplification Fingerprinting (DAF), Sequence Characterized Amplified Regions (SCAR), Amplified Fragment Length Polymorphisms (AFLP), Simple Sequence Repeats (SSR) (also referred to as Microsatellites), and Single Nucleotide Polymorphisms (SNP).

For example, the elite event NS-B50027-4 described herein can be identified by generation of a genetic map from a sample of plant material. A genetic map can be generated by conventional RFLP, Polymerase Chain Reaction (PCR) analysis, or SSR which identifies the approximate chromosomal location of the integrated DNA molecule coding for the foreign protein. See Glick & Thompson, METHODS IN PLANT MOLEC. BIOL. & BIOTECHNOL. 269 (CRC Press, Boca Raton, FL, 1993). Map information concerning chromosomal location is useful for proprietary protection of a subject transgenic plant. For example, the map of the integration region can be compared to similar maps for suspect plants to determine if the latter have a common parentage with the subject plant. Map comparisons can involve hybridizations, RFLP, PCR, SSR and sequencing, all of which are conventional techniques.

Another aspect of the present embodiments provides kits and methods for determining whether a canola plant is or is related to inbred line NS-B50027-4, or a canola plant that comprises at least part of genetic elite event of line NS-B50027-4. Compositions and method for simple and unequivocal techniques for identification of elite event NS-B50027-4 in biological samples are described herein.

For example, a kit can include at least one set of primers for identification of one or more genetic markers of NS-B50027-4, such as a set of sense (forward) and antisense (backward) primers. Specific embodiments of primers include the following primers useful in kits for conducting KASP assays to detect NS-B50027-4 genetic traits, particularly useful in introgression studies and hybrid development. See Example 2. These primers may consist of a nucleic acid molecule comprising at least ten consecutive nucleic acids of a sequence shown in SEQ ID NO:1 to SEQ ID NO:90 (see Table 14, Example 3), or complements thereof.

The present invention also provides methods for identifying an elite event NS-B50027-4 canola plant, comprising: (a) forming a mixture comprising a biological sample containing canola plant DNA and a first and second nucleic acid primer capable of amplifying an event-NS-B50027-4-specific nucleic acid molecule; (b) reacting the mixture under conditions that allow the first and second nucleic acid primers to amplify an event NS-B50027-4-specific nucleic acid molecule; and (c) detecting the presence of the amplified fragment nucleic acid molecule, wherein the presence of the canola elite event NS-B50027-4-specific nucleic acid molecule indicates that the canola plant is a NS-B50027-4 canola plant.

Another embodiment provides methods for detecting an elite event NS-B50027-4 nucleic acid molecule in a biological sample comprising: (a) forming a mixture comprising a biological sample containing DNA and a nucleic acid probe capable of hybridizing to an event NS-B50027-4-specific nucleic acid molecule; (b) reacting the mixture under conditions that allow the probe to hybridize to an event NS-B50027-4-specific nucleic acid molecule; and (c) detecting the presence of a hybridized nucleic acid molecule, wherein the presence of the event NS-B50027-4-specific nucleic acid molecule indicates that the sample contains event NS-B50027-4 nucleic acid molecule.

Yet another embodiment provides methods for detecting the presence of an event NS-B50027-4 nucleic acid molecule in a biological sample, comprising: (a) forming a mixture comprising a biological sample containing DNA and a first primer capable of annealing to a region of the event NS-B50027-4 insert nucleic acid molecule and a second primer capable of annealing to a flanking nucleic acid molecule in a host cell genome; (b) reacting the mixture under conditions that allow the first and second nucleic acid primers to produce an amplified nucleic acid molecule comprising a fragment of the event NS-B50027-4 insert nucleic acid molecule; and (c) detecting the presence of the amplified nucleic acid molecule, wherein the presence of the fragment of the event NS-B50027-4 insert nucleic acid molecule indicates that the sample contains event NS-B50027-4 insert DNA.

Proper testing should detect any major faults and establish the level of superiority or improvement over current commercial canola cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs, as well as technical superiority of the final cultivar. For seed-propagated cultivars, it must be feasible to produce seed easily and economically.

Progeny

The line NS-B50027-4 described herein can be used as a parent for breeding other lines. For example, as a source it can be self-pollinated, crossed, backcrossed, used to produce doubled haploids, used as source materials for genetic transformation, or be subjected to genetic transformation, further mutagenized, and used for other forms of breeding as is known to those skilled in the art. The methods and results of using the source material to breed other lines are also within the scope of these embodiments.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Any DNA sequences, whether from a different species or from the same species, which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of the claimed line.

Nucleic acids, oligonucleotides, or polynucleotides refer to RNA or DNA molecules that are linear or branched, single or double stranded, or hybrids thereof—including RNA/DNA hybrids. These terms also encompass 3' UTRs and 5' UTRs, typically at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

Plant transformation involves the construction of an expression vector that will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed canola plants using transformation methods as known in the art to incorporate transgenes into the genetic material of the canola plant(s), including NS-B50027-4 canola plants. For example, a transgene cassette comprising gene(s) encoding glycerol-3-phosphate acyltransferase (GPAT), lysophatidic acid acyltransferase (LPAAT), or diacylglycerol acyltransferase (DGAT) may be transformed into NS-B50027-4 to modify fatty acid or TAG synthesis. See, e.g., Shrestha et al., 7 Front. Plant Sci. 1402 (2016).

A genetic trait that has been engineered into a particular canola plant using transformation techniques could be moved into another line using traditional breeding techniques that are well known in the plant breeding arts. For example, plants harboring elite event NS-B50027-4 can, for example, be obtained from seed deposited at the ATCC®. Such plants can be further propagated or used in a conventional breeding scheme to introduce event NS-B50027-4 (i.e., LC-PUFA biosynthesis) into other cultivars of the same or related plant species. The deposited seeds belong to the species Brassica napus. Nevertheless, methods to introduce alleles or transgenes located on the A-genome or C-genome from B. napus to B. juncea are well known in the art and include repeated back-crossing. A backcrossing approach can be used to move a transgene from a transformed canola plant to an elite inbred line and the resulting progeny comprise the transgene. Also, if an inbred line is used for the transformation, then the transgenic plants can be crossed to a different line in order to produce a transgenic hybrid canola plant. As used herein, "crossing" can refer to a simple X by Y cross, or the process of backcrossing, depending on the context.

Various genetic elements can further be introduced into the plant genome using transformation. These elements include but are not limited to genes; coding sequences; inducible, constitutive, and tissue specific promoters; enhancing sequences; and signal and targeting sequences. The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA molecules, whether from a different species or from the same species, inserted into the genome using transformation are referred to herein collectively as "transgenes". The process of "transforming" is the insertion of DNA into the genome. Several methods for producing transgenic plants have been developed, and the present invention, in particular embodiments, also relates to transformed versions of the claimed canola line NS-B50027-4.

Numerous methods for plant transformation have been developed, including biological and physical, plant transformation protocols. In addition, expression vectors and in vitro culture methods for plant cell or tissue transformation and regeneration of plants are available. See, e.g., Miki et al., Procedures for introducing foreign DNA into plants, in METH. PLANT MOLEC. BIOL. & BIOTECHNOL. at 63 (Glick & Thompson, eds., CRC Press, Boca Raton, 1993); Gruber et al., Vectors for plant transformation, id. at R 89; Genetic transformation for the improvement of Canola, PROC. WORLD CONF. BIOTECHNOL. FATS & OILS INDUS. at 43-46 (Am. Oil. Chem. Soc., Champaign, IL, 1988).

The most prevalent types of plant transformation involve the construction of an expression vector. Such a vector comprises a DNA molecule that contains a coding region under the control of or operatively linked to a regulatory region, for example a promoter. The expression vector may contain one or more genes and one or more regulatory elements. At least one of the coding regions and their respective regulatory elements can be arranged in opposite orientation within the vector, providing a binary vector. In theory, arrangement of genes susceptible to gene silencing in binary fashion may minimize gene silencing. The vector(s) may be in the form of a plasmid, and can be used alone or in combination with other plasmids, to provide transformed canola plants using transformation methods as known in the art to incorporate transgenes into the genetic material of the NS-B50027-4 plant or NS-B50027-4-derived plant.

For example, an initial transformation cassette, pJP3416 GA7-modB, included seven genes capable of promoting the accumulation of omega-3 fatty acids in canola seed, and a selectable marker gene to facilitate the selection of putative transgenic plants in vitro. See WO 2013185184; U.S. Patent Publ'n No. 20150374654; Petrie et al., 6 Plant Meth. 8 (2010). The expressed genes are all synthetic—codon optimized and synthesized—hence the transgenic DNA molecules are not found in any natural organisms. The original DNA sequences that were used as templates for codon optimization have been described. See Petrie et al., 12 Metab. Eng'g 233 (2010a); Petrie et al., 11 Plant Methods 6 (2010b); Petrie et al., 21 Transgenic Res. 139 (2012).

As is well-known in the art, functional gene promoters are regions of DNA that are important for gene transcription, but do not encode functional products such as peptides. For example, a common promoter for constitutive expression is derived from Cauliflower Mosaic Virus. Kay et al., 236 Sci. 1299 (1987); Coutu et al., 16 Transgenic Res. 771 (2007). Promoters under developmental control include promoters that preferentially initiate transcription in certain tissues, such as seeds, leaves, roots, fibers, xylem vessels, tracheids, or sclerenchyma. Promoters of particular relevance are "seed-preferred" promoters that initiate transcription primarily or only in seed. "Seed-preferred" promoters include both "seed-specific" promoters (those promoters active during seed development such as promoters of seed storage proteins) as well as "seed-germinating" promoters (those promoters active during seed germination). See Thompson et al., 10 BioEssays 108 (1989). Such seed-preferred promoters include, but are not limited to, Cim1 (cytokinin-induced message); cZ19B1 (maize 19 kDa zein); milps (myo-inositol-1-phosphate synthase) (see WO 2000/11177 and U.S. Pat. No. 6,225,529). For dicots, seed-specific promoters include, but are not limited to, bean β-phaseolin, napin, β-conglycinin, soybean lectin, cruciferin, conlinin, and the like. The seed-specific promoters used in GA7-modB have been described previously: *A. thaliana* FAE1 (Rossack et al., 46 Plant Molec. Biol. 717 (2001)); *L. usitatissimum* Cnl1 and Cnl2 (Chaudhary et al., WO 2001016340); and truncated *B. napus* napin promoter (Stalberg et al., 23 Plant Molec. Biol. 671 (1993)). See also WO 2013185184.

An "inducible" promoter is a promoter which is under environmental control. Examples of environmental conditions that may affect inducible promoters include anaerobic conditions or the presence of light. Tissue-specific, tissue-preferred, (e.g., seed-specific), and inducible promoters constitute the class of "non-constitutive" promoters. See Ward et al., 22 Plant Mol. Biol. 361 (1993); Meft et al., 90 PNAS 4567 (1993) (copper-inducible); Gatz et al., 243 Mol. Gen. Genet. 32 (1994) (induced by herbicide safeners); Gatz, et al., 227 Mol. Gen. Genet. 229 (1991) (tetracycline-inducible); Schena et al., 88 PNAS 10421 (1991) (glucocorticosteroid-inducible). See also WO 2001016340 and the promoters discussed therein.

A "constitutive" promoter is a promoter which is active under most environmental conditions. Exemplary constitutive promoters include the promoters from plant viruses such as the 35S promoter from Cauliflower Mosaic Virus (CMV) (Odell et al., 313 Nature 810 (1985)) and the promoters from such genes as rice actin (McElroy et al., 2 Plant Cell 163 (1990)); ubiquitin (Christensen et al., 12 Plant Mol. Biol. 619 (1989); Christensen et al., 18 Plant Mol. Biol. 6759 (1992)); pEMU (Last et al., 81 Theor. Appl. Genet. 581 (1991)); MAS (Velten et al., 3 EMBO J. 2723 (1984)) and maize H3 histone (Lepetit et al., 231 Mol. Gen. Genet. 276 (1992); Atanassova et al., 2 Plant J. 291 (1992)). The ALS promoter, XbaI/NcoI fragment 5' to the *Brassica napus* ALS3 structural gene (or a nucleotide sequence similarity to said XbaI/NcoI fragment), provides another constitutive promoter. See also WO 1996/30530 and promoters discussed therein. The CMV promoter is also associated with a useful enhancer region. See, e.g., WO 1996/30530 and WO 2013185184 and promoters discussed therein.

Terminator regions, which include polyadenylation signals, are required for the production of complete and stable mRNA molecules. For example, the *A. tumefaciens* nopaline synthase (NOS) terminator provides a useful terminator. Bevan, 12 Nucl. Acid Res. 8711 (1984); Rogers et al., in BIOTECHNOL. PLANT SCI. at 219 (Acad. Press, Inc., New York, NY, 1985); Sanders et al., 15 Nucl. Acids Res. 1543 (1987). A range of regulatory sequences were used in combination to drive and terminate transcription the various expression cassettes.

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' or 3' region of a gene encoding the protein of interest. Targeting sequences at the 5' or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, e.g., Becker et al., 20 Plant Mol. Biol. 49 (1992); Knox et al., 9 Plant Mol. Biol. 3 (1987); Lerner et al., 91 Plant Physiol. 124 (1989); Fontes et al., 3 Plant Cell 483 (1991); Matsuoka et al., 88 PNAS 834 (1991); Creissen et al., 2 Plant J. 129 (1991); Kalderon et al., 39 Cell 499 (1984); Steifel et al., 2 Plant Cell 785 (1990).

Expression vectors typically include at least one genetic marker, operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. Positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., 80 PNAS 4803 (1983). Another commonly used selectable marker gene is the hygromycin phosphotransferase gene which confers resistance to the antibiotic hygromycin. Vanden Elzen et al., 5 Plant Mol. Biol. 299 (1985). Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., 86 Plant Physiol. 1216 (1988); Jones et al., 210 Mol. Gen. Genet., 86 (1987); Svab et al., 14 Plant Mol. Biol. 197 (1990); Hille et al., 7 Plant Mol. Biol. 171 (1986). Other selectable marker genes confer resistance to herbicides such as glyphosate, glufosinate, or bromoxynil. Comai et al., 317 Nature 741 (1985); Gordon-Kamm et al., 2 Plant Cell 603 (1990); Stalker et al., 242 Sci. 419 (1988). Selectable marker genes for plant transformation that are not of bacterial origin include, for example, mouse dihydrofolate reductase, plant 5-enolpyruvylshikimate-3-phosphate synthase, and plant acetolactate synthase. Eichholtz et al., 13 Somatic Cell Mol. Genet. 67 (1987); Shah et al., 233 Sci. 478 (1986); Charest et al., 8 Plant Cell Rep. 643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS), α-galactosidase, luciferase and chloramphenicol, acetyltransferase. Jefferson, 5 Plant Mol. Biol. 387 (1987); Teeri et al., 8 EMBO J. 343 (1989); Koncz et al., 84 PNAS 131 (1987); DeBlock et al., 3 EMBO J. 1681 (1984). Some in vivo methods for visualizing GUS activity do not require destruction of plant tissues. Molecular Probes, Publication 2908, IMAGENE GREEN, 1-4 (1993); Naleway et al., 115 J. Cell Biol. 151a (1991). In vivo methods for visualizing GUS activity have been problematic, however, exhibiting low sensitivity, high fluorescent backgrounds, and limitations associated with the use of luciferase genes as selectable markers. Green Fluorescent Protein (GFP) can be been utilized as a marker for gene expression in prokaryotic and eukaryotic cells. Chalfie et al., 263 Sci. 802 (1994). GFP and mutants of GFP may be used as screenable markers.

NS-B50027-4 and NS-B50027-4 progeny can further be transformed to confer disease or pest resistance. For example, a plant line can be transformed with a cloned resistance gene to engineer plants that are resistant to specific pathogen strains. See, e.g., Jones et al., 266 Sci. 789 (1994) (cloning of the tomato Cf-9 gene for resistance to *Cladosporium fulvum*); Martin, et al., 262 Sci. 1432 (1993) (tomato Pto gene for resistance to *Pseudomonas syringae* pv. tomato, a protein kinase); Mindrinos et al., 78 Cell 1089 (1994) (*Arabidopsis* RSP2 gene for resistance to *P. syringae*); Geiser et al. 48 Gene 109 (1986) (*Bacillus thuringiensis* δ-endotoxin gene); Van Damme et al., 24 Plant Mol. Biol. 25 (1994), (*Clivia miniata* mannose-binding lectin); Sumitani et al., 57 Biosci. Biotech. Biochem. 1243 (1993) (amylase inhibitor); Abe et al., 262 J. Biol. Chem. 16793 (1987) (cysteine proteinase inhibitor); Huub et al., 21 Plant Mol. Biol. 985 (1993) (tobacco proteinase inhibitor I); Regan, 269 J. Biol. Chem. 9 (1994) (insect diuretic hormone receptor); Pratt et al., 163 Biochem. Biophys. Res. Comm. 1243 (1989) (allostatin); Tomalski et al., U.S. Pat. No. 5,266,317 (insect-specific, paralytic neurotoxins); Scott et al., WO 1993/02197 (callase gene); Kramer et al., 23 Insect Biochem. Mol. Biol. 691 (1993) (tobacco hornworm chitinase); Kawalleck et al., 21 Plant Mol. Biol. 673 (1993) (parsley ubi4-2 polyubiquitin gene); WO 1995/16776 (derivatives of tachyplesin inhibit fungi); WO 199518855 (synthetic antimicrobial peptides); Jaynes et al., 89 Plant Sci. 43 (1993) (cecropin-β, lytic peptide renders transgenic tobacco plants resistant to *Pseudomonas solanacearum*); Botella et al., 24 Plant Mol. Biol., 24:757 (1994) (mung bean calmodulin); Griess, et al., 104 Plant Physiol. 1467 (1994) (maize calmodulin); Taylor, et al., Abstract #497, 7th Int'l Symp. Molec. Plant-Microbe Interactions (Edinburgh, Scotland (1994) (enzymatic inactivation in tobacco via transgenic single-chain antibody); Tavladoraki et al., 366 Nature 469 (1993) (viral resistance via transgenic antibody); Lamb et al., 10 Bio technol. 1436 (1992) (fungal endo-α-1, 4-D-polygalacturonase fragments facilitate fungal colonization and plant nutrient released by solubilizing plant cell wall homo-α-1,4-D-galacturonase; Toubart et al., 2 Plant J. 367 (1992) (bean endopolygalacturonase-inhibiting protein); Logemann et al., 10 Bio/technology 305 (1992) (transgenic plants expressing barley ribosome-inactivating gene have increased resistance to fungal disease).

As noted, herbicide resistance is another useful trait that can be introduced by genetic modification. For example, resistance to herbicides that inhibit the growing point or meristem, such as an imidazolinone or a sulfonylurea, can be conferred by mutant ALS and AHAS enzymes. See, e.g., Lee et al., 7 EMBO J. 1241 (1988); Miki et al., 80 Theor. Appl. Genet. 449 (1990); glyphosate resistance is conferred by mutant 5-enolpyruvlshikimate-3-phosphate synthase (EPSPS) and aroA genes; glufosinate resistance is conferred by phosphinothricin acetyl transferase genes; and ACCase inhibitor-encoding genes confers resistance to pyridinoxy or phenoxy propionic acids and cyclohexones. See, e.g., U.S. Pat. No. 4,940,835 (EPSPS confers glyphosate resistance); mutant aroA gene, ATCC® Accession No. 39256, see Comai, U.S. Pat. No. 4,769,061; see also Umaballava-Mobapathie, 8 Transgen. Res. 33 (1999) (*Lactuca sativa* resistant to glufosinate); Kumada et al., EP 0 333 033; Goodman et al., U.S. Pat. No. 4,975,374 (glutamine synthetase genes confer resistance to herbicides such as L-phosphinothricin); Leemans et al., EP 0242246 (phosphinothricin-acetyl-transferase); DeGreef et al., 7 Bio/technol. 61 (1989) (chimeric bar genes encoding phosphinothricin acetyl transferase); Marshall et al., 83 Theor. Appl. Genet. 435 (1992) (Acc1-S1, Acc1-S2, and Acc1-S3 genes confer resistance to phenoxy propionic acids and cyclohexones, such as sethoxydim and haloxyfop); Przibilla et al., 3 Plant Cell 169 (1991) (PsbA and gs$^+$ genes confer triazine resistance); Stalker, U.S. Pat. No. 4,810,648 (nitrilase genes confer benzonitrile resistance); Hayes et al., 285 Biochem. J. 173 (1992) (glutathione S-transferase); Hattori et al., 246 Mol. Gen. Genet. 419 (1995) (acetohydroxy acid synthase confers resistance to multiple herbicides); Shiota et al., 106 Plant Physiol. 17 (1994) (yeast NADPH-cytochrome P450 oxidoreductase); Aono et al., 36 Plant Cell Physiol. 1687 (1995) (glutathione reductase and superoxide dismutase); Datta et al., 20 Plant Mol. Biol. 619 (1992) (various phosphotransferases); WO 01/12825; U.S. Pat. Nos. 6,288,306; 6,282,837; 5,767,373; (plants with altered protox activity are resistant to protox-targeting herbicides).

NS-B50027-4 and NS-B50027-4-derived progeny can further be modified to confer any number of value-added traits as are known in the art. See, e.g., Goto, et al., 521 Acta Horticul. 101 (2000) (soybean ferritin gene); Curtis et al., 18 Plant Cell Rep. 889 (1999) (nitrate reductase); Knultzon et al., 89 PNAS 2625 (1992) (stearyl-ACP desaturase); Shiroza et al., 170 J. Bacteriol. 810 (1988) (nucleotide sequence of *Streptococcus mutans* fructosyltransferase gene); Steinmetz et al., 20 Mol. Gen. Genet. 220 (1985) (*Bacillus subtilis* levansucrase gene); Pen et al., 10 Bio/technol. 292 (1992) (transgenic plants express *Bacillus licheniformis* α-amylase); Elliot et al., 21 Plant Mol. Biol. 515 (1993) (tomato invertase genes); Søgaard et al., 268 J. Biol. Chem. 22480 (1993) (site-directed mutagenesis of barley α-amylase gene); Fisher et al., 102 Plant Physiol. 1045 (1993) (maize endosperm starch branching enzyme II).

Canola line NS-B50027-4 can also be manipulated to be male sterile by any of a number of methods known in the art, including by the use of mechanical methods, chemical methods, self-incompatibility (SI), cytoplasmic male sterility (CMS, either ogura or another system) or nuclear male sterility (NMS). The term "manipulated to be male sterile" refers to the use of any available techniques to produce a male sterile version of canola line NS-B50027-4. The male sterility may be either partial or complete male sterility. See, e.g., WO 2001/29237 (introduction of a deacetylase gene under the control of a tapetum-specific promoter and with the application of the chemical N-Ac-PPT); WO 199213956, WO 199213957 (stamen-specific promoters); Paul et al., 19 Plant Mol. Biol. 611 (1992) (introduction of barnase and the barstar genes); see also U.S. Pat. Nos. 5,859,341; 6,297,426; 5,478,369; 5,824,524; 5,850,014; 6,265,640; Hanson et. al., 16 Plant Cell S154 (2004).

Numerous methods for plant transformation have been developed, including biological and physical, plant transformation protocols. See, e.g., WO 2013185184; Miki et al., in METHS. PLANT MOLEC. BIOL. BIOTECHNOL. at 67-88 (Glick & Thompson, Eds., CRC Press, Inc., Boca Raton, FL, 1993). In addition, expression vectors and in vitro culture methods for plant cell or tissue transformation and regeneration of plants are available. See, e.g., WO 2013185184; Gruber et al., METHS. PLANT MOLEC. BIOL. BIOTECHNOL. at 89-119 (Glick & Thompson, Eds., CRC Press, Inc., Boca Raton, FL, 1993). One method for introducing an expression vector into plants uses the natural transformation system of *Agrobacterium*, see Horsch et al., 227 Sci. 1229 (1985); Curtis et al., 45 J. Exper. Botany 1441 (1994); Tones et al., 34 Plant Cell Tissue Organ Culture 279 (1993); Dinant et al., 3 Molec. Breeding 75 (1997); Kado, 10 Crit. Rev. Plant Sci. 1 (1991) (Ti and Ri plasmids of *A. tumefaciens* and *A. rhizogenes*, respectively, carry genes responsible for genetic transformation of plant); Gruber et al.; Miki et al.; Moloney et al., 8 Plant Cell Rep. 238 (1989) (*Agrobacterium* vector systems, methods for *Agrobacterium*-mediated gene transfer); U.S. Pat. No. 5,591,616.

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 μm to 4 μm. The expression vector is introduced into plant tissues with a biolistic device that accelerates the microprojectiles to speeds of 300 m/s to 600 m/s which is sufficient to penetrate plant cell walls and membranes. Russell et al., 12 Plant Cell Rep. 165 (1993); Aragao et al., 20 Plant Mol. Biol. 357 (1992); Aragao et al., 12 Plant Cell Rep. 483 (1993); Aragao, 93 Theor. Appl. Genet. 142 (1996); Kim & Minamikawa, 117 Plant Sci. 131 (1996); Sanford et al., 5 Part. Sci. Technol. 27 (1987); Sanford, 6 Trends Biotech. 299 (1988); Klein et al., 6 Bio/technol. 559 (1988); Sanford, 7 Physiol. Plant, 206 (1990); Klein et al., 10 Bio/technol. 268 (1992).

Methods for physical delivery of DNA to plants are also known in the art. See, e.g., Zhang et al., 9 Bio/technol. 996 (1991) (sonication); Deshayes et al., 4 EMBO J. 2731 (1985) (liposomes); Christou et al., 84 PNAS 3962 (1987) (spheroplast NHW11915); Hain et al., 199 Mol. Gen. Genet. 161 (1985) (CaCl$_2$ precipitation); Draper et al., 23 Plant Cell Physiol. 451 (1982) (polyvinyl alcohol or poly-L-ornithine); Saker et al., 40 Biologia Plantarum, 507 (1997/98) (electroporation of protoplasts). Additional methods include, but are not limited to, expression vectors introduced into plant tissues using a direct gene transfer method, such as microprojectile-mediated delivery with a biolistic device, DNA injection, electroporation, and the like. Following transformation, expression of the above-described selectable marker genes may allow for preferential selection of transformed cells, tissues or plants, using regeneration and selection methods well-known in the art. See, e.g., WO 2013185184.

The foregoing methods for transformation would typically be used for producing a transgenic line. The transgenic line can then be crossed with another (non-transgenic, mutated, or transformed) line in order to produce a new transgenic canola line. Alternatively, a genetic trait engineered into a particular hybrid *Brassica*, such as *B. napus* or *B. juncea*, using well-known transformation techniques, can be introduced into another line using traditional crossing, backcrossing, and selfing techniques that are also well-known in the plant breeding arts. For example, a backcrossing approach can be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term "NS-B50027-4 plant" is used in the context of the present embodiments, this also includes any gene conversions of that line. The term "gene converted plant" refers to those NS-B50027-4 plants that are developed by backcrossing, genetic engineering, or mutation, wherein essentially all of the desired morphological and physiological characteristics of a variety are recovered in addition to the one or more genes transferred into the NS-B50027-4-derived line via a backcrossing technique, genetic engineering, or mutation. Backcrossing methods can be used with the present embodiments to improve or introduce a characteristic into the plant variety. The term "backcrossing" as used herein refers to the repeated crossing of hybrid progeny back to the recurrent parent, i.e., backcrossing 1, 2, 3, 4, 5, 6, 7, 8, 9, or more times, to the recurrent parent. The parental plant that contributes the gene(s) for the desired characteristic is termed the "nonrecurrent" or "donor parent." This terminology refers to the fact that the nonrecurrent parent is used one time in the backcross protocol and therefore does not recur. The parental *Brassica* or canola plant into which the gene or genes from the nonrecurrent parent are transferred is known as the recurrent parent as it is used for several rounds in the backcrossing protocol. Poehlman & Sleper, 1994; Fehr, 1993. In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a canola or *Brassica* plant is obtained wherein essentially all of the desired morphological and physiological characteristics of the recurrent parent are recovered in the converted plant, in addition to the transferred gene(s) from the nonrecurrent parent. Accordingly, one or two loci from NS-B50027-4 can be transferred into another canola or *Brassica* line.

The selection of a suitable recurrent parent is an important step for a successful backcrossing procedure. The goal of a backcross protocol is to alter or substitute a trait or characteristic in the original line. To accomplish this, a gene of the recurrent parent is modified or substituted with the desired gene from the nonrecurrent parent, while retaining essentially all of the rest of the desired genetic, and therefore the desired physiological and morphological characteristics of the original parent line. The choice of the particular nonrecurrent parent will depend on the purpose of the backcross. A primary purpose of introgression is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Genetic traits may be identified that are not regularly selected in the development of a new line, but that can be improved by backcrossing techniques. Such traits may or may not be transgenic. Examples of these traits include, but are not limited to, male sterility, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. See, e.g., U.S. Pat. Nos. 5,969,212; 7,164,059.

Additionally, reproduction of the inbred line NS-B50027-4 can occur by tissue culture and regeneration. The term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. Tissue culture of various tissues of canola and regeneration of plants therefrom is well-known. See, e.g., Teng et al., 27 HortSci. 1030 (1992); Teng et al., 28 HortSci. 669 (1993); Zhang et al., 46 J. Genet. Breeding 287 (1992); Webb et al., 38 Plant Cell Tissue Organ Cult. 77 (1994); Curtis et al., 45 J. Exp. Bot. 1441 (1994); Nagata et al., 125 J. Am. Soc'y Hort. Sci. 669 (2000); Ibrahim, et al., 28 Plant Cell Tissue Organ Cult. 139 (1992); U.S. Pat. Nos. 5,959,185; 5,973,234; 5,977,445; 8,816,111. Tissue culture as well as microspore culture for regeneration of canola plants can be accomplished successfully. See Chuong et al. 4 Plant Cell Rep. 4 (1985); Barsby et al., 5 Plant Cell Rep. 101 (1986); Kartha et al., 31 Physiol. Plant 217 (1974); Narasimhulu et al., 7 Plant Cell Rep. 104 (1988); Swanson, 6 Meth. Molec. Biol. 159 (1990); *Cell Culture Tech. & Canola Improvement,* 66 J. Am. Oil Chem. Soc. 455 (1989). It is clear from the literature that the state of the art is such that these methods of obtaining plants are used routinely with a high rate of success. Thus, another aspect of the present embodiments provides cells which upon growth and differentiation produce canola plants having the physiological and morphological characteristics of inbred transgenic line NS-B50027-4.

Generally, when the transgene is introduced into a plant through traditional crossing, its insertion site in the plant genome and its flanking regions are not changed. An "insertion region" refers to the region corresponding to a region of at least 40 base pairs, such as at least 100 base pairs, or up to more than 10,000 base pairs, encompassed by the upstream and the downstream flanking regions of a transgene in the (untransformed) plant genome and including the insertion site (and possible target site deletion). Taking into consideration minor differences due to mutations within a species, an insertion region may retain at least 85%, such as 90%, 95%, or 100% sequence identity with the upstream and downstream flanking regions of the foreign DNA in a given plant of that species. Insertion of the transgenic cassette into the plant genome can sometimes be associated, however, with deletion of plant DNA, referred to as "target site deletion." Nevertheless, additional transgenes or other genetic manipulations can be made in NS-B50027-4 without undue experimentation; and NS-B50027-4-derived plants can be identified as described herein.

The source material of NS-B50027-4 can be used to produce lines for hybrid seed production, for example, if it is backcrossed onto a cytoplasmic male sterility source or some other source for sterilizing the inbred line as a female. Alternatively, the line can be used directly. For example, *B. napus* line NS-B50027-4 can be crossed with another canola plant to form a first generation population of F1 plants. The population of first generation F1 plants produced by this method is also an embodiment. This first-generation population of F1 plants comprises an essentially complete set of the alleles of canola line NS-B50027-4. Typically, an F1 hybrid is considered to have all the alleles of each parent. One of ordinary skill in the art can utilize either breeder books or molecular methods to identify a particular F1 plant produced using canola line NS-B50027-4, and any such individual plant is also encompassed by this invention. These embodiments also cover use of these methods with transgenic or single gene conversions of line NS-B50027-4.

Another embodiment provides a method of using canola line NS-B50027-4 in backcrossing to a recurrent parent any number of times. Using the transgenic methods described herein, backcrossing methods, or other breeding methods known to one of ordinary skill in the art, one can develop individual plants and populations of plants that retain at least 25%, 30%, 35%, 40%, 45%, 50%, 55%, 60%, 65%, 70%, 75%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% of the genetic profile of canola line NS-B50027-4. The percentage of the genetics retained in the progeny may be measured by either pedigree analysis or through the use of genetic techniques such as molecular markers or electrophoresis. In pedigree analysis, on average 50% of the starting germplasm would be passed to the progeny line after one cross to another line, 25% after another cross to a different line, and so on. Molecular markers could also be used to confirm and/or determine the pedigree of the progeny line.

A specific method for producing a line derived from canola line NS-B50027-4 is as follows. One of ordinary skill in the art crosses canola line NS-B50027-4 with another canola plant, such as an elite/isogenic line. The F1 seed derived from this cross is grown to form a homogeneous population. The F1 seed contains 50% of the alleles from canola line NS-B50027-4 and 50% of the alleles of the other plant. The F1 seed is grown and allowed to self, thereby forming F2 seed. On average, the F2 seed has derived 50% of its alleles from line NS-B50027-4 and 50% from the other canola plant, but various individual plants from the population have a much greater percentage of their alleles derived from event NS-B50027-4. Wang et al., 40 Crop Sci. 659 (2000); Bernardo et al., 102 Theor. Appl. Genet. 986 (2001). As used in this context, the term population refers to a statistically representative sample. The F2 seed is grown and selection of plants made based on visual observation or measurement of traits. The traits used for selection may be the canola line NS-B50027-4 trait of high DHA production in seeds of the canola. The event NS-B50027-4-derived progeny that exhibits the desired NS-B50027-4-derived trait is selected and each plant is harvested separately. This F3 seed from each plant is grown in individual rows and allowed to self. Then, selected rows or plants from the rows are harvested and threshed individually. The selections are again based on visual observation of plant phenotype, or measurements for desirable traits of the plants, such as the desirable NS-B50027-4-derived trait. The process of growing and selection is repeated any number of times until an inbred NS-B50027-4-derived canola plant is obtained.

NS-B50027-4-derived canola plant contains desirable traits derived from canola line NS-B50027-4, some of which may not have been expressed by the other canola plant to which canola line NS-B50027-4 was crossed and some of which may have been expressed by both canola lines but are now at a level equal to or greater than the level expressed in NS-B50027-4.

NS-B50027-4-derived canola plants have, on average, 50% of their genes derived from NS-B50027-4, but various individual plants from the population have a much greater percentage of their alleles derived from NS-B50027-4. The breeding process, of crossing, self-pollination, and selection is repeated to produce another population of NS-B50027-4-derived canola plants with, on average, 25% of their genes derived from canola line NS-B50027-4, but various individual plants from the population have a much greater percentage of their alleles derived from NS-B50027-4. Another embodiment of the invention is an inbred NS-B50027-4-derived canola plant that has received the desirable NS-B50027-4-derived trait of high DHA.

The previous example can be modified in numerous ways, for instance selection may or may not occur at every self-pollinated generation, selection may occur before or after the actual self-pollination process occurs, or individual selections may be made by harvesting individual pods, plants, rows or plots at any point during the breeding process described. In addition, doubled-haploid breeding methods may be used at any step in the process. The population of plants produced at each and any generation of self-pollination is also an embodiment of the present embodiments, and each such population would consist of plants containing approximately 50% of its genes from canola line NS-B50027-4, 25% of its genes from canola line NS-B50027-4 in the second cycle of crossing, selfing, and selection, 12.5% of its genes from canola line NS-B50027-4 in the third cycle of crossing, selfing, and selection, and so on.

Another embodiment is the method of obtaining a homozygous NS-B50027-4-derived canola plant by crossing canola line NS-B50027-4 with another canola plant and applying doubled-haploid methods to the F1 seed or F1 plant or to any generation of canola line NS-B50027-4 obtained by the selfing of this cross. Pedigree breeding is used commonly for the improvement of self-pollinating crops or inbred lines of cross-pollinating crops. Two parents which possess favorable, complementary traits are crossed to produce an F1. An F2 population is produced by selfing one or several F1's or by intercrossing two F1's (sib mating). Selection of the best individuals is usually begun in the F2 population. Then, beginning in the F3, the best individuals in the best families are selected. Replicated testing of families, or hybrid combinations involving individuals of these families, often follows in the F4 generation to improve the effectiveness of selection for traits with low heritability. At an advanced stage of inbreeding (i.e., F6 and F7), the best lines or mixtures of phenotypically similar lines are tested for potential release as new cultivars.

Still further, the present embodiments are directed to methods for producing NS-B50027-4-derived canola plants by crossing canola line NS-B50027-4 with a canola plant and growing the progeny seed, and repeating the crossing with the growing steps with the NS-B50027-4-derived canola plant from 1 to 2 times, 1 to 3 times, 1 to 4 times, or 1 to 5 times, and selfing any number of times after the first, second, third, fourth, or fifth cross. Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. This process can be used to combine NS-B50027-4 with other LC-PUFA transgenic lines, effectively increasing the copy number in a homozygous line to increase LC-PUFA production in the seed. This technique is advantageous to introduce transgenes to vigorous lines that are not amenable to transformation, or where transgenic loci are known to reside in chromosomes different than those of NS-B50027-4, for example, transgenic locus in A06 can be combined with the NS-B50027-4 loci A02 and A05. A homozygous line from such a cross includes six copies of transgenic inserts. If gene silencing does not suppress expression to an unmanageable effect, LC-PUFA production may be substantially increased. Indeed, a homozygous F4 experimental line comprising six transgenic loci (Full Single x NS-B50027-4) produced about 25% DHA (wt. % of total fatty acid in seed).

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines with each generation due to failure of some seeds to germinate or some plants to produce at least one seed. As a result, not all of the F2 plants originally sampled in the population will be represented by a progeny when generation advance is completed.

A further embodiment provides a single-gene conversion of NS-B50027-4. A gene conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to, fertility modification, fatty acid profile modification, other nutritional enhancements, industrial enhancements, disease resistance, insect resistance, herbicide resistance and yield enhancements. The trait of interest is transferred from the donor parent to the recurrent parent, in this case, the canola plant disclosed herein. Single gene traits may result from the transfer of either a dominant allele or a recessive allele. Selection of progeny containing the trait of interest is done by direct selection for a trait associated with a dominant allele. Selection of progeny for a trait that is transferred via a recessive allele requires growing and self-crossing (selfing) the first backcross to determine which plants carry the recessive alleles. Recessive traits may require additional progeny testing in successive backcross generations to determine the presence of the gene of interest. Along with selection for the trait of interest, progeny are selected for the phenotype of the recurrent parent. It should be understood that occasionally additional polynucleotide sequences or genes are transferred along with the single gene conversion trait of interest. A progeny containing at least 90%, 95%, 96%, 97%, 98%, 99% or 99.5% of the genes from the recurrent parent, the canola plant disclosed herein, plus containing the gene-conversion trait, is considered to be a gene conversion of NS-B50027-4. When a trait is controlled by two genes (e.g., some disease resistance), selection is done for two genes; and so on. A specific aspect of the embodiment described herein provides for use of the four-gene segregant (four-gene locus inserted in chromosome A02) of NS-B50027-4 to increase LC-PUFA production in another transgenic plant.

Mutation breeding is another method of introducing new traits into canola varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. See, e.g., Fehr, PRINCIPLES CULTIVAR DEVEL. (Macmillan Pub'l Co., 1993). For example, mutation could be used to increase the production of DPA in NS-B50027-4 by disrupting expression of the Δ4-desaturase transgene.

It should be understood that the canola line of the present embodiments can, through routine manipulation of cytoplasmic genes, nuclear genes, or other factors, be produced in a male-sterile form as described in the references discussed earlier. Such embodiments are also within the scope of the present claims. The present embodiments thus provide F1 hybrid seed and plants produced by the use of canola line NS-B50027-4. Accordingly, another embodiment provides a method of producing a DHA-containing canola seed by introgressing the DHA trait of NS-B50027-4 into an elite *Brassica* line that is male sterile; introgressing the DHA trait of NS-B50027-4 into a second elite *Brassica* line that is fertile; crossing the two lines to obtain a hybrid progeny; cultivating the seed of the hybrid progeny; harvesting the grain produced by the cultivated hybrid progeny. An additional step of extracting the oil from the progeny of the hybrid seed provides DHA-containing canola oil.

There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLP), Simple Sequence Repeats (SSRs) (also referred to as Microsatellites), and Single Nucleotide Polymorphisms (SNPs). Example 3, herein, provides KASP assays for analysis of NS-B50027-4 and progeny derived therefrom. Primers selected from those provided in SEQ ID NO:1 to SEQ ID NO:90 may also be adapted for other sequence-based techniques.

Isozyme Electrophoresis and RFLPs have been widely used to determine genetic composition. See Shoemaker & Olsen, in GENETIC MAPS: LOCUS MAPS OF COMPLEX GENOMES, at 6.131 (O'Brien, Ed., Cold Spring Harbor Lab. Press, Cold Spring Harbor, N.Y. (1993) (molecular genetic linkage map consisted of 25 linkage groups with ~365 RFLP, 11 RAPD, 3 classical markers, and 4 isozyme loci); see also Shoemaker, in DNA-BASED MARKERS IN PLANTS, 299 (Phillips &Vasil, Eds., Kluwer Acad. Press, Dordrecht, Netherlands, 1994).

SSR technology is currently an efficient and practical marker technology; more marker loci can be routinely used and more alleles per marker locus can be found using SSRs in comparison to RFLPs. See, e.g., Diwan & Cregan, 95 Theor. Appl. Genet. 22 (1997). SNPs may also be used to identify the unique genetic composition of the invention and progeny varieties retaining that unique genetic composition. Various molecular marker techniques may be used in combination to enhance overall resolution. Molecular markers, which include markers identified through the use of techniques such as Isozyme Electrophoresis, RFLP, RAPD, AP-PCR, DAF, SCAR, AFLP, SSR, and SNP, may be used in plant breeding. One use of molecular markers is quantitative trait loci (QTL) mapping. QTL mapping is the use of markers that are known to be closely linked to alleles that have measurable effects on a quantitative trait. Selection in the breeding process is based upon the accumulation of markers linked to the positive effecting alleles or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Thus, it is clear that the state of the art that these methods of obtaining plants are "conventional" in that they are used routinely and have a high rate of success. The utility of canola line NS-B50027-4 also extends to crosses with other species. Commonly, suitable species are of the family Brassicaceae. Accordingly, any and all methods using canola elite event NS-B50027-4 in breeding are encompassed by the present embodiments, including selfing, pedigree breeding, backcrosses, hybrid production and crosses to populations. All plants and populations of plants produced using canola line elite event NS-B50027-4 as a parent are within the scope of these embodiments, including those developed from varieties derived from canola line NS-B50027-4. Unique molecular marker profiles or breeding records can be used by those of ordinary skill in the art to identify the progeny lines or populations of progeny derived from canola line NS-B50027-4. A particular aspect of the present embodiments provides the unexpected advantage in LC-PUFA production in transgenic plants into which the A02 locus segregated from NS-B50027-4 have been introduced by conventional breeding techniques.

EXAMPLES

Example 1. Characterization and Selection of Line NS-B50027-4 in Experimental Field Trials A difficult task in plant breeding is the identification of individual plants that are genetically superior, because for most traits the true genotypic value may be masked by other confounding plant traits or environmental factors. One method for identifying a superior plant is to observe its performance relative to other experimental plants and to one or more widely grown standard cultivars. If a single observation is inconclusive, replicated observations provide a better estimate of the genetic worth.

Plants initially identified as B0050-027-18 were selected based on a single-seed descent procedure by harvesting a sample of one seed per plant, and using the one-seed sample to plant the next generation. In general, the number of plants in a population declines each generation due to failure of some seeds to germinate or some plants to produce at least one seed. As a result, not all of the plants originally sampled in the population are represented by a progeny when generation advance is completed. Moreover, original transgenic events compound the complexity of inheritance, such that predictions are often inaccurate regarding the genotype or phenotype of progeny. Thus, experimental plants were self-pollinated and selected for type for successive generations until a particular line became homozygous, exhibited selected traits with excellent agronomic properties, and produced a uniform population of true-breeding progeny. More specifically, the experimental lines were selected following a breeding re-selection program at the Nuseed Innovation Centre (NIC), Horsham (Victoria, Australia). Selection and advancement of candidate lines was based on:
   (a) Copy number of the T-DNA insert;
   (b) Segregation pattern of DHA expression;
   (c) Homozygosity; (based on fatty acid phenotype and genotype);
   (d) Production of LC-ω3-DHA; and
   (e) Suitable agronomic traits for crop production, based on progeny testing at locations over winter and summer.

In Australia, canola is grown across the southern dryland cropping zone and mostly within winter-dominant rainfall environments. Australian production is mostly from spring type canola cultivars that have low vernalization requirements. In general, Australian cultivars typically retain some minor delay in the onset of flowering and have relatively high plant vigor or biomass production over winter months. The canola crop in Australia is typically sown from April to May after the first major rainfall event and harvested from October to December. Yield is influenced primarily by available water during the growing season and water-use efficiency of the cultivar. Major pathotype gene resistance to blackleg disease, caused by *Leptosphaeria maculans*, can differentiate cultivars in terms of seedling survival and stem cankering, but Australian cultivars are considered generally to have high resistance when grown under recommended agronomic practices. Seed development follows a growing season of five to seven months, and occurs in late spring or early summer. Apart from water availability, yield can be affected significantly by large temperature extremes (<0° C. to >35° C.) that may cause abortion of seed and seed pods.

As noted herein, transformation of canola germplasm was undertaken with an eight-gene construct (seven enzymes for the DHA biosynthetic pathway and a marker) that resulted in seed-specific accumulation of LC-ω3 fatty acids, in particular DHA. Broadly speaking, the phenotype was characterized by product quality (PQ) (omega-3 fatty acids produced), although plants carried a marker gene (MG). Transformed material was reselected for locus homozygosity, expression of DHA in the seed, and agronomic traits and yield potential suitable for commercial production. Test lines were derived from transformed plantlets (var. AV Jade). Experimental seed was bulked by allowing plants to self-pollinate in isolation (i.e., insect-proof tents).

Three T2 generation-derived sibs from a transgenic event were compared with eight other commercial canola cultivars (lines) for a range of important agronomic and seed traits across eight experimental field locations (sites) in Australia (subsequent field trials in Australia and Canada are described further below. The eight Australian sites represented a wide range of environmental yield potentials as indicated by the range in site mean site yield (i.e., AV Garnet: 0.7 to 2.4 t/ha). Transgenic sibs were represented by test lines: NS-B50027-4 (T3), B0050-027-18-36-13 (T4), and B0050-027-18-105-13 (T4). Additionally, NS-B50027-4 was grown in experimental plots in Canada, and agronomic and seed traits compared with non-transgenic canola lines. Additional NS-B50027-4 T3 and T5 generations were also compared with non-transgenic lines and two transgenic segregants out-crossed from NS-B50027-4, each carrying the different transgenic loci (i.e., segregated A05 and A02) (see Example 2). Agronomic trait variation of the test lines was comparable to that of the commercial cultivars evaluated across all environments tested. This conclusion was supported by the finding that the grain yield of the highest yielding test line was statistically comparable, based on an across-site analysis (MET-REML), with the highest yielding commercial cultivars. Furthermore, for each site the highest yielding test line was significantly higher yielding than at least one cultivar, with the exception of one site where there were no significant differences. The test lines produced seed with slightly lower percent seed oil and with varied fatty acid composition; but this did not impact yield or agronomic performance. The expression of LC ω3 DHA fatty acid was highly stable across the tested environments.

The control cultivars (commercial breeding lines) used for comparison provided an agronomically diverse (e.g., plant habit, phenology) range of well-adapted (i.e., high but varying yield potential and oil content) cultivars grown widely in the cropping zone. These cultivars are all open-pollinated and described and extensively evaluated in, for example, the Australian National Variety Testing Program and Regional annual crop reports. See "nvtonline" website. Additionally, variation for plant disease resistance is well-described for blackleg in Australia. Van De Wouw et al., 67 Crop & Pasture Sci. 273 (2015). In Australia, blackleg disease can cause yield losses of up to 90%. Marcroft & Bluett, Agricul. Notes, AG1352, Victoria, Dept. Primary Indus. (2008). Genetic variation among commercial cultivars for specific seed fatty acid composition and seed oil content has been documented over time. See Seberry et al., *Quality of Australian Canola* 2011 (Australian Oilseeds Fed., 2012). Plants from the cultivar AV Jade were transformed to produce the transgenic T0, and hence AV Jade can be considered a non-transformed isoline of the transgenic event described herein.

Phenotypic variation for test lines was characterized by plant emergence, plant vigor, flowering time, flowering duration, plant height, seed shattering, lodging resistance, blackleg severity, plant harvest count, grain yield, grain moisture, percent seed oil, and fatty acid content, particularly seed LC-ω3 polyunsaturated fatty acid (LC-PUFA), specifically concerning yield of EPA, DPA, and DHA. For all the traits measured, restricted estimated likelihood analysis was undertaken using ASREML in statistical software GenStat. Gilmour et al., ASREML user guide, release 3.0, Biometric Bulletin (3) (VSV Intl, Waterhouse Stm Hemel Hempstead, U K, 2009). A linear mixed model statistical method was used to account for field spatial variation as extensively described and used for field plant breeding and genetics research. Cullis & Gleeson, 47 Biometrics 1449 (1991); Smith et al., 57 Biometrics 1138 (2001); Welham et al., *Analysis of linear mixed models by ASReml-R with Applications in Plant Breeding: Course Notes* (VSV Int'l, Waterhouse Stm Hemel Hempstead, U K, 2013). A Meta-REML across-site analysis was further undertaken for grain yield (t/ha) to determine the across-site Best Linear Unbiased Prediction (BLUP) for lines tested.

More frequent and detailed measurements were taken from all environments. Plant emergence establishment counts were made on two random, one square meter quadrants, in each plot, fourteen days after sowing. The number of plants emerged per square meter was analyzed as a trait variate. A plant emergence score based on a visual estimate of average plant density per plot was also recorded for each plot across all sites and analyzed as a trait variate (1: Low=0-5 plants/m$^2$; 5: Moderate=25-30 plants/m$^2$; 9: High=Δ5-50 plants/m$^2$). Plant emergence based on number per square meter and plant emergence score varied significantly (P<0.05) between lines for all eight sites. Statistically variation for plant emergence of the transgenic lines was significantly (P<0.05) within the range expressed by the cultivars across all experiments. Plant vigor was based on biomass, scored on a 1 (low: <10% leaf area coverage of plot ground) to 9 (high: >90% leaf coverage of plot ground cover) scale, and analyzed. Plant vigor varied significantly (P<0.05) between lines for six of seven sites. The site plant mean vigor score was 6 (60% to 70% leaf coverage of plot ground) at all eight sites; and variation was relatively consistent, indicating low environmental effects for this trait. Statistically, the variation for plant vigor for the test lines was significantly within the range expressed by the cultivars across all locations.

Flowering time was recorded as number of days from sowing to when 50% of plants in the experimental plot had at least one open flower. This was recorded for each plot across all trials and analyzed as a trait variate. Flowering varied significantly (P<0.05) between lines for all sites. The site mean flowering time varied from 99 to 110 days and is an indication of environmental differences across experimental sites for this trait. Statistically the variation for flowering time of the transgenic lines was significantly within the range expressed by the cultivars across all experiments.

Flowering duration was the calculated difference between flowering time and end of flowering time (expressed as number of days). This was calculated for each plot across all trials and analyzed as a trait variate: Flowering duration=Flowering end day−Flowering time (50%). The site mean flowering time varied from 24 to 30 days which is shorter than average and reflected conditions that prevailed due seed filling. Statistically the variation for flowering duration of the transgenic lines was significantly within the range expressed by the cultivars across all experiments.

Plants at harvest based on plants per square meter varied significantly between lines for all eight sites. The variation for plant number at harvest time for the transgenic lines was significantly (P<0.05) within the range expressed by the cultivars across all plantings and locations. The number of plants at emergence was significantly correlated to number of plants recorded at harvest. Some of the calculated survival percent exceeded 100%, which reflected slow seedling emergence in two cultivars (ATR Wahoo and AV Jade): not all seedlings had emerged at the time plant emergence counts were recorded.

Plant height at physiological maturity was measured from base to growing tip in the center of the plot. The center of the plot was used to avoid confounding effects likely associated with inter-plot spatial area (edge effects). This trait was recorded for each plot across all trials and analyzed as a trait variate. Plant height at maturity (cm), varied significantly (P<0.05) between lines for all sites. The site mean plant height varied from 63 cm to 105 cm, and indicated environmental differences across experimental sites for this trait. The variation for height at maturity for the transgenic lines was significantly (P<0.05) within the range expressed by the cultivars across all experiments.

Seed shattering (sometimes referred to as pod shattering) at maturity was analyzed using seed shattering count per ⅛th of a square meters recorded over a two-week period. This was undertaken by placing two trays between sown rows and beneath the canopy for each plot in all locations, and analyzed as a trait variate. A seed shattering score (based on a scale of 1 [nil] to 9 [high: +40]) was also recorded at one site based on the number of seed observed on the ground just prior to harvest and analyzed as a trait variate. Seed shattering based on number of seeds on the ground at harvest varied significantly (P<0.05) between lines for four of eight sites. The site mean seed shattering number varied from 3 to 15 (per ⅛th of a square meter), and indicated low levels of shattering across all sites. The seed shattering score at one of the sites also varied significantly between lines, and was closely correlated with the across-site mean seed shatter count. This indicates that shattering recorded as a score was a good predictor of seed shattering. Statistically, the variation for seed shattering based on seed counts and score for the transgenic lines was significantly within the range expressed by the cultivars across all experiments.

Lodging resistance was recorded as a 1 (resistant) to 9 (susceptible), scored on the basis of angle of plant lean from the base of the plant at maturity. There was no statistically significant variation for plant lodging. The lack of variation for this trait is likely to be associated with below average rainfall at late pod fill stage.

Blackleg leaf severity symptoms representative of *Leptosphaeria maculans* and *Leptosphaeria biglobosa* were recorded as a 1 (low: <5%) to 9 (high: >40%) score for one replicate across five sites. Not all plots were scored, due lack of observable variation. Symptoms associated with cankering and stem breakage were not observed. Blackleg disease leaf symptoms observed were at very low levels at all eight sites. One site was sown using bare seed (seed untreated with fungicide). There were no relative differences in plant emergence amongst lines tested between this site and other sites treated with seed fungicide. Leaf symptoms are not always predictive of the degree of stem cankering caused by *L. maculans* (the main cause of yield loss and basis for resistance rating in Australia, see Sosnowski et al., 33 Australian Plant Pathol. 401 (2004)). Several studies have evaluated blackleg resistance on the basis of pathogen infection on cotyledons, leaves, stem (canker) and plant survival under field conditions. Given the lack of cankering and stem breakage the canola lines can be considered resistant to the present disease pressure for the purposes described herein.

Plant harvest count was estimated by counting plants in two, one-square-meter quadrants within each plot in all eight sites. The average of both quadrants was then used to estimate the number of plants per square meter, and analyzed as a trait a variate. Plant survival percent (%) was calculated by expressing site means for plant count as a % of site means for plant emergence count: Plant survival %=(Plant harvest count×100)/Plant Emergence count.

Grain was harvested using a plot harvester when experimental seed was physiologically mature. Harvest direction was kept consistent (i.e., front to back range for each row) for each trial to avoid harvest direction errors. Dry grain weight for each plot was determined and converted to units of t/ha based on plot area, and analyzed as a trait variate.

The grain moisture at harvest and in a lab sample was recorded and analyzed as a trait variate. A hand held moisture meter was used to analyze bulk samples directly at point of harvest in the experimental field. Percent moisture was also determined using an oven drying method based on Australian Oilseed Federation (AOF) method 4-1.5. This method involved oven-drying a 5 g sample in open tins at 130° C. for 1 hr. The samples were cooled in a desiccator for 40 min and weighed and percent moisture determined as a percent loss of mass. Grain moisture at harvest (as percent) varied significantly between line treatments for all eight sites. The site mean grain moisture at harvest varied from 9% to 12% which indicated that seeds were harvested at a similar grain stage. Statistically, the variation for grain moisture at harvest for the transgenic lines was significantly within the range expressed by the cultivars across all experiments. The grain moisture percent at harvest was also correlated with flowering time, such that seed of later-flowering lines (i.e., ATR Wahoo and Monola515TT) had significantly higher grain moisture % at harvest time across all sites. Laboratory seed moistures varied significantly between lines across all sites. The differences between lines and across sites were very low, however, and averaged ~7%. This indicates no confounding effects of seed storage. The variation for seed moisture in the laboratory for the transgenic line was significantly (P<0.05) within the range expressed by non-transgenic lines.

The seed oil content (%) was analyzed using Spinlock NMR spectrometry on seed adjusted to 6% moisture. Briefly, samples of 5 g to 10 g of seed were weighed into an NMR tube and analyzed by the NMR spectrometer. Seed oil results were determined by a software calibration created originally using twenty reference samples of known percent oil content, as determined by gravimetric oil extraction. The seed oil content varied significantly (P<0.05) between lines across all eight experiment sites. The site mean seed oil percent varied from 37.0% to 41.5%, which was generally below the typical average for the sown environments and was a likely result of below-average rainfall and higher-than-average temperatures experienced during the seed filling period. The relative line differences were very consistent across sites. The variation for seed oil content for the transgenic lines was slightly lower compared with the non-transgenic lines across all sites: on average by about 2%, which may offer a target for genetic improvement. The lower oil content may not be linked genetically to the transgenic event, but may be the result of transforming a lower oil content cultivar, i.e., AV Jade.

A summary of the characterization of the agronomic traits of event NS-B50027-4 compared with those of non-transgenic cultivars gathered during experimental cultivations is shown in Table 2 (analysis REML; F pr<0.001 Sig for all traits):

TABLE 2

Grain yield (t/ha) and agronomic measurement data for canola non-transgenic cultivars and experimental transgenic test lines across eight environments in 2015

| Line name | Emergence Plant per m² | Harvest Plant Count Plant per m² | Emergence Score (1-9) | Plant Vigor Score (1-9) | Start of Flowering Day | End of Flowering Day |
|---|---|---|---|---|---|---|
| ATR Bonito | 18.2 | 16.0 | 7.3 | 6.8 | 103.8 | 131.2 |
| ATR Gem | 17.9 | 16.6 | 7.1 | 6.7 | 105.3 | 133.6 |
| ATR Stingray | 17.6 | 17.3 | 7.1 | 5.9 | 100.9 | 129.7 |
| ATR Wahoo | 11.2 | 11.8 | 5.9 | 6.1 | 108.2 | 136.0 |
| AV Garnet | 18.6 | 16.3 | 7.4 | 7.2 | 104.4 | 132.8 |
| AV Jade | 7.8 | 12.5 | 5.0 | 4.8 | 106.7 | 134.8 |
| AV Zircon | 19.0 | 15.7 | 7.3 | 7.0 | 104.4 | 132.0 |
| Monola 515TT | 20.3 | 18.5 | 7.5 | 5.8 | 108.6 | 136.1 |
| NS-B50027-4 | 18.1 | 15.7 | 7.1 | 5.9 | 107.8 | 135.0 |
| B0050-027-18-36-13 | 22.5 | 20.3 | 7.2 | 5.9 | 106.6 | 134.4 |
| B-050-27-18-105-13 | 22.6 | 19.8 | 7.6 | 5.4 | 108.5 | 135.8 |
| Min Cultivar Value | 7.8 | 11.8 | 5.0 | 4.8 | 100.9 | 129.7 |
| NS-B50027-4 | 18.1 | 15.7 | 7.1 | 5.9 | 107.8 | 135.0 |
| Max Cultivar Value | 20.3 | 18.5 | 7.5 | 7.2 | 108.6 | 136.1 |
| Mean | 17.6 | 16.4 | 7.0 | 6.2 | 104.7 | 133.2 |
| VAR | 0.67 | 0.98 | 0.02 | 0.01 | 0.04 | 0.07 |
| LSD | 1.62 | 1.95 | 0.28 | 0.21 | 0.41 | 0.54 |
| CV % | 4.6 | 6.0 | 2.0 | 1.7 | 0.2 | 0.2 |

| Line name | Flowering Duration Days | Plant Height at Maturity cm | Shattered Seed No. | Grain Yield t/ha | Grain moisture at harvest % |
|---|---|---|---|---|---|
| ATR Bonito | 27.5 | 90.0 | 13.0 | 1.35 | 10.6 |
| ATR Gem | 28.2 | 91.0 | 10.9 | 1.21 | 13.0 |
| ATR Stingray | 28.8 | 82.7 | 14.4 | 1.34 | 8.2 |
| ATR Wahoo | 27.3 | 92.3 | 10.7 | 1.12 | 18.7 |
| AV Garnet | 28.6 | 102.1 | 15.0 | 1.31 | 10.2 |
| AV Jade | 28.3 | 89.9 | 9.8 | 0.96 | 9.9 |
| AV Zircon | 27.6 | 98.7 | 22.5 | 1.31 | 9.5 |
| Monola 515TT | 27.3 | 87.9 | 12.3 | 1.24 | 12.4 |
| NS-B50027-4 | 27.2 | 88.2 | 10.5 | 1.17 | 11.0 |
| B0050-027-18-36-13 | 27.9 | 76.4 | 10.3 | 0.95 | 10.8 |
| B-050-27-18-105-13 | 27.3 | 70.6 | 8.9 | 0.92 | 11.1 |
| Min Cultivar Value | 27.3 | 82.7 | 9.8 | 0.96 | 8.2 |
| NS-B50027-4 | 27.2 | 88.2 | 10.5 | 1.17 | 11.0 |
| Max Cultivar Value | 28.8 | 102.1 | 22.5 | 1.35 | 18.7 |
| Mean | 28.5 | 90.0 | 12.0 | 1.14 | 11.0 |
| VAR | 0.13 | 1.35 | 2.74 | 0.00 | 0.15 |
| LSD | 0.71 | 2.30 | 3.30 | 0.11 | 0.78 |
| CV % | 1.3 | 1.3 | 13.8 | 5.0 | 3.6 |

Fatty Acids were determined using solvent extraction, followed by simultaneous saponification and methylation, and analysis by GC-FID. Briefly, this involved crushing the seed samples and extracting the oil into solvent from a crushed-seed subsample. The solvent was evaporated off under nitrogen, and an oil subsample was diluted in a new solvent. An aliquot was reacted with Meth Prep II (a saponification/methylation reagent). Samples were heated at 40° C. to speed the reaction, and then injected on GC-FID using a BPX-70 column for fatty acid determination. Fatty acids were calculated as percent composition of the oil where the area of each fatty acid peak was determined as a percentage of the sum of all the fatty acid peaks in the chromatogram. These estimates were analyzed individually as a trait variate. The percent of specific fatty was estimated for: palmitic acid; stearic acid; oleic and cis-vaccenic acids; linoleic acid; alpha linolenic acid (ALA); arachidic acid (also known as eicosanoic acid) and stearidonic acid (SDA); paullinic, gondoic, and gadoleic acids; erucic acid, and eicosatetraenoic acid (ETA); eicosapentaenoic acid (EPA); docosapentaenoic acid (DPA); and docosahexaenoic acid (DHA).

Table 3 presents an across-site analysis of seed fatty acid content (all values percent; analysis REML; F pr<0.001 Sig for all traits):

TABLE 3

Across-site analysis of seed analysis

| | Lab Seed Moisture | Seed Oil | Palmitic | Stearic | Oliec & Cis-vaccenic | Linoleic |
|---|---|---|---|---|---|---|
| ATR Bonito | 6.7 | 41.9 | 3.9 | 1.7 | 60.5 | 20.9 |
| ATR GEM | 6.8 | 41.5 | 3.7 | 1.7 | 66.3 | 14.9 |
| ATR Stingray | 6.6 | 40.8 | 4.3 | 1.8 | 60.6 | 20.5 |
| ATR Wahoo | 6.8 | 41.7 | 3.7 | 1.6 | 60.7 | 20.4 |
| AV Garnet | 7.1 | 40.4 | 3.6 | 1.7 | 69.6 | 11.8 |
| AV Jade | 6.7 | 41.0 | 4.0 | 2.2 | 61.0 | 18.7 |
| AV Zircon | 6.8 | 41.0 | 3.8 | 1.6 | 69.3 | 11.8 |
| Monola 515TT | 6.9 | 40.9 | 3.6 | 2.1 | 73.3 | 12.2 |
| NS-B50027-4 | 6.9 | 37.0 | 4.1 | 2.1 | 45.9 | 8.2 |
| B0050-027-18-36-13 | 7.1 | 35.5 | 4.2 | 2.4 | 41.8 | 7.9 |
| B-050-27-18-105-13 | 7.2 | 35.3 | 4.1 | 2.4 | 42.0 | 7.7 |
| Min Cultivar Value | 6.6 | 40.4 | 3.6 | 1.6 | 60.5 | 11.8 |
| NS-B50027-4 | 6.9 | 37.0 | 4.1 | 2.1 | 45.9 | 8.2 |
| Max Cultivar Value | 7.1 | 41.9 | 4.3 | 2.2 | 73.3 | 20.9 |
| Mean | 6.8 | 39.6 | 3.9 | 2 | 55 | 14.8 |
| VAR | 0.002 | 0.05 | 0.0005 | 0.0003 | 0.1912 | 0.0385 |
| LSD | 0.09 | 0.44 | 0.04 | 0.03 | 0.87 | 0.39 |
| CV% | 0.7 | 0.6 | 0.5 | 0.9 | 0.8 | 1.3 |

| | ALA, Arachidic, & SDA | Paullinic, Gondoic, & Gadoleic | EPA | DPA | DHA | Sum of EPA, DPA, and DHA |
|---|---|---|---|---|---|---|
| ATR Bonito | 10.1 | 1.1 | 0.0 | 0.0 | 0.0 | 0.0 |
| ATR GEM | 10.2 | 1.2 | 0.0 | 0.0 | 0.0 | 0.1 |
| ATR Stingray | 9.7 | 1.0 | 0.0 | 0.0 | 0.1 | 0.1 |
| ATR Wahoo | 10.4 | 1.2 | 0.0 | 0.0 | 0.1 | 0.1 |
| AV Garnet | 9.7 | 1.5 | 0.0 | 0.0 | 0.1 | 0.1 |
| AV Jade | 11.2 | 1.0 | 0.0 | 0.0 | 0.1 | 0.2 |
| AV Zircon | 10.4 | 1.3 | 0.0 | 0.0 | 0.0 | 0.0 |
| Monola 515TT | 5.2 | 1.4 | 0.0 | 0.0 | 0.1 | 0.2 |
| NS-B50027-4 | 20.7 | 3.4 | 0.4 | 1.0 | 8.6 | 9.9 |
| B0050-027-18-36-13 | 22.2 | 3.8 | 0.6 | 1.2 | 10.5 | 12.2 |
| B-050-27-18-105-13 | 22.1 | 3.9 | 0.5 | 1.2 | 10.3 | 12.0 |
| Min Cultivar Value | 5.2 | 1.0 | 0.0 | 0.0 | 0.0 | 0.0 |
| NS-B50027-4 | 20.7 | 3.4 | 0.4 | 1.0 | 8.6 | 9.9 |
| Max Cultivar Value | 11.2 | 1.5 | 0.0 | 0.0 | 0.1 | 0.2 |
| Mean | 15 | 2.3 | 0.1 | 0.6 | 3.1 | 3.8 |
| VAR | 0.0475 | 0.0032 | 0.0001 | 0.0005 | 0.0248 | 0.0345 |
| LSD | 0.43 | 0.11 | 0.02 | 0.05 | 0.31 | 0.37 |
| CV % | 1.5 | 2.5 | 6.3 | 4.1 | 5.1 | 4.9 |

The percent of fatty acid in the seed present as stearic acid, as analyzed by GC-FID varied significantly between lines across all eight sites. The site-mean percent stearic acid showed very little variation and ranged from 1.6% to 2.4%. Statistically, the variation for percent stearic acid for the transgenic line was significantly within the range expressed by the non-transgenic lines across all sites.

The percent of fatty acid in the seed as oleic and cis-vaccenic acid, as analyzed by GC-FID, varied significantly between lines across all eight sites. The site-mean percent oleic and cis-vaccenic acid varied from 60% to 73%. The variation for percent oleic and cis-vaccenic acid for the transgenic line was significantly ($P<0.05$) lower than the range expressed by the non-transgenic lines across all sites. This result is associated with the transgenic insert, and does not affect commercial agronomy or grain production. Additionally, the specialty high oleic oil cultivar, Monola515 TT, produced significantly higher oleic and cis-vaccenic acid compared to other cultivars, due to single nucleotide polymorphisms (SNPs) within the Fad gene.

The percent of fatty acid in the seed present as linoleic acid, as analyzed using GC-FID, varied significantly among all lines across all eight sites. The mean percent linoleic acid per site ranged from 12% to 21%. The variation for percent linoleic acid for the transgenic sib lines derived from one T2 event (plant NS-B50027-4) was significantly ($P<0.05$) lower than the range expressed by the cultivars across all sites and sibs derived from other event sibs. The significant difference in linoleic acid % is likely associated with expression of transgenes. A reduction in the % linoleic acid is likely associated with the transgenic insert, but does not affect agronomy or grain production on the commercial scale.

The percent of fatty acid present as ALA, arachidic, and SDA varied significantly among all lines across all eight sites. The site mean for percent ALA, arachidic, and SDA ranged from between 5% to 11%. The variation for the % ALA, arachidic, and SDA for the transgenic lines was significantly ($P<0.05$) higher than that expressed by the non-transgenic cultivars across all experiments. The significant differences seen for this trait at some sites was associated with expression of transgenes. This result is associated with the transgenic insert, and does not affect commercial agronomy or grain production. The specialty high oleic oil cultivar (Monola515 TT) produced significantly (P<0.05) lower % ALA compared to other cultivars, due to SNPs within the Fad genes.

The percent of fatty acid present as paullinic, gondoic, and gadoleic acids varied significantly between lines across all eight sites. The site mean for percent paullinic, gondoic, and gadoleic acid ranged from 1.0% to 1.5%. The variation for the percent paullinic, gondoic, and gadoleic acids for the transgenic lines was significantly (P<0.05) higher than that expressed by the non-transgenic cultivars across all experiments. This result is associated with the transgenic insert and does not affect commercial agronomy or grain production.

The percent of fatty acid present as erucic acid and ETA was recorded at five sites, and was generally close to 0%. Results associated with the transgenic insert do not commercially affect agronomy or grain production.

Seed LC-ω3 polyunsaturated fatty acid (LC-PUFA), specifically EPA, DPA, and DHA, was calculated as a percent for each plot sample and analyzed as a trait variate in which LC-PUFA=EPA %+DPA %+DHA %. Predicted DHA, as units of Kg/ha, was calculated for each plot and analyzed as a trait variate: DHA kg/ha=(Oil %×0.01)×(DHA %×0.01)× Grain yield (t/ha)×1000. Predicted LC-PUFA as units of Kg/ha was calculated for each plot as and analyzed as a trait variate: DHA kg/ha=(Oil %×0.01)×(LC-PUFA %×0.01)× Grain yield (t/ha)×1000.

The percent of fatty acid as EPA varied significantly (P<0.05) between lines across all eight sites. The variation for the percent for the transgenic line was significantly (P<0.05) higher than that expressed by the non-transgenic cultivars. This result, associated with the transgenic insert, does not affect agronomy or seed production, but, indeed, may make the seed more valuable.

The percent of fatty acid as DPA varied significantly between lines across all sites. The variation for the percent for the transgenic lines was significantly (P<0.05) higher than that expressed by the non-transgenic cultivars across all sites. This result is associated with the transgenic insert and will not affect agronomy or grain production commercially.

The percent of fatty acid as DHA varied significantly (P<0.05) between lines across all eight sites. The variation for the percent for the transgenic lines was significantly (P<0.05) higher than that expressed by the non-transgenic cultivars in all locations. This result is associated with the transgenic insert and does not affect commercial agronomy or grain production. Variance between transgenic sib lines was used as a basis for selection.

DHA percent across sites and comparing elite event NS-B50027-4 with non-transgenic cultivars (as determined by GC-FID) is shown in Table 4 (analysis REML; F pr<0.001 Sig for all locations):

TABLE 4

Site by cultivar/elite event mean seed % DHA (C22:6n3)

| Line name | Site: A | B | C | D | E | F | G | H | Across-site mean |
|---|---|---|---|---|---|---|---|---|---|
| ATR Bonito | 0.0 | 0.0 | 0.0 | 0.1 | 0.1 | 0.0 | 0.1 | 0.0 | 0 |
| ATR Gem | 0.0 | 0.0 | 0.0 | 0.1 | 0.1 | 0.1 | 0.1 | 0.0 | 0.1 |
| ATR Stingray | 0.0 | 0.1 | 0.2 | 0.3 | 0.0 | 0.1 | 0.1 | 0.0 | 0.1 |
| ATR Wahoo | 0.1 | 0.2 | 0.1 | 0.2 | 0.0 | 0.2 | 0.1 | 0.0 | 0.1 |
| AV Garnet | 0.0 | 0.0 | 0.0 | 0.2 | 0.1 | 0.2 | 0.2 | 0.0 | 0.1 |
| AV Jade | 0.0 | 0.3 | 0.5 | 0.0 | 0.2 | 0.1 | 0.3 | 0.0 | 0.2 |
| AV Zircon | 0.0 | 0.1 | 0.1 | 0.1 | 0.2 | 0.1 | 0.1 | 0.0 | 0.1 |
| Monola 515TT | 0.1 | 0.1 | 0.3 | 0.2 | 0.1 | 0.1 | 0.2 | 0.0 | 0.1 |
| NS-B50027-4 | 8.1 | 9.8 | 7.8 | 7.5 | 8.5 | 8.4 | 8.8 | 10.2 | 8.6 |
| B0050-027-18-36-13 | 10.0 | 12.2 | 9.5 | 9.7 | 10.1 | 10.4 | 10.8 | 13.3 | 10.8 |
| B-050-27-18-105-13 | 10.5 | 11.3 | 9.0 | 9.6 | 10.2 | 9.7 | 10.9 | 12.5 | 10.5 |
| Min Cultivar Value | 0.0 | 0.0 | 0.0 | 0.0 | 0.0 | 0.0 | 0.1 | 0.0 | 0 |
| NS-B50027-4 | 8.1 | 9.8 | 7.8 | 7.5 | 8.5 | 8.4 | 8.8 | 10.2 | 8.6 |
| Max Cultivar Value | 0.1 | 0.3 | 0.5 | 0.3 | 0.2 | 0.2 | 0.3 | 0.0 | 0.2 |
| Mean | 3.5 | 3.6 | 3 | 2.49 | 3.7 | 3.56 | 3.88 | 4.1 | |
| VAR | 0.15 | 0.07 | 0.079 | 0.29 | 0.14 | 0.14 | 0.11 | 0.18 | |
| SE | 0.39 | 0.27 | 0.281 | 0.53 | 0.37 | 0.37 | 0.33 | 0.42 | |
| LSD | 0.78 | 0.54 | 0.6 | 1.1 | 0.75 | 0.73 | 0.65 | 0.84 | |
| CV % | 11 | 7.5 | 9.4 | 21.5 | 10 | 10.6 | 8.4 | 10.4 | |

Predicted DHA expressed as Kg/ha, calculated on the basis of fatty acid profile, seed oil percent and grain yield, varied significantly (P<0.05) between lines across all sites. The variation for the % for the transgenic lines was significantly (P<0.05) higher than that expressed by the non-transgenic lines across all locations. This result is associated with the transgenic insert and does not affect commercial agronomy or grain production. Variance between transgenic sib lines was used as a basis for selection. There was high stability of DHA, in terms of units of production per area (Kg/ha), due to low across-site variation for seed oil and percent DHA produced in the seed.

Predicted yield of DHA (Kg/ha) across sites and comparing elite event NS-B50027-4 with non-transgenic cultivars is shown in Table 5 (analysis REML, F pr<0.001 Sig for all locations):

TABLE 5

Site by line mean seed predicted DHA (Kg/ha)

| Line name | Site: A | B | C | D | E | F | G | H | Across-site mean |
|---|---|---|---|---|---|---|---|---|---|
| ATR Bonito | 0 | 1 | 0 | 1 | 0 | 0 | 1 | 0 | 0 |
| ATR Gem | 0 | 0 | 0 | 0 | 2 | 2 | 2 | 1 | 1 |
| ATR Stingray | 0 | 0 | 0 | 1 | 0 | 0 | 0 | 0 | 0 |
| ATR Wahoo | 1 | 0 | 1 | 0 | 0 | 1 | 1 | 0 | 0 |
| AV Garnet | 0 | 1 | 2 | 1 | 1 | 4 | 1 | 2 | 1 |
| AV Jade | 0 | 0 | 1 | 0 | 1 | 0 | 0 | 0 | 0 |
| AV Zircon | 0 | 0 | 0 | 2 | 0 | 4 | 1 | 0 | 1 |
| Monola 515TT | 0 | 0 | 2 | 0 | 2 | 0 | 0 | 0 | 0 |
| NS-B50027-4 | 30 | 28 | 39 | 36 | 50 | 49 | 24 | 41 | 37 |
| B0050-027-18-36-13 | 25 | 27 | 41 | 41 | 52 | 53 | 24 | 36 | 37 |
| B-050-27-18-105-13 | 24 | 25 | 34 | 50 | 46 | 40 | 26 | 33 | 35 |
| Min Cultivar Value | 0.0 | 0.0 | 0.0 | 0.0 | 0.0 | 0.0 | 0.0 | 0.0 | 0.0 |
| NS-B50027-4 | 30.0 | 28.0 | 39.0 | 36.0 | 50.0 | 49.0 | 24.0 | 41.0 | 37.0 |
| Max Cultivar Value | 1.0 | 1.0 | 2.0 | 2.0 | 2.0 | 4.0 | 2.0 | 2.0 | 1.0 |
| Mean | 8 | 8 | 12 | 12 | 16 | 17 | 8 | 12 | |
| VAR | 3.93 | 3.08 | 14.60 | 38.66 | 10.77 | 24.55 | 7.60 | 6.94 | |
| SE | 1.98 | 1.75 | 3.81 | 6.20 | 3.28 | 4.79 | 2.75 | 2.63 | |
| LSD | 4.0 | 3.5 | 7.6 | 12.4 | 6.6 | 9.6 | 5.5 | 5.3 | |
| CV % | 23.6 | 22.5 | 33.1 | 53.4 | 20.3 | 29.8 | 34.2 | 22.7 | |

Regarding seed LC-PUFA omega 3—percent EPA, DPA, and DHA (measured by HPLC)—the percent LC-PUFA varied significantly (P<0.05) between line treatments across all eight sites. The variation for the % for the transgenic lines was significantly (P<0.05) higher than that expressed by the cultivars across all experiments. This result is associated with the transgenic insert and does not affect agronomy or commercial grain production. Variance between transgenic sib lines was used as a basis for selection. Trace levels of LC-PUFA observed in non-transgenic lines was likely to be associated with pollen flow, seed movement, or GC-FID error.

Table 6 shows the percent values as determined by GC-FID (analysis REML; F pr<0.001 Sig for all locations):

TABLE 6

Site by cultivar or transgenic line: mean seed LC-PUFA (% sum of EPA + DPA + DHA)

| Line name | Site: A | B | C | D | E | F | G | H | Across-site mean |
|---|---|---|---|---|---|---|---|---|---|
| ATR Bonito | 0.0 | 0.0 | 0.0 | 0.1 | 0.1 | 0.0 | 0.2 | 0.2 | 0.1 |
| ATR Gem | 0.0 | 0.0 | 0.0 | 0.1 | 0.2 | 0.1 | 0.1 | 0.1 | 0.1 |
| ATR Stingray | 0.0 | 0.1 | 0.2 | 0.3 | 0.0 | 0.1 | 0.1 | 0.5 | 0.2 |
| ATR Wahoo | 0.1 | 0.2 | 0.1 | 0.2 | 0.0 | 0.2 | 0.1 | 0.2 | 0.1 |
| AV Garnet | 0.0 | 0.0 | 0.0 | 0.1 | 0.1 | 0.2 | 0.2 | 0.0 | 0.1 |
| AV Jade | 0.0 | 0.4 | 0.5 | 0.0 | 0.2 | 0.1 | 0.3 | 0.0 | 0.2 |
| AV Zircon | 0.0 | 0.2 | 0.1 | 0.1 | 0.2 | 0.1 | 0.1 | 0.3 | 0.1 |
| Monola 515TT | 0.1 | 0.1 | 0.3 | 0.2 | 0.2 | 0.1 | 0.2 | 0.0 | 0.2 |

TABLE 6-continued

Site by cultivar or transgenic line: mean seed LC-PUFA
(% sum of EPA + DPA + DHA)

| Line name | A | B | C | D | E | F | G | H | Across-site mean |
|---|---|---|---|---|---|---|---|---|---|
| NS-B50027-4 | 9.5 | 11.4 | 9.1 | 8.9 | 9.8 | 9.8 | 10.3 | 11.8 | 10.1 |
| B0050-027-18-36-13 | 11.7 | 14.2 | 11.0 | 11.4 | 11.8 | 12.2 | 12.7 | 15.3 | 12.5 |
| B-050-27-18-105-13 | 12.2 | 13.2 | 10.5 | 11.3 | 11.9 | 11.3 | 12.7 | 14.5 | 12.2 |
| Min Cultivar Value | 0.0 | 0.0 | 0.0 | 0.0 | 0.0 | 0.0 | 0.1 | 0.0 | 0.0 |
| NS-B50027-4 | 9.5 | 11.4 | 9.1 | 8.9 | 9.8 | 9.8 | 10.3 | 11.8 | 10.1 |
| Max Cultivar Value | 0.1 | 0.4 | 0.5 | 0.3 | 0.2 | 0.2 | 0.3 | 0.5 | 0.2 |
| Mean | 4.3 | 4.4 | 3.6 | 3.05 | 4.5 | 4.34 | 4.75 | 4.9 | |
| VAR | 0.23 | 0.11 | 0.112 | 0.33 | 0.19 | 0.2 | 0.14 | 0.23 | |
| SE | 0.48 | 0.33 | 0.334 | 0.58 | 0.44 | 0.43 | 0.38 | 0.48 | |
| LSD | 0.95 | 0.66 | 0.7 | 1.2 | 0.87 | 0.87 | 0.76 | 0.96 | |
| CV % | 11 | 7.6 | 9.3 | 18.9 | 9.7 | 10.3 | 8 | 9.8 | |

Figure 2:
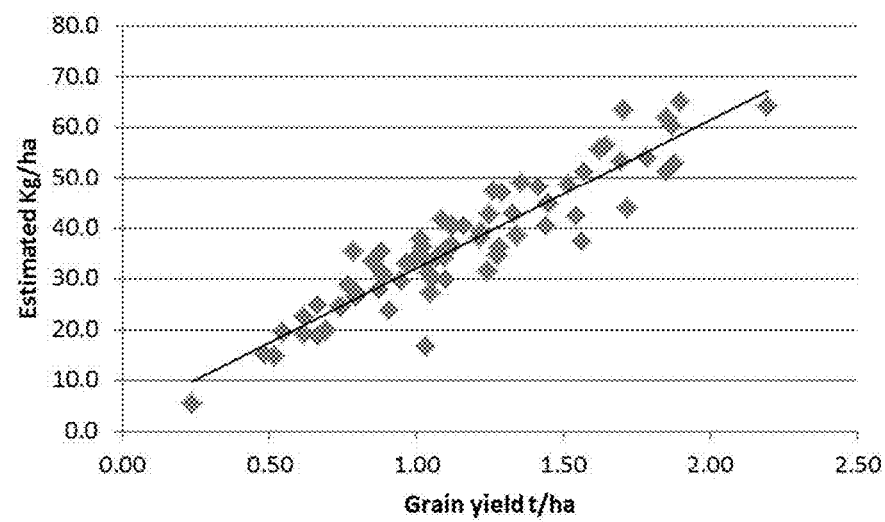
FIG. 2 is a graph of grain yield plotted against predicted DHA, in kg/ha, across eight cultivation sites. ♦ is DHA Kg/ha; - - is linear DHA Kg/ha; y=29.296x+2.8315; $R^2$=0.8567.
Figure 3:
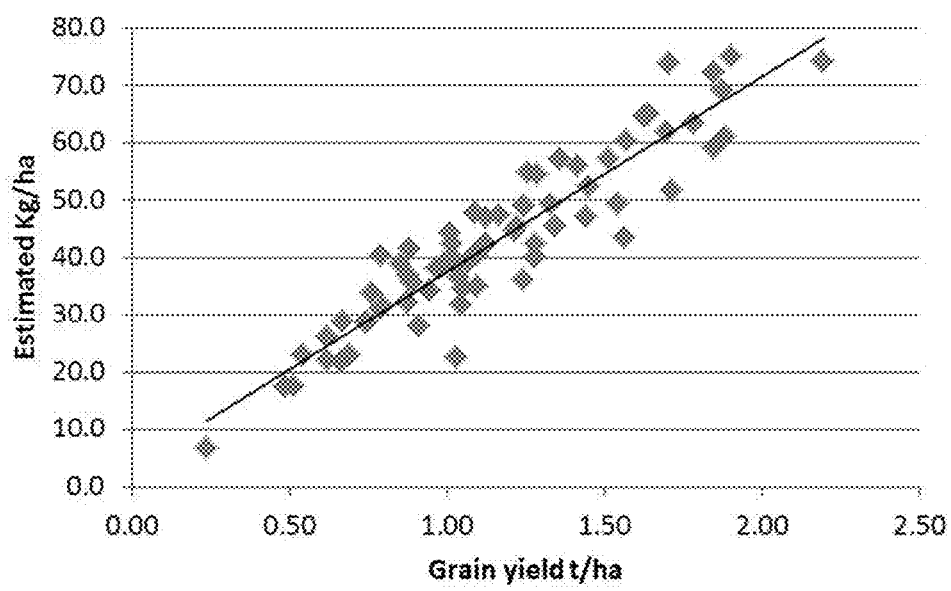
FIG. 3 depicts grain yield graphed against predicted LC-PUFA (EPA, DPA, and DHA) in kg/ha, across eight sites. ♦ is LC-PUFA Kg/ha; - - is linear LC-PUFA Kg/ha; y=34.043x+3.4049; $R^2$=0.8636.

Predicted LC-PUFA expressed as Kg/ha calculated on the basis of fatty acid profile, seed oil % and grain yield varied significantly (P<0.05) between treatment lines across all sites. The variation for the % for the transgenic lines was significantly (P<0.05) higher than that expressed by the cultivars across all experiments. This result is associated with the transgenic insert and does not commercially affect agronomy or grain production. Variance between transgenic sib lines was used as a basis for selection. Trace levels in cultivar seed is likely to be associated with pollen flow, seed movement, or HPLC error. There is high stability of LC-PUFA in terms of units of production per area (Kg/ha) due to low across-site variation for seed oil and percent DHA produced in the seed. See also FIG. 2 and FIG. 3.

Table 7 shows the predicted Kg/ha LC-PUFU (F pr<0.001 for all sites):

TABLE 7

Site by cultiyar (line) mean seed predicted LC-PUFA (Kg/ha)

| Line name | A | B | C | D | E | F | G | H | Across-site mean |
|---|---|---|---|---|---|---|---|---|---|
| ATR Bonito | 0 | 1 | 0 | 1 | 0 | 0 | 1 | 0 | 0 |
| ATR Gem | 1 | 0 | 0 | 0 | 2 | 3 | 3 | 0 | 1 |
| ATR Stingray | 1 | 0 | 0 | 1 | 0 | 0 | 0 | 0 | 0 |
| ATR Wahoo | 0 | 0 | 2 | 0 | 0 | 1 | 1 | 0 | 1 |
| AV Garnet | 0 | 1 | 2 | 1 | 1 | 4 | 1 | 0 | 1 |
| AV Jade | 0 | 1 | 1 | 0 | 1 | 0 | 0 | 0 | 0 |
| AV Zircon | 0 | 0 | 0 | 2 | 0 | 4 | 2 | 0 | 1 |
| Monola 515TT | 0 | 0 | 2 | 0 | 2 | 0 | 0 | 0 | 1 |
| NS-B50027-4 | 35 | 33 | 46 | 43 | 58 | 58 | 28 | 46 | 43 |
| B0050-027-18-36-13 | 29 | 32 | 48 | 48 | 60 | 61 | 28 | 41 | 43 |
| B-050-27-18-105-13 | 28 | 29 | 40 | 58 | 53 | 46 | 30 | 40 | 41 |
| Mean | 10 | 10 | 14 | 14 | 20 | 20 | 10 | 14 | |
| VAR | 5.50 | 4.34 | 21.71 | 54.48 | 15.98 | 34.93 | 11.14 | 58.10 | |
| SE | 2.34 | 2.08 | 4.65 | 7.36 | 3.99 | 5.71 | 3.33 | 4.04 | |
| LSD | 4.7 | 4.2 | 9.3 | 14.7 | 8.0 | 11.4 | 6.7 | 8.1 | |
| CV % | 22.6 | 21.9 | 33.1 | 51.9 | 20.1 | 28.9 | 33.5 | 54.8 | |

Seed oil content, determined using NMR, was also tabulated for each of the cultivation sites, and is presented in Table 8 (units are percent; analysis REML; F pr<0.001 Sig for all sites):

TABLE 8

Site by cultivate seed oil mean oil %

| Line: | A | B | C | D | E | F | G | H | Across-site mean |
|---|---|---|---|---|---|---|---|---|---|
| ATR Bonito | 43.0 | 40.6 | 43.6 | 43.4 | 42.6 | 41.8 | 39.1 | 39.6 | 41.7 |
| ATR Gem | 43.7 | 40.7 | 43.9 | 42.7 | 42.3 | 40.5 | 37.8 | 39.5 | 41.3 |
| ATR Stingray | 41.4 | 39.7 | 42.6 | 42.8 | 41.1 | 39.1 | 38.9 | 39.9 | 40.6 |
| ATR Wahoo | 43.1 | 41.0 | 43.3 | 43.4 | 42.5 | 40.1 | 39.0 | 39.9 | 41.4 |
| AV Garnet | 43.9 | 39.9 | 43.4 | 41.8 | 41.5 | 39.1 | 36.5 | 36.4 | 40.2 |
| AV Jade | 41.7 | 40.2 | 42.6 | 42.2 | 42.5 | 38.6 | 37.5 | 39.4 | 40.6 |
| AV Zircon | 44.0 | 40.6 | 43.6 | 42.1 | 41.5 | 39.8 | 36.9 | 38.8 | 40.9 |
| Monola 515TT | 42.2 | 40.1 | 42.3 | 42.1 | 42.2 | 38.8 | 38.1 | 39.3 | 40.6 |
| NS-B50027-4 | 38.7 | 36.1 | 39.3 | 38.2 | 37.3 | 36.5 | 34.2 | 35.1 | 36.9 |
| B0050-027-18-36-13 | 36.7 | 34.3 | 37.2 | 37.9 | 36.8 | 34.3 | 33.4 | 33.2 | 35.5 |
| B-050-27-18-105-13 | 36.3 | 34.4 | 37.9 | 37.4 | 35.8 | 34.1 | 32.1 | 33.0 | 35.1 |
| Min Cultivar Value | 41.4 | 39.7 | 42.3 | 41.8 | 41.1 | 38.6 | 36.5 | 36.4 | 40.2 |
| NS-B50027-4 | 38.7 | 36.1 | 39.3 | 38.2 | 37.3 | 36.5 | 34.2 | 35.1 | 36.9 |
| Max Cultivar Value | 44.0 | 41.0 | 43.9 | 43.4 | 42.6 | 41.8 | 39.1 | 39.9 | 41.7 |
| Mean | 40.8 | 38.7 | 41.5 | 41.2 | 39.8 | 38.01 | 37 | 37.8 | |
| VAR | 0.13 | 0.09 | 0.23 | 0.13 | 0.13 | 0.19 | 0.18 | 0.1 | |
| SE | 0.36 | 0.3 | 0.477 | 0.36 | 0.36 | 0.42 | 0.43 | 0.31 | |
| LSD | 0.71 | 0.59 | 1 | 0.7 | 0.73 | 0.85 | 0.85 | 0.62 | |
| CV % | 1 | 0.8 | 1.2 | 0.9 | 0.9 | 1.1 | 1.2 | 0.8 | |

Additional analysis of the fatty acid content of NS-B50027-4 seed is presented in Table 9:

TABLE 9

Detailed fatty acid content data for NS-B50027-4 seed

| | C14:0 | C16:0 | C16:1n7c | C18:0 | C18:1n9c | C18:1n7c | C18:2n6c | GLA C18:3n6 | ALA C18:3n3 | C20:0 | SDA C18:4n3 | C20:1n9c |
|---|---|---|---|---|---|---|---|---|---|---|---|---|
| | NS-B50027-4, Generation T7, Summer 2015-2016 |
| 1* | 0.05 | 4.33 | 0.24 | 2.16 | 38.83 | 4.26 | 7.81 | 0.58 | 21.54 | 0.64 | 2.20 | 1.31 |
| 2 | 0.05 | 4.28 | 0.23 | 2.19 | 38.32 | 4.17 | 7.76 | 0.59 | 21.58 | 0.65 | 2.21 | 1.31 |
| 3 | 0.05 | 4.20 | 0.22 | 2.19 | 38.77 | 4.06 | 7.81 | 0.60 | 21.73 | 0.66 | 2.22 | 1.28 |
| 4 | 0.05 | 4.19 | 0.21 | 2.16 | 38.69 | 4.09 | 7.79 | 0.61 | 21.66 | 0.63 | 2.25 | 1.34 |
| 5 | 0.05 | 4.26 | 0.21 | 2.18 | 38.35 | 4.22 | 7.81 | 0.59 | 21.78 | 0.64 | 2.25 | 1.29 |
| | 0.05 | 4.25 | 0.22 | 2.18 | 38.69 | 4.16 | 7.80 | 0.60 | 21.66 | 0.64 | 2.23 | 1.30 |
| | NS-B50027-4, Generation T6, Winter 2015 |
| 1 | 0.0 | 4.60 | 0.21 | 2.22 | 41.95 | 3.10 | 6.35 | 0.47 | 21.06 | 0.69 | 2.27 | 1.14 |
| 2 | 0.0 | 5.00 | 0.25 | 2.01 | 36.02 | 3.50 | 6.70 | 0.66 | 21.46 | 0.66 | 3.21 | 1.10 |
| 3 | 0.09 | 4.67 | 0.24 | 2.32 | 34.45 | 3.41 | 6.33 | 0.60 | 22.53 | 0.71 | 3.35 | 1.01 |
| 4 | 0.0 | 4.57 | 0.20 | 2.01 | 34.27 | 3.08 | 6.47 | 0.59 | 23.14 | 0.65 | 3.24 | 1.08 |
| 5 | 0.0 | 5.08 | 0.30 | 2.22 | 36.51 | 3.99 | 6.55 | 0.57 | 21.59 | 0.72 | 3.41 | 1.06 |
| | 0.02 | 4.78 | 0.24 | 2.15 | 36.64 | 3.42 | 6.48 | 0.58 | 21.95 | 0.69 | 3.10 | 1.08 |
| | NS-B50027-4, Generation T5, Summer 2014-2015 |
| 1 | 0.05 | 4.51 | 0.21 | 2.05 | 39.18 | 4.10 | 8.67 | 0.66 | 21.93 | 0.60 | 1.86 | 1.38 |
| | NS-B50027-4, Generation T4, Winter 2014 |
| 1 | 0.17 | 3.93 | 0.16 | 2.14 | 44.54 | 2.65 | 7.02 | 0.45 | 19.4 | 0.64 | 2.21 | 1.26 |

| | C21:0 | DGLA C20:3n6 | ETE C20:3n3 | C22:0 | ETA C20:4n3 | C22:1n9c | EPA C20:5n3 | C24:0 | DPA6 C22:5n6 | C24:1n9c | DPA3 C22:5n3 | DHA C22:6n3 |
|---|---|---|---|---|---|---|---|---|---|---|---|---|
| | NS-B50027-4, Generation T7, Summer 2015-2016 |
| 1* | 0 | 0 | 0.71 | 0.31 | 0 | 0 | 0.40 | 0.24 | | 0.10 | 0.85 | 9.69 |
| 2 | 0 | 0 | 0.70 | 0.32 | 0 | 0 | 0.39 | 0.23 | | 0.11 | 0.88 | 9.78 |
| 3 | 0 | 0 | 0.72 | 0.32 | 0 | 0 | 0.40 | 0.23 | | 0.09 | 0.89 | 9.83 |
| 4 | 0 | 0 | 0.71 | 0.33 | 0 | 0 | 0.41 | 0.23 | | 0.08 | 0.91 | 9.92 |
| 5 | 0 | 0 | 0.72 | 0.32 | 0 | 0.01 | 0.41 | 0.23 | | 0.10 | 0.89 | 9.80 |
| | 0 | 0 | 0.71 | 0.32 | 0 | 0 | 0.40 | 0.23 | | 0.10 | 0.88 | 9.80 |
| | NS-B50027-4, Generation T6, Winter 2015 |
| 1 | 0 | 0 | 0.59 | 0.34 | 0 | 0 | 0.55 | 0 | 0.09 | 0 | 0.89 | 10.22 |
| 2 | 0 | 0 | 0.47 | 0.33 | 0 | 0 | 0.68 | 0 | 0.11 | 0.10 | 1.21 | 13.34 |
| 3 | 0 | 0 | 0.60 | 0.33 | 0 | 0 | 0.80 | 0 | 0 | 0.09 | 1.13 | 14.02 |
| 4 | 0 | 0 | 0.63 | 0.38 | 0 | 0 | 0.71 | 0.14 | 0.10 | 0.10 | 1.07 | 13.99 |

TABLE 9-continued

Detailed fatty acid content data for NS-B50027-4 seed

| 5 | 0 | 0 | 0.52 | 0.37 | 0 | 0 | 0.60 | 0.11 | 0 | 0.13 | 1.06 | 12.10 |
|---|---|---|---|---|---|---|---|---|---|---|---|---|
|   | 0 | 0 | 0.56 | 0.35 | 0 | 0 | 0.67 | 0.05 | 0.06 | 0.08 | 1.07 | 12.73 |

NS-B50027-4, Generation T5, Summer 2014-2015

| 1 | 0.14 | 0 | 0.83 | 0.33 | 0 | 0 | 0.32 | 0.8 | 0.16 | 0.13 | 0.71 | 8.43 |
|---|---|---|---|---|---|---|---|---|---|---|---|---|

NS-B50027-4, Generation T4, Winter 2014

| 1 | | 0.07 | 0.46 | 0.26 | 1.09 | 0 | 0.41 | | | | 0.85 | 8.89 |
|---|---|---|---|---|---|---|---|---|---|---|---|---|

|   | Oil NMR | Sum of EPA DPA, DHA | Total Ω3 | Total Ω6 | Ω3/Ω6 | Total Saturated Fat | Total Monounsaturated Fat | Total PUFA |
|---|---|---|---|---|---|---|---|---|

NS-B50027-4, Generation T7, Summer 2015-2016

| 1* | 39.3 | 10.94 | 35.39 | 8.39 | 4.22 | 7.74 | 44.74 | 43.78 |
|---|---|---|---|---|---|---|---|---|
| 2 | 38.8 | 11.04 | 35.54 | 8.36 | 4.25 | 7.41 | 44.62 | 43.89 |
| 3 | 39.2 | 11.12 | 35.79 | 8.41 | 4.26 | 7.64 | 44.41 | 44.20 |
| 4 | 39.5 | 11.23 | 35.85 | 8.40 | 4.27 | 7.59 | 44.41 | 44.25 |
| 5 | 39.4 | 11.10 | 35.85 | 8.40 | 4.27 | 7.68 | 44.19 | 44.25 |
|   |      | 11.09 | 35.68 | 8.39 | 4.25 | 7.67 | 44.48 | 44.07 |

NS-B50027-4, Generation T6, Winter 2015

| 1 |   | 11.66 | 35.58 | 6.91 | 5.15 | 7.85 | 46.40 | 42.48 |
|---|---|---|---|---|---|---|---|---|
| 2 |   | 15.23 | 40.37 | 7.47 | 5.41 | 7.99 | 40.96 | 47.84 |
| 3 |   | 15.95 | 42.42 | 6.93 | 6.12 | 8.11 | 39.19 | 49.35 |
| 4 |   | 15.76 | 42.78 | 7.17 | 5.97 | 7.75 | 38.73 | 59.94 |
| 5 |   | 13.75 | 39.27 | 7.12 | 5.52 | 8.49 | 41.98 | 46.38 |
|   |   | 14.47 | 40.08 | 7.12 | 5.63 | 8.04 | 41.45 | 47.20 |

NS-B50027-4, Generation T5, Summer 2014-2015

| 1 |   | 9.46 | 34.09 | 9.49 | 3.59 | 7.76 | 45.00 | 43.58 |
|---|---|---|---|---|---|---|---|---|

*Sample number

The data in Table 9 confirm that in addition to LC-ω3 fatty acids, the seed of NS-B50027-4 also contains substantially more ALA than conventional canola varieties. See also Table 3. Although ALA is not a LC-PUFA, it is an ω3 fatty acid. The ratio of ω3:ω6 fatty acids in seed oil of NS-B50027-4 in Table 9 is about 3.59 to about 6.12; the ratio of ω3:ω6 fatty acids in conventional canola oil is about 0.5. See Patterson et al., J. Nutr. Metab. 2012:539426 (2012).

Table 10 presents data related to percent DHA and LC-PUFA in seed from sixteen generations of elite event NS-B50027-4 grown in experimental cultivations in Australia. An additional field trial in Australia generated bulk seed with 9.6% DHA and 10.1% LC-PUFA:

TABLE 10

Seed DHA% and LC-PUFA% from elite event NS-B50027-4 per generation

|   | Generation | Seed sample | Environment | Growing Season | Year in Field | Location | Seed DHA % | Seed LC-PUFA % |
|---|---|---|---|---|---|---|---|---|
| 1 | T1 | Single plant | Glasshouse | Controlled Environment |  | A | 5.7 | 6.0 |
| 2 | T2 | Single plant | Glasshouse | Controlled Environment |  | A | 9.5 | 10.1 |
| 3 | T3 | Single plant | Glasshouse | Controlled Environment |  | A | 12.6 | 13.1 |
| 4 | T3-x | Bulk | Isolation Tent | Winter/Spring | 2014 | B | 8.9 | 10.2 |
| 5 | T3-2x | Bulk | Open Field | Summer | 2014-15 | C | 8.4 | 9.5 |
| 6 | T3-3x | Bulk | Open Field | Winter/Spring | 2015 | D | 9.0 | 10.6 |
| 7 | T4 | Single plant | Glasshouse | Controlled Environment |  | A | 11.9 | 13.2 |
| 8 | T5 | Single plant | Glasshouse | Controlled Environment |  | A | 13.4 | 14.6 |
| 9 | T5-x | Bulk | Isolation Tent | Winter/Spring | 2015 | B | 12.7 | 14.5 |
| 10 | T5-2x | Bulk | Open Field | Summer | 2015-16 | C | 9.8 | 11.1 |
| 11 | T5-3x | Bulk | Open Field | Winter/Spring | 2016 | D | 9.6 | 10.6 |
| 12 | T6 | Single plant | Glasshouse | Controlled Environment |  | A | 12.9 | 14.4 |
| 13 | T6-x | Bulk | Isolation Tent | Summer | 2015-16 | C | 17.3 | 18.8 |
| 14 | T6-2x | Bulk | Isolation Tent | Winter/Spring | 2016 | E | 10.1 | 12.1 |
| 15 | T7 | Single plant | Glasshouse | Controlled Environment |  | A | 13.8 | 15.1 |
| 16 | T7-x | Bulk | Isolation Tent | Winter/Spring | 2016 | B | 12.5 | 14.1 |

Additionally, the ability of NS-B50027-4 to grow in Canada was tested under controlled experimental conditions at two different sites in 2016. Table 11 presents agronomic and yield data comparing NS-B50027-4 with several non-transgenic canola lines:

TABLE 11

Agronomic measurement data for non-transgenic canola cultivars and experimental transgenic test lines from two Canadian experimental cultivations in 2016

| Line name | Emergence Plant per m$^2$ | Plant height at maturity cm | Start of Flowering Day | End of Flowering Day | Flowering Duration Days | Lodging at Maturity Score (1-9) | Shattered Seed No. |
|---|---|---|---|---|---|---|---|
| ATR Bonito | 23 | 90 | 49 | 75 | 26 | 8 | 3 |
| ATR Gem | 22 | 98 | 48 | 76 | 27 | 7 | 2 |
| ATR Stingray | 21 | 88 | 48 | 75 | 27 | 9 | 6 |
| ATR Wahoo | 22 | 98 | 48 | 75 | 27 | 7 | 4 |
| AV Garnet | 27 | 110 | 48 | 76 | 28 | 6 | 7 |
| AV Jade | 27 | 109 | 48 | 76 | 29 | 8 | 3 |
| AV Zircon | 14 | 125 | 50 | 76 | 26 | 8 | 9 |
| Monola 515TT | 26 | 79 | 47 | 73 | 27 | 8 | 13 |
| DK 7444 | 21 | 112 | 47 | 72 | 25 | 7 | 4 |
| LL 130 | 18 | 123 | 47 | 73 | 26 | 8 | 4 |
| NS-B50027-4T3 | 11 | 109 | 49 | 77 | 28 | 8 | 4 |
| NS-B50027-4T5 | 16 | 111 | 49 | 76 | 27 | 8 | 2 |
| Min Cultivar Value | 14 | 79 | 47 | 72 | 25 | 6 | 2 |
| NS-B50027-4 | 14 | 110 | 49 | 76 | 28 | 8 | 3 |
| Max Cultivar Value | 27 | 125 | 50 | 76 | 29 | 9 | 13 |

| Line name | Harvest Plant Count Plant per m$^2$ | Alternaria Symptoms Score (1-9) | Blackleg Resistance Score (1-9) | Plant Vigor Score (1-9) | Grain moisture % | Grain % Garnet % | Grain Yield t/ha |
|---|---|---|---|---|---|---|---|
| ATR Bonito | 24 | 2 | 6 | 6 | 8 | 76 | 1.9 |
| ATR Gem | 23 | 3 | 6 | 6 | 8 | 79 | 2.0 |
| ATR Stingray | 26 | 3 | 7 | 5 | 6 | 61 | 1.7 |
| ATR Wahoo | 26 | 2 | 7 | 6 | 10 | 87 | 2.2 |
| AV Garnet | 23 | 3 | 7 | 6 | 8 | 100 | 2.6 |
| AV Jade | 27 | 2 | 7 | 7 | 7 | 85 | 2.1 |
| AV Zircon | 18 | 1 | 7 | 5 | 8 | 101 | 2.6 |
| Monola 515TT | 25 | 2 | 6 | 6 | 6 | 60 | 1.6 |
| DK 7444 | 23 | 2 | 7 | 7 | 5 | 113 | 2.8 |
| LL 130 | 21 | 2 | 7 | 6 | 6 | 114 | 2.9 |
| NS-B50027-4T3 | 16 | 2 | 8 | 4 | 8 | 80 | 2.1 |
| NS-B50027-4T5 | 18 | 2 | 8 | 6 | 9 | 82 | 2.3 |
| Min Cultivar Value | 18 | 1 | 6 | 5 | 5 | 60 | 1.7 |
| NS-B50027-4 | 18 | 2 | 8 | 5 | 8 | 81 | 2.2 |
| Max Cultivar Value | 26 | 3 | 7 | 7 | 10 | 114 | 2.9 |

Because canola line NS-B50027-4 is substantially homogeneous, it can be reproduced by planting seeds of such line, growing the resulting canola plants under self-pollinating or sib-pollinating conditions with adequate isolation, and harvesting the resulting seed using conventional agronomic practices.

Example 2. NS-B50027-4 Segregants

As noted above, NS-B50027-4 contains both a sixteen-gene insert (two inverted eight-gene cassettes) and a four-gene insert; each insert representing distinct loci within the plant genome. A combination of crossing, backcrossing, and self-crossing segregated the sixteen-gene insert to chromosome A05 ("Segregant A05 Locus"), and the four-gene insert to chromosome A02 ("Segregant A02 Locus"). Agronomic data for these segregants was compared with NS-B50027-4 and non-transgenic cultivars grown in four different experimental sites in Australia. A summary of the data is shown in Table 12, presenting mean values across the four experiment sites (analysis REML; F pr<0.001 Sig for all traits):

TABLE 12

Agronomic measurement data for non-transgenic canola cultivars and experimental transgenic test lines across four environments in 2016

| Line name | Emergence Plant per m$^2$ | Emergence Score (1-9) | Plant Height at Maturity cm | Start of Flowering Day | End of Flowering Day | Flowering Duration Days | Lodging at Maturity Score (1-9) | Shattered Seed No. | Harvest Plant Count Plant per m$^2$ | Plant Vigor Score (1-9) |
|---|---|---|---|---|---|---|---|---|---|---|
| ATR Bonito | 15.7 | 7.5 | 110.7 | 102.1 | 146.9 | 44.8 | 4.6 | 30.6 | 12.8 | 6.1 |
| ATR Gem | 17.7 | 7.6 | 115.4 | 103.0 | 148.9 | 46.0 | 4.5 | 40.4 | 14.0 | 6.5 |
| ATR Stingray | 18.9 | 7.3 | 100.9 | 100.7 | 147.2 | 46.5 | 3.4 | 74.6 | 15.4 | 5.4 |
| ATR Wahoo | 17.4 | 7.7 | 119.3 | 104.9 | 149.8 | 44.9 | 4.3 | 34.6 | 13.0 | 6.2 |
| AV Garnet | 18.8 | 7.7 | 126.9 | 101.7 | 148.5 | 46.7 | 4.8 | 41.8 | 13.9 | 7.1 |
| AV Jade | 17.2 | 7.7 | 117.6 | 100.0 | 147.9 | 47.9 | 4.9 | 50.9 | 16.1 | 7.4 |
| AV Zircon | 14.3 | 7.4 | 119.8 | 102.7 | 147.3 | 44.6 | 4.8 | 71.4 | 12.5 | 7.2 |
| Monola 515TT | 21.7 | 7.9 | 115.4 | 105.9 | 149.5 | 43.6 | 3.3 | 92.1 | 17.3 | 5.7 |
| NS-B50027-4 T3 | 12.8 | 6.3 | 120.7 | 106.5 | 149.6 | 43.2 | 2.8 | 45.0 | 10.7 | 5.2 |
| NS-B50027-4 T5 | 17.2 | 7.6 | 111.3 | 106.5 | 149.2 | 43.1 | 1.8 | 40.2 | 12.9 | 5.9 |
| Segregant A05 Locus | 15.7 | 7.2 | 94.9 | 102.3 | 150.1 | 47.7 | 1.9 | 27.6 | 15.1 | 4.8 |
| Segregant A02 Locus | 16.5 | 7.7 | 123.9 | 103.5 | 148.8 | 45.3 | 3.3 | 38.3 | 14.5 | 6.9 |
| Min Cultivar Value | 14.8 | 7.3 | 100.9 | 100.0 | 146.9 | 43.6 | 3.3 | 30.6 | 12.5 | 5.4 |
| NS-B50027-4 | 15.0 | 7.0 | 116.0 | 106.2 | 149.4 | 43.2 | 2.3 | 40.4 | 11.8 | 5.6 |
| Max Cultivar Value | 21.7 | 7.9 | 126.9 | 105.9 | 150.1 | 47.7 | 4.9 | 92.1 | 17.3 | 7.4 |

In addition to plant vigor and other agronomic features, grain yield (t/ha) was further characterized as shown in Table 13, in which percent oil was determined by NMR and AV Garnet was set as the 100% comparator for seed oil %:

TABLE 13

Grain yield (t/ha) and seed characterization data for non-transgenic canola cultivars and experimental transgenic test lines across four environments in 2016

| Line name: | Grain Yield t/ha | Grain moisture at harvest % | Seed Oil % | Oil at 6% moisture % |
|---|---|---|---|---|
| ATR Bonito | 3.46 | 8.3 | 86.8 | 46.8 |
| ATR Gem | 3.48 | 9.7 | 87.0 | 46.4 |
| ATR Stingray | 3.61 | 6.7 | 90.2 | 46.3 |
| ATR Wahoo | 3.76 | 10.9 | 93.8 | 46.6 |
| AV Garnet | 4.00 | 8.0 | 100.0 | 45.8 |
| AV Jade | 3.90 | 6.8 | 97.8 | 47.5 |
| AV Zircon | 3.73 | 6.8 | 93.1 | 47.8 |
| Monola 515TT | 3.16 | 9.3 | 79.2 | 45.2 |
| NS-B50027-4 T3 | 2.96 | 10.0 | 74.1 | 42.8 |
| NS-B50027-4 T5 | 2.83 | 9.8 | 70.7 | 41.4 |
| Segregant A05 Locus | 3.10 | 11.6 | 77.1 | 42.2 |
| Segregant A02 Locus | 4.21 | 10.0 | 105.2 | 46.8 |
| Min Cultivar Value | 3.26 | 6.8 | 79.2 | 45.2 |
| NS-B50027-4 | 2.90 | 9.9 | 72.4 | 42.0 |
| Max Cultivar Value | 4.00 | 10.9 | 100.0 | 47.8 |

The across-site mean DHA and LC-PUFA content for NS-B50027-4 T3 was about 6.2% DHA and about 7.1% LC-PUFA, and the across-site mean DHA and LC-PUFA content for NS-B50027-4 T5 was about 7.4% DHA and about 8.6% LC-PUFA, evidencing genetic gain from the T3 to the T5 generations.

Further regarding the Segregant A02 Locus, this transgenic line derived from NS-B50027-4 comprises the following four transgenes: Δ6-desaturase (derived from M pusilla), Δ5-elongase (derived from P. cordata), Δ5-desaturase (derived from P. salina), and Δ15/ω3-desaturase (derived from P. pastoris). Although this line expressed seed oil, Segregant A02 Locus lacks the enzymes required for production of LC-PUFA and DHA (see FIG. 1). In particular, it lacks a Δ12-desaturase that provides an early substrate, LA, a Δ6-elongase that converts SDA to ETA, and a Δ4-desaturase that converts DPA to DHA. As expected, a regulatory field trial showed that Segregant A02 Locus produced less than 1% LC-PUFA (EPA+DPA+DHA). In comparison, Segregant A05 Locus contains the complete suite of DHA biosynthesis enzymes, and the regulatory field trial showed that it produced about 4% DHA in about 4.5% LC-PUFA. Surprisingly, in the same regulatory field trial, NS-B50027-4 produced about 7.4% DHA in about 8.4% LC-PUFA (this trial experienced a non-optimal harvest). That NS-B50027-4 produced significantly more DHA than Segregant A05 Locus is surprising because, for example, Segregant A02 Locus does not provide an additional Δ4-desaturase that converts DPA to DHA. Segregant A02 Locus provides potential to improve yield.

Because the A02 and A05 loci can be segregated from NS-B50027-4 and used for further generation of NS-B50027-4 derived progeny. For example, a segregated A02 locus can be stacked in other LC-PUFA producing lines, such as a "Full Single" line comprising a single, seven-transgene insert for biosynthesis of DHA to increase LC-PUFA production in that line. Indeed, seed from F4 homozygous progeny stacked by introgression of the A02 locus in a Full Single recipient exhibited a 6% increase in DHA compared with the recipient Full Single line. Interestingly, these A02 locus-containing homozygous progeny produced more DHA than an F4 homozygous Full Single stacked with a segregated A05 locus. Note that NS-B50027-4 produced more DHA than Full Single, and Full Single stacked with NS-B50027-4 (both loci) also exhibited an increase in DHA production compared with Full Single.

The NS-B50027-4 A02 locus can also by introgressed into a recurrent Brassica or canola that produce other LC-PUFA, such as EPA or DPA, to increase production of LC-PUFA in that Brassica or canola. For example, transgenic B. juncea that produces substantial amounts of DPA in seed have been described. WO 2015089587. Introgression of the segregated NS-B50027-4 A02 locus into this B. juncea increased the amount of DPA produced in the seed. Similarly, Brassica transformed with the biosynthetic pathway for EPA production (e.g., transgenic insert(s) including neither Δ5-elongase nor Δ4-desaturase) produce substantial amounts of EPA in seed; and production of EPA is increased by introgressive hybridization with the A02 locus of NS-B50027-4.

Example 3. Kompetitive Allele Specific PCR (KASP) Assay

The phenotypic expression of transgenes in canola is determined both by the structure of the transgene cassette itself and by its insert location in the plant genome: the presence of transgenes at particular locations in the plant genome may influence the expression of the transgene and the overall phenotype of the plant. The incorporation of a recombinant DNA molecule in the plant genome typically results from transformation of a cell or tissue (or from another genetic manipulation). The particular site(s) of incorporation may be a matter of chance or predetermined (if a process of targeted integration is used). The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, breeding, and evaluation in field trials, eventually leading to the selection of an elite event.

NS-B50027-4 was developed following extensive selection breeding and field trials, and provides a canola cultivar that produces at about 7%-15% DHA (wt. % total fatty acid) in seed oil. Genetic analysis indicated that NS-B50027-4 had a transgenic insert on chromosome A02, and another transgenic insert on chromosome A05. The insert on A05 comprises two complete T-DNA-bordered cassettes of eight genes (Micpu-Δ6D, Pyrco-ASE, Paysa-ASD, Picpa-ω3D, Paysa-Δ4D, Lackl-Δ12D, Pyrco-Δ6E, and a PAT marker) aligned head-to-head (RB-LB:LB-RB). The insert on chromosome A02 comprises of a set of four genes Micpu-Δ6D, Pyrco-ASE, Paysa-ASD, and Picpa-ω3D. Surprisingly, segregation crossing showed that the inserts on both chromosome A02 and chromosome A05 were required to achieve DHA production of about 11%.

About 1200 progeny from eight different BC and F2 populations of DHA canola introgression breeding were used for DNA extraction based on LGC Octopure SOP developed in Nuseed Molecular Lab at Woodland. Briefly, two lyophilized leaf discs with diameter 0.25 inch were grounded in 300 μL of DNA extraction buffer (100 mM Tris-HCl, PH 8.0; 25 mM EDTA, PH 8.0; 0.5% SDS, 1.5 M NaCl) at 1,400 rpm for 8 minutes with GenoGrinder. After incubation in 55° C. water bath for 45 minutes and centrifuge at 4,500 rpm for 30 minutes, 50 μL of supernatant were transferred to 100 μL of LGC binding buffer with magnetic sbeadex beads. After binding and washing, the DNA was eluted to 80 μL of LGC DNA elution buffer.

DNA concentration was measured with NanoDrop 8000 (Thermo Scientific), and was in the range of 5.0-20.0 ng/μL with an average of 10.0 ng/μL. The DNA samples were diluted 1×. For each reaction, 2.0 μL (~5.0 ng/μL) genomic DNA sample and 2 μL master mix with primers were dispensed to 384-well plate for KASP genotyping.

In addition to the progeny from DHA canola introgression populations, eight controls were included in genotyping. These included two non-GMO controls (Dwarf and AV Jade), two hemizygous controls (2.5 ng Av Jade or 2.5 ng Dwarf+2.5 ng B0050-027-18-20-12-19); two event positive controls (B0050-027-18-20-12-19), and four non-template controls (NTCs). The positive control (T5 plant B0050-027-18-20-12-19) was previously used for characterization of the DHA canola event through sequencing.

KASP assays were developed to provide simple, cost-effective, high throughput, and flexible ways to detect and monitor the eight transgenes and the four NS-B50027-4-specific junctions, and to further facilitate NS-B50027-4 introgression in breeding programs. The KASP™ genotyping chemistry, assay design, genotyping, and scoring were performed according to the standard protocol of manufacturer (LGC Ltd., Middlesex, UK) with modifications.

Sequence information was uploaded into LGC Kraken Workflow Manager, and KASP assays were designed using its assay design program Primer Picker. A typical KASP assay includes two allele-specific primers (Primer_Allele X for transgenic allele and Primer_Allele Y for non-transgenic, wildtype allele) and one common locus-specific primer (Primer_Common). Primer_Allele X is associated with fluorescent FAM, and Primer_Allele Y with fluorescent HEX.

Most of the assays targeting the junctions were this type of three-primer assays (Table 14). For detection of DHA canola, four-primer assays were also developed in addition to conventional three-primer assays mentioned above. The four-primer assays had transgenic allele-specific Primer_Allele X, wildtype allele-specific Primer_Allele Y, Omega 3 gene-specific Primer_Common and wildtype-specific Primer_Common 2 in the reaction. For detection of the eight genes in Omega 3 cassette, only two primers, Primer_Allele X and Primer_Common, were used in each assay (two-primer assay); both primers were Omega 3 gene-specific (Table 14):

TABLE 14

Primer sequences of 28 KASP assays for detection and marker-assisted selection (MAS) of DHA canola

| ID | Target | Primer Name | SEQ ID NO | Primer Sequence (5'-3') |
|---|---|---|---|---|
| NBN01 | Micpu-Δ6D | Primer_Allele X | NO: 1 | GAAGGTGACCAAGTTCATGCTCCAAGCACCGTAG TAAGAGCA |
|  |  | Primer_Common | NO: 2 | GCTAAGAAGTGGGGACTCAACTACAA |
| NBN02 | Pyrco-Δ5E | Primer_Allele X | NO: 3 | GAAGGTGACCAAGTTCATGCTGCTCTTGCTGGAA CTCTTGG |
|  |  | Primer_Common | NO: 4 | GGGTTAGCCACATTGTAGGTAACGTA |
| NBN03 | Paysa-Δ5D | Primer_Allele X | NO: 5 | GAAGGTGACCAAGTTCATGCTTAAGAGACACCCT GGTGGAAAGA |
|  |  | Primer_Common | NO: 6 | TAGCATCAGTTCCAACTTGGTAAGCAAT |

TABLE 14-continued

Primer sequences of 28 KASP assays for detection and marker-assisted selection (MAS) of DHA canola

| ID | Target | Primer Name | SEQ ID NO | Primer Sequence (5'-3') |
|---|---|---|---|---|
| NBN04 | Picpa-ω3D | Primer_Allele X | NO: 7 | GAAGGTGACCAAGTTCATGCTGAACACGTAAGCAGACCAAGCAG |
| | | Primer_Common | NO: 8 | CCCTCTTCTCCCTAACGAATTCCTT |
| NBN05 | Pavsa-Δ4D | Primer_Allele X | NO: 9 | GAAGGTGACCAAGTTCATGCTGAGGAACCTGTTGCTGCTGATGA |
| | | Primer_Common | NO: 10 | GCGATCCTAGCACAAAGTTGAAGGTA |
| NBN06 | Lack1-Δ12D | Primer_Allele X | NO: 11 | GAAGGTGACCAAGTTCATGCTGGATGGATCGCTTACCTCTTCGT |
| | | Primer_Common | NO: 12 | CAGGGTAAGGTTGTCCTGTAACGTT |
| NBN07 | Pyrco-Δ6E | Primer_Allele X | NO: 13 | GAAGGTGACCAAGTTCATGCTCTATTGGATGGGGACTCAAGC |
| | | Primer_Common | NO: 14 | GGGAGATCCTTAGTAGCAGAAGAGAT |
| NBN08 | PAT | Primer_Allele X | NO: 15 | GAAGGTGACCAAGTTCATGCTCCTGAGAGGCGTCCTGTTGAAAT |
| | | Primer_Common | NO: 16 | AACAGCAGCCATATCAGCAGCAGTA |
| NBN57 | Upstream Junction of A02 Insert | Primer_Allele X | NO: 17 | GAAGGTGACCAAGTTCATGCTGCCTTCAGTTTAAACTATCAGTGTTTGA |
| | | Primer_Allele Y | NO: 18 | GAAGGTCGGAGTCAACGGATTGTTCTGTATACAACTTGTCGTGCTAC |
| | | Primer_Common | NO: 19 | GGGTTGTGTGAAAACGTGTGAGCAA |
| NBN68 | Upstream Junction of A02 Insert | Primer_Allele X | NO: 20 | GAAGGTGACCAAGTTCATGCTAAACTATCAGTGTTTGAACACCTC |
| | | Primer_Allele Y | NO: 21 | GAAGGTCGGAGTCAACGGATTACAACTTGTCGTGCTACACACCT |
| | | Primer_Common | NO: 22 | GACAAGTGAATCTGTTTGGGGTTG |
| NBN58 | Upstream Junction of A02 Insert | Primer_Allele X | NO: 23 | GAAGGTGACCAAGTTCATGCTGCCTTCAGTTTAAACTATCAGTGTTTGA |
| | | Primer_Allele Y | NO: 24 | GAAGGTCGGAGTCAACGGATTGTTCTGTATACAACTTGTCGTGCTAC |
| | | Primer_Common | NO: 25 | GAAAACGTGTGAGCAATTGTTGGAGGT |
| NBN85 | Upstream Junction of A02 Insert | Primer_Allele X | NO: 26 | GAAGGTGACCAAGTTCATGCTGCCTTCAGTTTAAACTATCAGTGTTTGA |
| | | Primer_Allele Y | NO: 27 | GAAGGTCGGAGTCAACGGATTGTTCTGTATACAACTTGTCGTGCTAC |
| | | Primer_Common | NO: 28 | GACAAGTGAATCTGTTTGGGGTTG |
| NBN14 | Upstream Junction of A02 Insert | Primer_Allele X | NO: 29 | GAAGGTGACCAAGTTCATGCTACAACTTGTCGTGCTACACACCT |
| | | Primer_Allele Y | NO: 30 | GAAGGTCGGAGTCAACGGATTAAACTATCAGTGTTTGAACACCTCC |
| | | Primer_Common | NO: 31 | GGTTGTGTGAAAACGTGTGAGC |
| NBN15 | Upstream Junction of A02 insert | Primer_Allele X | NO: 83 | GAAGGTGACCAAGTTCATGCTCTTTTAGCTAAATAAGAGGTTCTGTATACT |
| | | Primer_Allele Y | NO: 84 | GAAGGTCGGAGTCAACGGATTCTTTTAGCTAAATAAGAGGTTCTGTATACA |
| | | Primer_Common | NO: 85 | GATTGTGATTCCGGGCAGT |
| | | Primer_Common2 | NO: 86 | GTGTGAAAACGTGTGAGCAAT |
| NBN16 | Downstream Junction of A02 Insert | Primer_Allele X | NO: 32 | GAAGGTGACCAAGTTCATGCTTGTGAGCAATTGTTGGAGGT |
| | | Primer_Allele Y | NO: 33 | GAAGGTCGGAGTCAACGGATTTTGTGATTCCGGGCAGTAG |
| | | Primer_Common | NO: 34 | TCTTATCAACATTAAGAACATAATCTTTTAG |
| NBN62 | Downstream Junction of A02 Insert | Primer_Allele X | NO: 35 | GAAGGTGACCAAGTTCATGCTTTTAGCTAAATAAGAGGTTCTGTATACT |
| | | Primer_Allele Y | NO: 36 | GAAGGTCGGAGTCAACGGATTCTTTTAGCTAAATAAGAGGTTCTGTATACA |
| | | Primer_Common | NO: 37 | CAGGGATTGTGATTCCGGGCAGTA |
| | | Primer_Common2 | NO: 38 | GTGTGAGCAATTGTTGGAGGTGTGTA |

TABLE 14-continued

Primer sequences of 28 KASP assays for detection and marker-assisted selection (MAS) of DHA canola

| ID | Target | Primer Name | SEQ ID NO | Primer Sequence (5'-3') |
|---|---|---|---|---|
| NBN64 | Downstream Junction of A02 Insert | Primer_Allele X | NO: 39 | GAAGGTGACCAAGTTCATGCTCCGGGCAGTAGTAATTAATAATATAGTATTA |
| | | Primer_Allele Y | NO: 40 | GAAGGTCGGAGTCAACGGATTGGAGGTGTGTAGCACGACAAGTT |
| | | Primer_Common | NO: 41 | CTCAAACTTCTTATCAACATTAAGAACATA |
| NBN52 | Upstream Junction of A05 Insert | Primer_Allele X | NO: 42 | GAAGGTGACCAAGTTCATGCTGCCTTCAGTTTAAACTATCAGTGTTTG |
| | | Primer_Allele Y | NO: 43 | GAAGGTCGGAGTCAACGGATTCACGGTGGAGGTCACCATGT |
| | | Primer_Common | NO: 44 | CACGGAGATAGGCTGCATCTGAAT |
| NBN51 | Upstream Junction of A05 Insert | Primer_Allele X | NO: 45 | GAAGGTGACCAAGTTCATGCTGCCTTCAGTTTAAACTATCAGTGTTTG |
| | | Primer_Allele Y | NO: 46 | GAAGGTCGGAGTCAACGGATTCACGGTGGAGGTCACCATGT |
| | | Primer_Common | NO: 47 | GCTGCATCTGAATGACTGGTGTGTT |
| NBN09 | Upstream Junction of A05 Insert | Primer_Allele X | NO: 48 | GAAGGTGACCAAGTTCATGCTGTGTTCTTGGGTGGGTCTGTCCTTA |
| | | Primer_Allele Y | NO: 49 | GAAGGTCGGAGTCAACGGATTGTTCTTGGGTGGGTCTGTCCTTC |
| | | Primer_Common | NO: 50 | GTTGGCTAAGGTCACGGTGGAG |
| | | Primer_Common2 | NO: 51 | ATCCACTAGCAGATTGTCGTTTCCC |
| NBN50 | Upstream Junction of A05 Insert | Primer_Allele X | NO: 52 | GAAGGTGACCAAGTTCATGCTTCTTGGGTGGGTCTGTCCTTC |
| | | Primer_Allele Y | NO: 53 | GAAGGTCGGAGTCAACGGATTGTTCTTGGGTGGGTCTGTCCTTA |
| | | Primer_Common | NO: 54 | GATTGTCGTTTCCCGCCTTCAGTTT |
| | | Primer_Common2 | NO: 55 | CGTTGGCTAAGGTCACGGTGGA |
| NBN48 | Upstream Junction of A05 Insert | Primer_Allele X | NO: 56 | GAAGGTGACCAAGTTCATGCTTCTTGGGTGGGTCTGTCCTTC |
| | | Primer_Allele Y | NO: 57 | GAAGGTCGGAGTCAACGGATTGTTCTTGGGTGGGTCTGTCCTTA |
| | | Primer_Common | NO: 58 | CCGCCTTCAGTTTAAACTATCAGTGTTT |
| | | Primer_Common2 | NO: 59 | CGTTGGCTAAGGTCACGGTGGA |
| NBN10 | Upstream Junction of A05 Insert | Primer_Allele X | NO: 60 | GAAGGTGACCAAGTTCATGCTGGTCACGGTGGAGGTCACCA |
| | | Primer_Allele Y | NO: 61 | GAAGGTCGGAGTCAACGGATTCCGCCTTCAGTTTAAACTATCAGTGTT |
| | | Primer_Common | NO: 62 | GGTGTGTTCTTGGGTGGGTCTG |
| NBN83 | Downstream Junction of A05 Insert | Primer_Allele X | NO: 63 | GAAGGTGACCAAGTTCATGCTTCAGTTTAAACTATCAGTGTTACCT |
| | | Primer_Allele Y | NO: 64 | GAAGGTCGGAGTCAACGGATTACATGGTGACCTCCACCGTG |
| | | Primer_Common | NO: 65 | GTACTTTAAGCTTATAACCCTTTGTC |
| NBN82 | Downstream Junction of A05 Insert | Primer_Allele X | NO: 66 | GAAGGTGACCAAGTTCATGCTGGAGATCCACTAGCAGATTGTCGTT |
| | | Primer_Allele Y | NO: 67 | GAAGGTCGGAGTCAACGGATTCTTGGGTGGGTCTGTCCTTAC |
| | | Primer_Common | NO: 68 | GCAGGAGGTACTTTAAGCTTATA |
| NBN84 | Downstream Junction of A05 Insert | Primer_Allele X | NO: 69 | GAAGGTGACCAAGTTCATGCTGATTGTCGTTTCCCGCCTTCAGTTT |
| | | Primer_Allele Y | NO: 70 | GAAGGTCGGAGTCAACGGATTGTCCTTACATGGTGACCTCCAC |
| | | Primer_Common | NO: 71 | GTACTTTAAGCTTATAACCCTTTGTC |
| NBN66 | Downstream Junction of A05 Insert | Primer_Allele X | NO: 72 | GAAGGTGACCAAGTTCATGCTGATTGTCGTTTCCCGCCTTCAGTTT |
| | | Primer_Allele Y | NO: 73 | GAAGGTCGGAGTCAACGGATTGTCCTTACATGGTGACCTCCAC |
| | | Primer_Common | NO: 74 | GCAGGAGGTACTTTAAGCTTATA |
| NBN41 | Downstream Junction of A05 Insert | Primer_Allele X | NO: 75 | GAAGGTGACCAAGTTCATGCTTTTTTATTCAACCGTTGGCTAAGGTA |
| | | Primer_Allele Y | NO: 76 | GAAGGTCGGAGTCAACGGATTTTTTATTCAACCGTTGGCTAAGGTC |
| | | Primer_Common | NO: 77 | GATTGTCGTTTCCCGCCTTCAGTTT |
| | | Primer_Common2 | NO: 78 | TTCTTGGGTGGGTCTGTCCTTACAT |

TABLE 14-continued

Primer sequences of 28 KASP assays for detection and marker-assisted selection (MAS) of DHA canola

| ID | Target | Primer Name | SEQ ID NO | Primer Sequence (5'-3') |
|---|---|---|---|---|
| NBN43 | Downstream Junction of A05 Insert | Primer_Allele X | NO: 79 | GAAGGTGACCAAGTTCATGCTTTTTTATTCAACC GTTGGCTAAGGTA |
| | | Primer_Allele Y | NO: 80 | GAAGGTCGGAGTCAACGGATTTTTTATTCAACCG TTGGCTAAGGTC |
| | | Primer_Common | NO: 81 | GGAGATCCACTAGCAGATTGTCGTT |
| | | Primer_Common2 | NO: 82 | TTCTTGGGTGGGTCTGTCCTTACAT |
| NBN11 | Downstream Junction of A05 Insert | Primer_Allele X | NO: 87 | GAAGGTGACCAAGTTCATGCTACTTTTTTTCAA CTGTTGGCTAAGGTA |
| | | Primer_Allele Y | NO: 88 | GAAGGTCGGAGTCAACGGATTACTTTTTTTCAA CTGTTGGCTAAGGTC |
| | | Primer_Common | NO: 89 | GTGTGTTCTTGGGTGGGTCTG |
| | | Primer_Common2 | NO: 90 | GTCGTTTCCCGCCTTCAGTTT |

The KASP genotyping system requires two components: the assay mix and the master mix. The assay mix is a mixture of required primers, and the master mix contains all other required components, including PCR buffer, the universal fluorescent reporting system, and Taq polymerase.

The KASP reaction was run in the volume of 4.0 μL, consisting 2.0 μL (10.0 ng) of genomic DNA, 2.0 μL of 2×KASP master mix, and 0.06 μL of the assay (primer) mix. The assay (primer) mix is a combination of 12 μM of allele-specific Primer_Allele X and 12 μM of Primer_Common for two-primer assays, a combination of 12 μM of allele-specific Primer_Allele X, 12 μM of allele-specific Primer_Allele Y, and 30 μM of Primer_Common for three-primer assays, and a combination of 12 μM of allele-specific Primer_Allele X, 12 μM of allele-specific Primer_Allele Y, 12 μM of Primer_Common and 12 μM of Primer_Common2 for the four-primer assays.

The reactions were run in 384-well plate in LGC Hydrocycler 16 with the following cycling parameters: 1 cycle of 94° C. for 15 min, followed by eight cycles of 94° C. for 30 sec and 64° C.-57° C. (drop 1.0° C. per cycle) for 60 sec, and followed by thirty cycles of 94° C. for 30 sec and 57° C. for 60 sec. If clear genotyping clusters have not been obtained, the plate was further thermally cycled by three extra cycles of 94° C. for 30 sec and 57° C. for 60 sec.

After the completion of KASP reactions, transgenic allele was labeled with FAM through Primer_Allele X, and non-transgenic, wildtype allele was label with HEX through Primer_Allele Y. The fluorescent signals were read in a PheraStar microplate reader with an excitation wavelength of 485 nm and an emission wavelength of 520 nm for FAM and 535 nm/556 nm for HEX. Data were analyzed using LGC Kraken database.

Eight gene-specific, dominant (NBN01-NBN08; one assay/gene) were developed for detection of eight genes in the construct cassette. A total of twenty insert-specific, co-dominant KASP assays, which targeted the upstream (NBN57, NBN68, NBN58, NBN85 and NBN14) and downstream (NBN16, NBN62 and NBN64) junctions of the insert on A02, and the upstream (NBN52, NBN51, NBN09, NBN50, NBN48 and NBN10) and downstream (NBN83, NBN82, NBN84, NBN66, NBN41 and NBN43) junctions of insert on A05, were developed and validated with 1200 progeny from NS-B50027-4 introgression populations (Table 14). Over 10,000 samples have been genotyped with these markers.

Thirty Kompetitive Allele Specific PCR (KASP) assays were developed and validated, which target the eight genes and the four junctions of the two inserts of DHA canola event NS-B50027-4. These assays offered a simple, cost-effective, high throughput and flexible approach to detect and monitor NS-B50027-4 in a breeding program.

Example 4. Detailed Comparison of NS-B50027-4 and Non-Transgenic Canola

Data from canola seed production in experimental field plots from 2014-2016 were tabulated. The range of DHA and total EPA+DPA+DHA were based on several test field observations. Content of major fatty acids in both NS-B50027-4 and non-transgenic "Control" canola may vary by several percentage points depending on growing conditions. In the following Table 15, "0.0" may refer to a trace amount identified as below the amount needed to accurately determine the quantity of the component:

TABLE 15

Detailed comparison of fatty acid content of NS-B50027-4 with control

| Fatty acid | | NS-B50027-4 (%) | Control Canola (%) |
|---|---|---|---|
| Myristic | C14:0 | 0.1 | 0.1 |
| Palmitic | C16:0 | 4.3 | 3.9 |
| Palmitoleic | C16.1 | 0.2 | 0.2 |
| Stearic | C18:0 | 2.2 | 1.6 |
| Oleic | C18:1n9c | 38.7 | 63.6 |
| Cis-vaccenic | C18:1n7c | 4.2 | 3.5 |
| Linoleic | C18:2n6c | 7.8 | 13.1 |
| GLA | C18:3n6 | 0.6 | 0.0 |
| ALA | C18:3n3 | 21.7 | 10.3 |
| Arachidic | C20:0 | 0.6 | 0.6 |
| SDA | C18:4n3 | 2.2 | 0.0 |
| Gondoic | C20:1n9c | 1.3 | 1.5 |
| Heneicosanoic | C21:0 | 0.0 | 0.0 |
| DGLA | C20:3n6 | 0.0 | 0.0 |
| ETE | C20:3n3 | 0.7 | 0.0 |
| Behenic | C22:0 | 0.3 | 0.3 |
| ETA | C20:4n3 | 0.0 | 0.0 |
| Erucic | C22:1n9c | 0.0 | 0.0 |
| EPA | C20:5n3 | 0.4 | 0.0 |
| Lignoceric | C24:0 | 0.2 | 0.1 |
| DPA6 | C22:5n6 | 0.0 | 0.0 |
| Nervonic | C24:1n9c | 0.1 | 0.2 |
| DPA3 | C22:5n3 | 0.9 | 0.0 |
| DHA | C22:6n3 | 9.8 (8-10) | 0.0 |
| Other | | 3.8 | 1.3 |
| Sum: EPA + | | 11.1 (10-12) | 0.0 |

TABLE 15-continued

Detailed comparison of fatty acid content of NS-B50027-4 with control

| Fatty acid | NS-B50027-4 (%) | Control Canola (%) |
|---|---|---|
| DPA + DHA | | |
| Total Omega 3 | 35.7 | 10.4 |
| Total Omega 6 | 8.4 | 11.3 |
| ω3/ω6 | 4.3 | 0.9 |
| Total Saturated | 7.7 | 6.7 |
| Total Monounsaturated | 44.5 | 68.9 |
| Total Polyunsaturated | 44.1 | 23.5 |

Seed harvested from experimental cultivation of NS-B50027-4 was crushed and oil obtained via cold-press. Seed harvested from the parental isogenic line, AV Jade, was similarly processed, and the content of each oil compared as shown in Table 16:

TABLE 16

NS-B50027-4 Oil Content

| Component (units) | NS-B50027-4 | AV Jade |
|---|---|---|
| Saturated TAG (%) | | |
| C4:0 Butyric | <0.1 | <0.1 |
| C6:0 Caproic | <0.1 | <0.1 |
| C8:0 Caprylic | <0.1 | <0.1 |
| C10:0 Capric | <0.1 | <0.1 |
| C12:0 Lauric | <0.1 | <0.1 |
| C14:0 Myristic | <0.1 | <0.1 |
| C15:0 Pentadecanoic | <0.1 | <0.1 |
| C16:0 Palmitic | 4.3 | 3.9 |
| C17:0 Margaric | <0.1 | <0.1 |
| C18:0 Stearic | 2.9 | 2.5 |
| C20:0 Arachidic | 0.8 | 0.5 |
| C22:0 Behenic | 0.4 | 0.2 |
| C24:0 Lignoceric | 0.1 | 0.1 |
| Total Saturated | 8.7 | 7.3 |
| Mono-unsaturated TAG (%) | | |
| C14:1 Myristoleic | <0.1 | <0.1 |
| C16:1 Palmitoleic | 0.2 | 0.1 |
| C17:1 Heptadecenoic | <0.1 | <0.1 |
| C18:1 Oleic | 44.9 | 58.8 |
| C20:1 Eicosenic | 1.3 | 1.0 |
| C22:1 Docosenoic | <0.1 | <0.1 |
| C24:1 Nervonic | <0.1 | <0.1 |
| PUFA TAG (%) | | |
| C18:2ω6 Linoleic | 7.6 | 18.9 |
| C18:3ω6 gamma-Linolenic | 0.5 | <0.1 |
| C18:3ω3 alpha-Linolenic | 20.9 | 10.5 |
| C20:2ω6 Eicosadienoic | <0.1 | <0.1 |
| C20:3ω6 Eicosatrienoic | <0.1 | <0.1 |
| C20:3ω3 Eicosatrienoic | 0.6 | <0.1 |
| C20:4ω6 Arachidonic | <0.1 | <0.1 |
| C20:5ω3 Eicosapentaenoic | 0.4 | <0.1 |
| C22:2ω6 Docosadienoic | <0.1 | <0.1 |
| C22:4ω6 Docosatetraenoic | <0.1 | <0.1 |
| C22:5ω3 Docosapentaenoic | 1.0 | <0.1 |
| C22:6ω3 Docosahexaenoic | 9.4 | 0.2 |
| Total PUFA (%) | 40.6 | 29.9 |
| Total Mono Trans Fatty Acids | 0.1 | 0.2 |
| Total Poly Trans Fatty Acids | 0.8 | 0.2 |
| P:M:S Ratio | 4.7:5.4:1 | 4.1:8.2:1 |

TABLE 16-continued

NS-B50027-4 Oil Content

| Component (units) | NS-B50027-4 | AV Jade |
|---|---|---|
| PUFA (%) | | |
| Omega 3 Fatty Acids | 32.3 | 10.9 |
| Omega 6 Fatty Acids | 8.2 | 19.0 |
| ω3:ω6 | 3.94 | 0.57 |
| Vitamins | | |
| beta-Carotene (µg/100 g) | 110 | 82 |
| alpha-tocopherol (mg/100 g) | 19 | 15 |
| beta-tocopherol (mg/100 g) | <0.1 | <0.1 |
| delta-tocopherol (mg/100 g) | 0.6 | 0.8 |
| gamma-tocopherol (mg/100 g) | 43 | 42 |
| Astaxanthin (mg/kg) | <0.05 | <0.05 |
| Vitamin K1 (µg/100 g) | 17 | 15 |
| Phytosterols (mg/100 g) | | |
| Cholesterol | <5.0 | <5.0 |
| Brassicasterol | 29 | 67 |
| Campesterol | 250 | 170 |
| Campestanol | <5.0 | <5.0 |
| Stigmasterol | <5.0 | <5.0 |
| beta-Sitosterol | 370 | 320 |
| beta-Sitostanol | 34 | 27 |
| Total Phytosterol | 690 | 600 |

In accordance with the Budapest Treaty on the International Recognition of the Deposit of Microorganisms for the Purposes of Patent Procedure (1977), Applicants made a deposit of at least 2500 seeds of Canola NS-B50027-4 with the American Type Culture Collection (ATCC®), Manassas, VA, 20110-2209, U.S.A., on Jun. 9, 2016, which has been assigned Accession Number PTA-123186. During pendency of this application, access to the invention may be afforded to the Commissioner of the United States Patent and Trademark Office by request; all restrictions upon availability to the public are irrevocably revoked upon granting of the patent; the deposit of line NS-B50027-4 will be maintained in the ATCC® depository, which is a public depository, for a period of 30 years, or 5 years after the most recent seed request, or for the effective life of the patent, whichever is longer; and seed will be replaced with viable seed if deposited seed becomes nonviable during that period. The viability of the seeds was tested at the time of deposit. Appendix A submitted herewith provides deposit date, Accession Number, and acknowledgement of viability. Applicants have satisfied all the requirements of 37 C.F.R. §§ 1.801-1.809. Applicants impose no restrictions on the availability of the deposited material from the ATCC®; however, Applicant has no authority to waive any restrictions imposed by law on the transfer of biological material or its transportation in commerce. Applicant does not waive any infringement of its rights as granted under a patent issued from this application or under the Plant Variety Protection Act (7 U.S.C. § 2321 et seq.).

Although the foregoing embodiments have been described in some detail by way of illustration and example for purposes of clarity and understanding, it will be clear to one of skill in the art that certain changes and modifications, such as single gene modifications and mutations, somoclonal variants, variant individuals selected from large populations of the plants of the instant inbred line, and the like, may be practiced within the scope of the invention which is limited solely by the appended claims.

We claim:

1. A segregant of inbred canola line NS-B50027-4, having been deposited under ATCC Accession Number PTA-123186, wherein said NS-B50027-4 contains within its genome:
   a first transgenic locus located on chromosome A02 comprising one copy of each of a *Micromonas pusilla* Δ6-desaturase, a *Pyramimonas cordata* Δ5-elongase, a *Pavlova salina* Δ5-desaturase, and a *Pichia pastoris* Δ15/ω3-desaturase gene, and
   a second transgenic locus located on chromosome A05 comprising two copies of each of a *M. pusilla* Δ6-desaturase, a *P. cordata* Δ5-elongase, a *P. salina* Δ5-desaturase, a *P. pastoris* Δ15/ω3-desaturase, a *Pavlova salina* Δ4-desaturase, a *Lachancea kluyveri* Δ12-desaturase, and a *P. cordata* Δ6-elongase gene; and wherein said segregant is a *Brassica* plant that comprises within its genome only said first transgenic locus.

2. A part of the segregant *Brassica* plant of claim 1, wherein said part is at least one of seed, leaf, pollen, embryo, root, root tip, pod, flower, ovules, stalk, cell, protoplast, cotyledon, half-cotyledon, hypocotyl, radicle, cell culture, tissue culture, or gamete, and wherein said part comprises within its genome only said first transgenic locus.

* * * * *